(12) United States Patent
Denny et al.

(10) Patent No.: US 9,198,913 B2
(45) Date of Patent: Dec. 1, 2015

(54) NITROIMIDAZOOXAZINES AND THEIR USES IN ANTI-TUBERCULAR THERAPY

(75) Inventors: William Alexander Denny, Auckland (NZ); Andrew Mark Thompson, Auckland (NZ); Adrian Blaser, Waitakere City (NZ); Zhenkun Ma, Westfield, NJ (US); Brian Desmond Palmer, Waitakere City (NZ); Hamish Scott Sutherland, Auckland (NZ); Iveta Kmentova, Jahodna (SK)

(73) Assignee: Global Alliance for TB Drug Development, New York, NY (US)

( * ) Notice: Subject to any disclaimer, the term of this patent is extended or adjusted under 35 U.S.C. 154(b) by 88 days.

(21) Appl. No.: 12/847,452

(22) Filed: Jul. 30, 2010

(65) Prior Publication Data

US 2012/0028973 A1 Feb. 2, 2012

Related U.S. Application Data

(60) Provisional application No. 61/230,396, filed on Jul. 31, 2009.

(51) Int. Cl.
*A61K 31/5365* (2006.01)
*C07D 498/04* (2006.01)

(52) U.S. Cl.
CPC .......... *A61K 31/5365* (2013.01); *C07D 498/04* (2013.01)

(58) Field of Classification Search
None
See application file for complete search history.

(56) References Cited

U.S. PATENT DOCUMENTS

| | | | |
|---|---|---|---|
| 5,574,051 A | 11/1996 | Wrobel et al. | |
| 5,605,918 A | 2/1997 | Wrobel et al. | |
| 5,668,127 A | 9/1997 | Baker et al. | |
| 6,087,358 A | 7/2000 | Baker et al. | |
| 7,262,212 B2 | 8/2007 | Tsubouchi et al. | |
| 7,666,864 B2 | 2/2010 | Ding et al. | |
| 2005/0256128 A1* | 11/2005 | Arora et al. | 514/252.13 |

FOREIGN PATENT DOCUMENTS

| WO | 2006043121 A1 | 4/2006 |
|---|---|---|
| WO | 2007075872 A2 | 7/2007 |

OTHER PUBLICATIONS

Palmer et al. "Synthesis and Structure-Activity Studies of Biphenyl Analogues of the Tuberculosis Drug (6S)-2-nitro-6-{[4-(trifluoromethoxy)benzyl]oxy}-6,7-dihydro-5H-imidazo[2,1-b][1,3]oxazine (PA-824)". J. Med. Chem. 2010; 53:282-294.*
Anderson, Robert F., et al; Intermediates in the reduction of the antituberculosis drug PA-824, (6S)-2-nitro-6-{[4(trifluoromethoxy)benzyl]oxy}-6,7-dihydro-5H-imidazo[2,1-b][1,3]oxazine, in aqueous solution, Organic & Biomolecular Chemistry, 2008, 6, pp. 1973-1980.
Cho, Sang Hyun; Low-Oxygen-Recovery Assay for High-Throughput Screening of Compounds against Nonreplicating Mycobaterium tuberculosis, Antimicrobial Agents and Chemotherapy, Apr. 2007, vol. 51, No. 4, pp. 1380-1385.
Collins, Lisa A., et al; Microplate Alamar Blue Assay versus BACTEC 460 System for High-Throughput Screening of Compounds against *Mycobacterium tuberculosis* and *Mycobacterium avium*, Antimicrobial Agents and Chemotherapy, May 1997, vol. 41, No. 5, pp. 1004-1009.
Desolms, S. Jane, et al; Dual Protein Farnesyltransferase—Geranylgeranyltransferase-I Inhibitors as Potential Cancer Chemotherapeutic Agents, J. Med. Chem., 2003, 46, pp. 2973-1984.
Edsall, Jr., Richard J., et al; EIRβ Ligands. Part 1: The Discovery of ERβ Selective Ligands which Embrace the 4-Hydroxy-biphenyl Template, Bioorganic & Medicinal Chemistry 11, 2003, pp. 3457-3474.
Falzari, Kanakeshwari, et al; In Vitro and in Vivo Activities of Macrolide Derivatives against *Mycobacterium tuberculosis*, Antimicrobial Agents and Chemotherapy, Apr. 2005, vol. 49, No. 4, pp. 1447-1454.
Ferrara, Giovanni, et al; Use in routine clinical practice of two commercial blood tests for diagnosis of infection with *Mycobacterium tuberculosis*: a prospective study, Lancet 2006, vol. 367, pp. 1328-1334.
Kiener, A., et al; Regiospecific Enzymatic Hydroxylations of Pyrazinecarboxylic Acid and a Practical Synthesis of 5-Chloropyrazine-2-Carboxylic Acid, Synlett 10, 1994, pp. 814-816.
Kim, Pilho, et al; Structure—Activity Relationships of Antitubercular Nitroimidazoles. 1. Structural Features Associated with Aerobic and Anaerobic Activities of 4- and 5-Nitroimidazoles, J. Med. Chem., 2009, vol. 52, pp. 1317-1328.
Kim, Pilho, et al; Structure—Activity Relationships of Antitubercular Nitroimidazoles. 2. Determinants of Aerobic Activity and Quantitative Structure—Activity Relationships, J. Med. Chem., 2009, vol. 52, pp. 1329-1344.
Li, Xiaojin, et al; Synthesis and antitubercular activity of 7-(R)- and 7-(S)-methyl-2-nitro-6-(S)-(4-(trifluoromethoxy) benzyloxy)-6,7-dihydro-5H-imidazo[2,1-b][1,3]oxazines, analogues of PA-824, Bioorganic & Medicinal Chemistry Letters 18, 2008, pp. 2256-2262.
Manjunatha, Ujjini H., et al; Identification of a nitroimidazo-oxazine-specific protein involved in PA-824 resistance in Mycobacterium tuberculosis, PNAS, Jan. 10, 2006, vol. 103, No. 2, pp. 431-436.
Sasaki, Hirofumi, et al; Synthesis and Antituberculosis Activity of a Novel Series of Optically Active 6-Nitro-2,3-dihydroimidazo[2,1-b]oxazoles, J. Med. Chem. 2006, 49, pp. 7854-7860.
Schubert, Ulrich S., et al; Synthesis of 5,5"-Bisfunctionalized 2,2': 6',2"-Terpyridines using Functionalized Pyridine Building Blocks, Synlett 1999, No. 3, pp. 342-344.

(Continued)

*Primary Examiner* — Leslie A. Royds Draper
(74) *Attorney, Agent, or Firm* — Jackson Walker L.L.P.

(57) ABSTRACT

The present invention relates to novel nitroimidazooxazines, to their preparation, and to their use as drugs for treating *Mycobacterium tuberculosis* and other microbial infections, either alone or in combination with other anti-infective treatments.

9 Claims, 28 Drawing Sheets

(56) References Cited

OTHER PUBLICATIONS

Singh, Ramandeep, et al; PA-824 Kills Nonreplicating *Mycobacterium tuberculosis* by Intracellular no Release, Science, Nov. 28, 2008, vol. 322, pp. 1392-1395.
Stover, C. Kendall; A small-molecule nitroimidazopyran drug candidate for the treatment of tuberculosis, Nature, Jun. 22, 2000, vol. 405, pp. 962-966.
Tyagi, Sandeep, et al; Bactericidal Activity of the Nitroimidazopyran PA-824 in a Murine Model of Tuberculosis, Antibacterial Agents and Chemotherapy, Jun. 2005, vol. 49, No. 6, pp. 2289-2293.
Van Den Heuvel, Marco, et al; Synthesis of a Non-Heme Template for Attaching Four Peptides: An Approach to Artificial Iron (II)-Containing Peroxidases, J. Org. Chem. 2004, vol. 69, No. 2, pp. 250-262.
Thompson, Andrew M., et al.; "Synthesis, Reduction Potentials, and Antitubercular Activity of Ring A/B Analogues of the Bioreductive Drug (6S)-2-Nitro-64[4-(trifluoromethoxy)benzyl]oxy}-6,7-dihydro-5H-imidazo[2,1-b][1,3]oxazine (PA-824)," Journal of Medicinal Chemistry, vol. 52, No. 3, 2009, pp. 637-645.
European Patent Office, Invitation to Pay Additional Fees and, Where Applicable, Protest Fee, Partial International Search, Application No. PCT/US2010/043906, Nov. 12, 2010.
European Patent Office; Written Opinion; PCT Application No. PCT/US2010/043906; Nov. 22, 2011.
European Patent Office; International Preliminary Report on Patentability; PCT Application No. PCT/US2010/043906; Feb. 10, 2012.
European Patent Office, International Search Report, Application No. PCT/US2010/043906, Jan. 13, 2011.
Sutherland, Hamish, S., et al., Synthesis and Structure—activity Relationships of Antitubercular 2-Nitroimidazooxazines Bearing Heterocyclic Side Chains, J. Med. Chem., Jul. 12, 2009, 53, 855-866.
New Zealand Patent Office; Office Action; New Zealand Patent Application No. 598121; Oct. 23, 2012.
New Zealand Patent Office; Response to Office Action (including enclosures 1 and 3-7); New Zealand Patent Application No. 598121; Apr. 9, 2013.
New Zealand Patent Office; Response to Office Action (enclosure 2 only); New Zealand Patent Application No. 598121; Apr. 9, 2013.
Russian Patent Office; Response to Office Action; Russian Patent Application No. 2012107176; Jul. 14, 2014; 14 pages.
Chinese Patent Office; Response to First Office Action; Chinese Patent Application No. 201080041453.9; Jul. 10, 2014; 11 pages.
European Patent Office; Office Action; European Patent Application No. 10742955.7; Jun. 20, 2013; 4 pages.
European Patent Office; Response to Office Action; European Patent Application No. 10742955.7; Jul. 30, 2013; 7 pages.
European Patent Office; Office Action; European Patent Application No. 10742955.7; Sep. 6, 2013; 3 pages.
Japanese Patent Office; English translation of the amended claims; Japanese Patent Application No. 2012-523087; Jul. 30, 2013; 4 pages.
Russian Patent Office; Office Action (English translation); Russian Application No. 2012107176; Jul. 25, 2014.
Russian Patent Office; Response to Office Action; Russian Application No. 2012107176; Sep. 24, 2014.
Japanese Patent Office; Office Action; Japanese Application No. 2012-523087; Sep. 9, 2014.
Japanese Patent Office; Office Action (English translation); Japanese Application No. 2012-523087; Sep. 9, 2014.
European Patent Office; Response to Office Action; European Patent Application No. 10742955.7; Oct. 30, 2013; 11 pages.
Chinese Patent Office; Office Action; Chinese Patent Application No. 201080041453.9; Dec. 26, 2013; 7 pages.
Chinese Patent Office; Office Action (in English); Chinese Patent Application No. 201080041453.9; Dec. 26, 2013; 7 pages.

\* cited by examiner compounds 8 and 9 of Table 1

NITROIMIDAZOOXAZINES AND THEIR USES IN ANTI-TUBERCULAR THERAPY

This application claims priority to U.S. Provisional Patent Application Ser. No. 61/230,396, entitled "Nitroimidazooxazines and Their Uses in Anti-Tubercular Therapy," filed on Jul. 31, 2009, the entire content of which is hereby incorporated by reference.

BACKGROUND

The present invention relates to novel nitroimidazooxazines, to their preparation, and to their use as drugs for treating *Mycobacterium tuberculosis* and other microbial infections, either alone or in combination with other anti-infective treatments.

Tuberculosis remains a leading infectious cause of death worldwide (mortality estimated to be 1.3 million in 2008), with a recent resurgence attributable to an enhanced susceptibility in HIV patients, the increasing incidence of multidrug-resistant strains and the emergence of extensively drug resistant strains. Current drug therapy for tuberculosis is long and complex, involving multidrug combinations (usually isoniazid, rifampin, pyrazinamide and ethambutol) given daily for in excess of 6 months. Furthermore, these drugs are relatively ineffective against the persistent form of the disease, which is suggested to occur in a significant proportion of cases (Ferrara et al., 2006). Second-line drugs used in lengthy combination therapies for multidrug resistant disease (typically over 2 years) mostly have reduced potency or greater toxicity than existing first-line agents. Frequently, incomplete treatment is administered, leading to high relapse rates and increased drug resistance, underscoring the urgent need for new, more effective drugs.

It is an object of the present invention to provide new nitroimidazooxazines with unexpectedly high potency against both aerobic (replicating) and hypoxic (latent or persistent) cultures of *Mycobacterium tuberculosis* and unexpectedly high efficacy in mouse models of *Mycobacterium tuberculosis* infection for use as anti-tubercular drugs and for the treatment of other microbial infections.

SUMMARY

The current invention pertains to nitroimidazooxazine compounds, their methods of preparation, and uses of the compounds as treatment for tuberculosis and other microbial infections.

The recent introduction of the nitroimidazooxazine PA-824 to clinical trial is significant, as this compound shows good in vitro and in vivo activity against *Mycobacterium tuberculosis* in both its active and persistent forms (Tyagi et al., 2005). A related 2-nitroimidazo[2,1-b]oxazole, OPC-67683 is also in clinical trial (Sasaki et al., 2006). The structures of these compounds are shown in FIG. 1. Without wanting to be bound by theory, the mechanism of action of PA-824 is suggested to involve the release of nitric oxide (Singh et al., 2008), following a reductive step, in a process dependent on the bacterial glucose-6-phosphate dehydrogenase (FGD1) and its cofactor F420 (Stover et al., 2000). Microarray studies on mutant strains wild-type for both FGD1 and F420 show that a 151-amino acid (17.37 kDa) protein of unknown function, Rv3547, appears to be critical for this activation (Manjunatha et al., 2006). Recent mechanistic studies of the reductive chemistry of PA-824 support this contention (Anderson et al., 2008). Nitroimidazooxazine analogues and their use in tuberculosis have been previously reported (U.S. Pat. No. 5,668,127 (1997) and U.S. Pat. No. 6,087,358 (2000); Jiricek et al., WO 2007075872A2 (2007); Li et al., 2008; Kim et al., 2009).

In a first aspect, the present invention pertains to a compound having a general structure of Formula I:

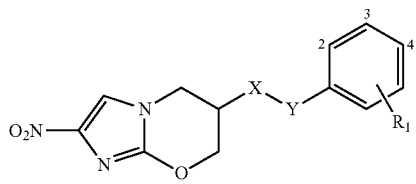

I wherein X represents O, OCH$_2$, OCH$_2$CH=CH or OCH$_2$C≡C;

Y represents any one of formulae IIa-IId shown below, where ◆— signifies the attachment to X;

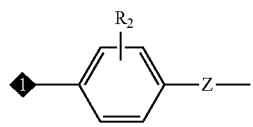

IIa

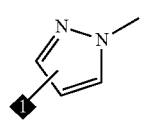

IIb

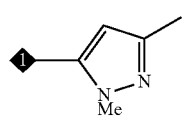

IIc

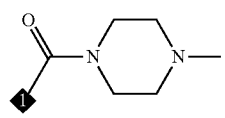

IId

Z in Formula IIa represents CH$_2$, CH'CH, C≡C or a direct bond; and

R$_1$ and R$_2$ in Formulae I and IIa each represents any one, two or three of H, F, Cl, CF$_3$, OCF$_2$H, OCF$_3$, aza (—CH= replaced by —N=), or diaza (—CH=CH— replaced by —N=N—, —CH=CH—CH= replaced by —N=CH—N=, or —CH=CH—CH=CH— replaced by —N=CH—CH=N—) at any of the available ring positions.

A preferred subclass of compounds has a general structure of Formula I above wherein:

X represents O, OCH$_2$, OCH$_2$CH=CH or OCH$_2$C≡C;

Y represents any one of formulae IIa-IId shown below, where ◆— signifies the attachment to X;

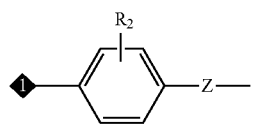

IIa

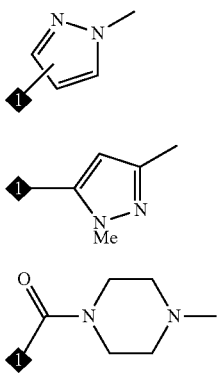

Z in Formula IIa represents CH$_2$, CH=CH, C≡C or a direct bond;

R$_1$ in Formula I represents 4-F or 4-OCF$_3$ or 2-Cl, 4-OCF$_3$ or 3-Cl, 4-OCF$_3$ or 3-F, 4-OCF$_3$ or 2-aza, 4-CF$_3$ or 3-aza, 4-CF$_3$ or 2-aza, 4-F;

R$_2$ in Formula IIa represents any one or two of H, F or aza (—CH=replaced by —N=) at any of the available ring positions.

These compounds, as well as mixtures thereof, isomers, physiologically functional salt derivatives, and prodrugs thereof, are useful in prevention of or therapy for treating *Mycobacterium tuberculosis* and other microbial infections.

DETAILED DESCRIPTION

The current invention pertains to nitroimidazooxazine compounds, their methods of preparation, and uses of the compounds as treatment for tuberculosis and other microbial infections.

In a first aspect, the present invention pertains to a compound having a general structure of Formula I:

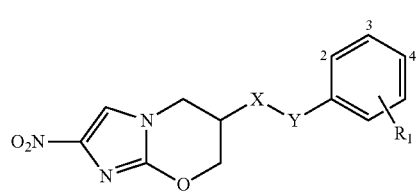

wherein X represents O, OCH$_2$, OCH$_2$CH=CH or OCH$_2$C≡C;

Y represents any one of formulae IIa-IId shown below, where ◆— signifies the attachment to X;

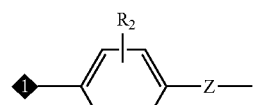

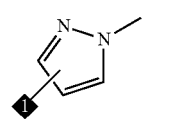

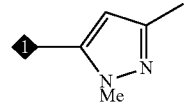

-continued

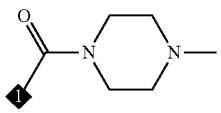
IId

Z in Formula IIa represents CH$_2$, CH=CH, C≡C or a direct bond; and

R$_1$ and R$_2$ in Formulae I and IIa each represents any one, two or three of H, F, Cl, CF$_3$, OCF$_2$H, OCF$_3$, aza (—CH= replaced by —N=), or diaza (—CH=CH— replaced by —N=N—, —CH=CH—CH= replaced by —N=CH—N=, or —CH=CH—CH=CH— replaced by —N=CH—CH=N—) at any of the available ring positions.

A preferred subclass of compounds has a general structure of Formula I above wherein:
X represents O, OCH$_2$, OCH$_2$CH=CH or OCH$_2$C≡C;
Y represents any one of formulae IIa-IId shown below, where ◆— signifies the attachment to X;

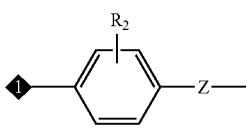
IIa

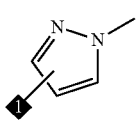
IIb

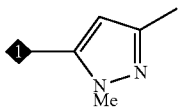
IIc

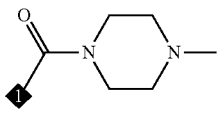
IId

Z in Formula IIa represents CH$_2$, CH=CH, C≡C or a direct bond;

R$_1$ in Formula I represents 4-F or 4-OCF$_3$ or 2-Cl, 4-OCF$_3$ or 3-Cl, 4-OCF$_3$ or 3F, 4-OCF$_3$ or 2-aza, 4-CF$_3$ or 3-aza, 4-CF$_3$ or 2-aza, 4-F;

R$_2$ in Formula IIa represents any one or two of H, F or aza (—CH= replaced by —N=) at any of the available ring positions.

Figure 27:
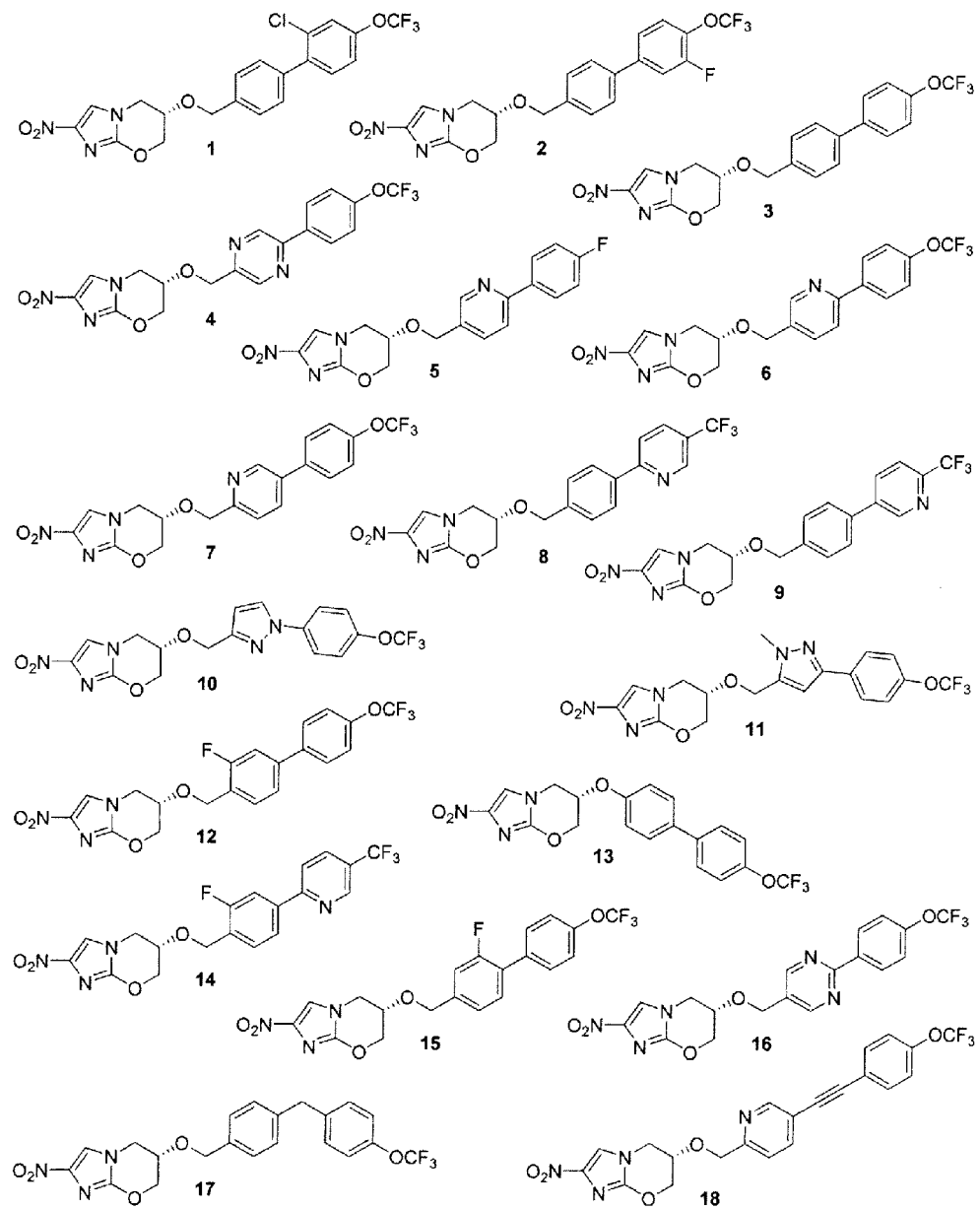
FIG. 27 shows the structures of representative compounds 1-18 referred to in Table 1 and Examples 1-3.
Figure 28:
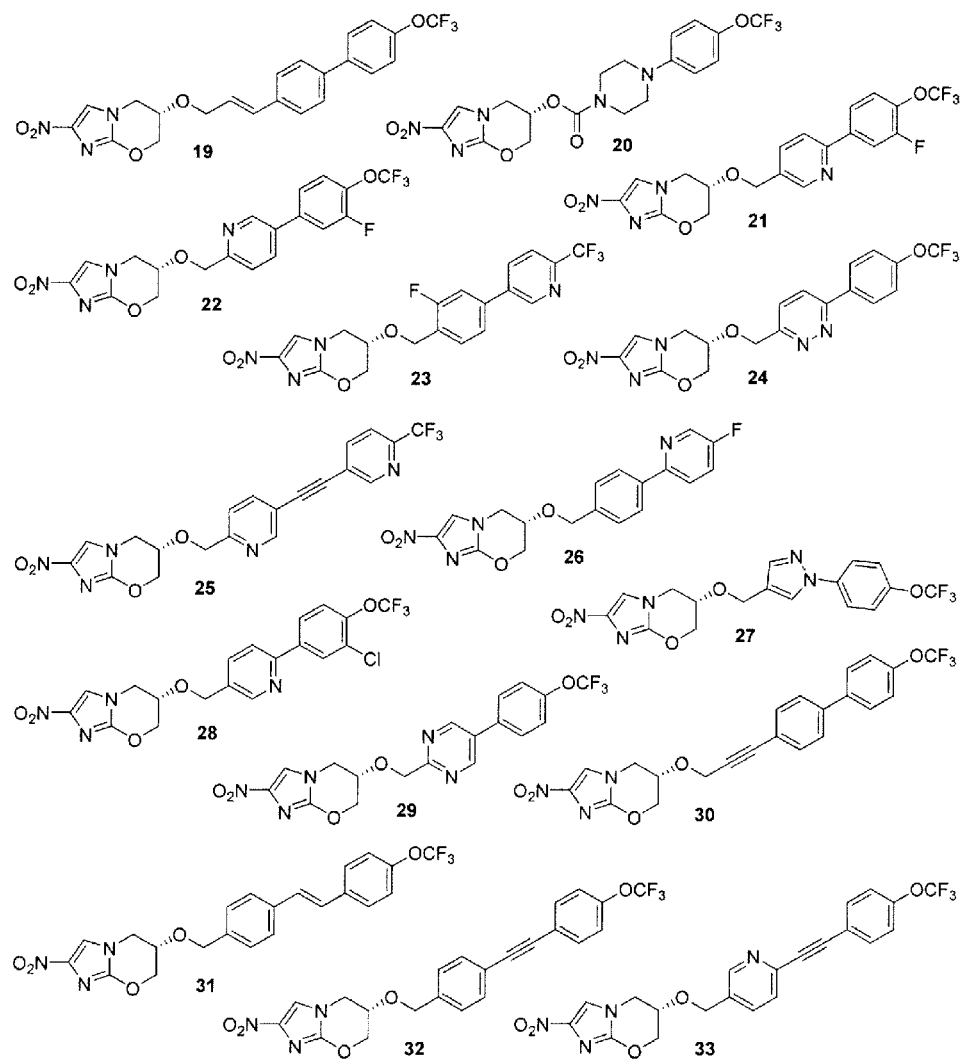
FIG. 28 shows the structures of representative compounds 19-33 referred to in Table 1 and Examples 1-3.

The most highly preferred of the compounds described by Formula I are:
A. (6S)-6-{[2'-Chloro-4'-(trifluoromethoxy)[1,1'-biphenyl]-4-yl]methoxy}-2-nitro-6,7-dihydro-5H-imidazo[2,1-b][1,3]oxazine (compound 1 of Table 1 and FIG. 27);
B. (6S)-6-{[3'-Fluoro-4'-(trifluoromethoxy)[1,1'-biphenyl]-4-yl]methoxy}-2-nitro-6,7-dihydro-5H-imidazo[2,1-b][1,3]oxazine (compound 2 of Table 1 and FIG. 27);
C. (6S)-2-Nitro-6-{[4'-(trifluoromethoxy)[1,1'-biphenyl]-4-yl]methoxy}-6,7-dihydro-5H-imidazo[2,1-b][1,3]oxazine (compound 3 of Table 1 and FIG. 27);
D. (6S)-2-Nitro-6-({5-[4-(trifluoromethoxy)phenyl]-2-pyrazinyl}methoxy)-6,7-dihydro-5H-imidazo[2,1-b][1,3]oxazine (compound 4 of Table 1 and FIG. 27);
E. (6S)-6-{[6-(4-Fluorophenyl)-3-pyridinyl]methoxy}-2-nitro-6,7-dihydro-5H-imidazo[2,1-b][1,3]oxazine (compound 5 of Table 1 and FIG. 27);
F. (6S)-2-Nitro-6-({6-[4-(trifluoromethoxy)phenyl]-3-pyridinyl}methoxy)-6,7-dihydro-5H-imidazo[2,1-b][1,3]oxazine (compound 6 of Table 1 and FIG. 27);
G. (6S)-2-Nitro-6-({5-[4-(trifluoromethoxy)phenyl]-2-pyridinyl}methoxy)-6,7-dihydro-5H-imidazo[2,1-b][1,3]oxazine (compound 7 of Table 1 and FIG. 27);
H. (6S)-2-Nitro-6-({4-[5-(trifluoromethyl)-2-pyridinyl]benzyl}oxy)-6,7-dihydro-5H-imidazo[2,1-b][1,3]oxazine (compound 8 of Table 1 and FIG. 27);
I. (6S)-2-Nitro-6-({4-[6-(trifluoromethyl)-3-pyridinyl]benzyl}oxy)-6,7-dihydro-5H-imidazo[2,1-b][1,3]oxazine (compound 9 of Table 1 and FIG. 27);
J. (6S)-2-Nitro-6-({1-[4-(trifluoromethoxy)phenyl]-1H-pyrazol-3-yl}methoxy)-6,7-dihydro-5H-imidazo[2,1-b][1,3]oxazine (compound 10 of Table 1 and FIG. 27);
K. (6S)-6-({1-Methyl-3-[4-(trifluoromethoxy)phenyl]-1H-pyrazol-5-yl}methoxy)-2-nitro-6,7-dihydro-5H-imidazo[2,1-b][1,3]oxazine (compound 11 of Table 1 and FIG. 27);
L. (6S)-6-{[3-Fluoro-4'-(trifluoromethoxy)[1,1'-biphenyl]-4-yl]methoxy}-2-nitro-6,7-dihydro-5H-imidazo[2,1-b][1,3]oxazine (compound 12 of Table 1 and FIG. 27);
M. (6S)-2-Nitro-6-{[4'-(trifluoromethoxy)[1,1'-biphenyl]-4-yl]oxy}-6,7-dihydro-5H-imidazo[2,1-b][1,3]oxazine (compound 13 of Table 1 and FIG. 27);
N. (6S)-6-({2-Fluoro-4-[5-(trifluoromethyl)-2-pyridinyl]benzyl}oxy)-2-nitro-6,7-dihydro-5H-imidazo[2,1-b][1,3]oxazine (compound 14 of Table 1 and FIG. 27);
O. (6S)-6-{[2-Fluoro-4'-(trifluoromethoxy)[1,1'-biphenyl]-4-yl]methoxy}-2-nitro-6,7-dihydro-5H-imidazo[2,1-b][1,3]oxazine (compound 15 of Table 1 and FIG. 27);
P. (6S)-2-Nitro-6-({2-[4-(trifluoromethoxy)phenyl]-5-pyrimidinyl}methoxy)-6,7-dihydro-5H-imidazo[2,1-b][1,3]oxazine (compound 16 of Table 1 and FIG. 27);
Q. (6S)-2-Nitro-6-({4-[4-(trifluoromethoxy)benzyl]benzyl}oxy)-6,7-dihydro-5H-imidazo[2,1-b][1,3]oxazine (compound 17 of Table 1 and FIG. 27);
R. (6S)-2-Nitro-6-[(5-{[4-(trifluoromethoxy)phenyl]ethynyl}-2-pyridinyl)methoxy]-6,7-dihydro-5H-imidazo[2,1-b][1,3]oxazine (compound 18 of Table 1 and FIG. 27);
S. (6S)-2-Nitro-6-({(2E)-3-[4'-(trifluoromethoxy)[1,1'-biphenyl]-4-yl]-2-propenyl}oxy)-6,7-dihydro-5H-imidazo[2,1-b][1,3]oxazine (compound 19 of Table 1 and FIG. 28);
T. (6S)-2-Nitro-6,7-dihydro-5H-imidazo[2,1-b][1,3]oxazin-6-yl 4-[4-(trifluoromethoxy)phenyl]-1-piperazinecarboxylate (compound 20 of Table 1 and FIG. 28);
U. (6S)-6-({6-[3-Fluoro-4-(trifluoromethoxy)phenyl]-3-pyridinyl}methoxy)-2-nitro-6,7-dihydro-5H-imidazo[2,1-b][1,3]oxazine (compound 21 of Table 1 and FIG. 28);
V. (6S)-6-({5-[3-Fluoro-4-(trifluoromethoxy)phenyl]-2-pyridinyl}methoxy)-2-nitro-6,7-dihydro-5H-imidazo[2,1-b][1,3]oxazine (compound 22 of Table 1 and FIG. 28);
W. (6S)-6-({2-Fluoro-4-[6-(trifluoromethyl)-3-pyridinyl]benzyl}oxy)-2-nitro-6,7-dihydro-5H-imidazo[2,1-b][1,3]oxazine (compound 23 of Table 1 and FIG. 28);
X. (6S)-2-Nitro-6-({6-[4-(trifluoromethoxy)phenyl]-3-pyridazinyl}methoxy)-6,7-dihydro-5H-imidazo[2,1-b][1,3]oxazine (compound 24 of Table 1 and FIG. 28);
Y. (6S)-2-Nitro-6-[(5-{[6-(trifluoromethyl)-3-pyridinyl]ethynyl}-2-pyridinyl)methoxy]-6,7-dihydro-5H-imidazo[2,1-b][1,3]oxazine (compound 25 of Table 1 and FIG. 28);
Z. (6S)-6-{[4-(5-Fluoro-2-pyridinyl)benzyl]oxy}-2-nitro-6,7-dihydro-5H-imidazo[2,1-b][1,3]oxazine (compound 26 of Table 1 and FIG. 28);

AA. (6S)-2-Nitro-6-({1-[4-(trifluoromethoxy)phenyl]-1H-pyrazol-4-yl}methoxy)-6,7-dihydro-5H-imidazo[2,1-b][1,3]oxazine (compound 27 of Table 1 and FIG. 28);

BB. (6S)-6-({6-[3-Chloro-4-(trifluoromethoxy)phenyl]-3-pyridinyl}methoxy)-2-nitro-6,7-dihydro-5H-imidazo[2,1-b][1,3]oxazine (compound 28 of Table 1 and FIG. 28);

CC. (6S)-2-Nitro-6-({5-[4-(trifluoromethoxy)phenyl]-2-pyrimidinyl}methoxy)-6,7-dihydro-5H-imidazo[2,1-b][1,3]oxazine (compound 29 of Table 1 and FIG. 28);

DD. (6S)-2-Nitro-6-({3-[4'-(trifluoromethoxy)[1,1'-biphenyl]-4-yl]-2-propynyl}oxy)-6,7-dihydro-5H-imidazo[2,1-b][1,3]oxazine (compound 30 of Table 1 and FIG. 28);

EE. (6S)-2-Nitro-6-[(4-{(E)-2-[4-(trifluoromethoxy)phenyl]ethenyl}benzyl)oxy]-6,7-dihydro-5H-imidazo[2,1-b][1,3]oxazine (compound 31 of Table 1 and FIG. 28);

FF. (6S)-2-Nitro-6-[(4-{[4-(trifluoromethoxy)phenyl]ethynyl}benzyl)oxy]-6,7-dihydro-5H-imidazo[2,1-b][1,3]oxazine (compound 32 of Table 1 and FIG. 28); and GG. (6S)-2-Nitro-6-[(6-{[4-(trifluoromethoxy)phenyl]ethynyl}-3-pyridinyl)methoxy]-6,7-dihydro-5H-imidazo[2,1-b][1,3]oxazine (compound 33 of Table 1 and FIG. 28).

Compounds of Formula I may occur in different geometric and enantiomeric forms, and both pure forms and mixtures of these separate isomers are included in the scope of this invention, as well as any physiologically functional or pharmacologically acceptable salt derivatives or prodrugs thereof. Production of these alternate forms would be well within the capabilities of one skilled in the art.

The current invention also pertains to methods of prevention or therapy for microbial infections, such as *Mycobacterium tuberculosis*, including the step of administering a compound of Formula I.

In another aspect of the present invention there is provided a pharmaceutical composition including a therapeutically effective amount of a compound of Formula I as defined above and a pharmaceutically acceptable excipient, adjuvant, carrier, buffer or stabiliser. A "therapeutically effective amount" is to be understood as an amount of a compound of Formula I that is sufficient to show anti-bacterial or anti-microbial effects. The actual amount, rate and time-course of administration will depend on the nature and severity of the disease being treated. Prescription of treatment is within the responsibility of general practitioners and other medical doctors. The pharmaceutically acceptable excipient, adjuvant, carrier, buffer or stabiliser should be non-toxic and should not interfere with the efficacy of the active ingredient. The precise nature of the carrier or other material will depend on the route of administration, which may be oral, or by injection, such as cutaneous, subcutaneous, or intravenous injection, or by dry powder inhaler.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such as gelatin. For intravenous, cutaneous or subcutaneous injection, the active ingredient will be in the form of a parenterally acceptable aqueous solution which is pyrogen-free and has a suitable pH, isotonicity and stability. Those of relevant skill in the art are well able to prepare suitable solutions using, for example, isotonic vehicles such as Sodium Chloride injection, Ringer's injection, Lactated Ringer's injection. Preservatives, stabilisers, buffers, antioxidants and/or other additives may be included as required.

The pharmaceutical composition can further comprise one or more additional anti-infective treatments. These anti-infective treatments can be any suitable treatment available commercially or from other sources that are known to effectively prevent or treat microbial infections, such as *Mycobacterium tuberculosis*.

In another aspect, there is provided the use in the manufacture of a medicament of a therapeutically effective amount of a compound of Formula I as defined above for administration to a subject. There is also provided a method of making a compound of Formula I.

The term "pharmacologically acceptable salt" used throughout the specification is to be taken as meaning any acid or base derived salt formed from hydrochloric, sulfuric, phosphoric, acetic, citric, oxalic, malonic, salicylic, malic, fumaric, succinic, ascorbic, maleic, methanesulfonic, isoethionic acids and the like, and potassium carbonate, sodium or potassium hydroxide, ammonia, triethylamine, triethanolamine and the like.

The term "prodrug" means a pharmacological substance that is administered in an inactive, or significantly less active, form. Once administered, the prodrug is metabolised in vivo into an active metabolite.

The term "therapeutically effective amount" means a non-toxic but sufficient amount of the drug to provide the desired therapeutic effect. The amount that is "effective" will vary from subject to subject, depending on the age and general condition of the individual, the particular concentration and composition being administered, and the like. Thus, it is not always possible to specify an exact effective amount. However, an appropriate effective amount in any individual case may be determined by one of ordinary skill in the art using routine experimentation. Furthermore, the effective amount is the concentration that is within a range sufficient to permit ready application of the formulation so as to deliver an amount of the drug that is within a therapeutically effective range.

The term "aza" means —CH= replaced by —N= within the compound. The term "diaza" means —CH=CH— replaced by —N=N—, —CH=CH—CH= replaced by —N=CH—N=, or —CH=CH—CH=CH— replaced by —N=CH—CH=N— within the compound.

Further aspects of the present invention will become apparent from the following description given by way of example only and with reference to the accompanying synthetic schemes.

EXAMPLE 1

General Synthetic Schemes

The compounds can be prepared by the general methods outlined in Schemes 1-24, shown in FIGS. 3-26, or by any other suitable method. In the description of Schemes 1-24 below, reference is made to representative compounds shown in Table 1 below and in FIGS. 2 and 27-28.

TABLE 1

Representative Compounds

Figure 1:
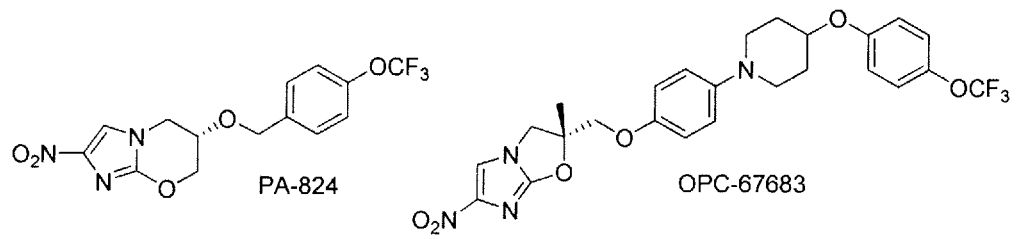
FIG. 1 shows the structures of compounds PA-824 and OPC-67683.
Figure 2:
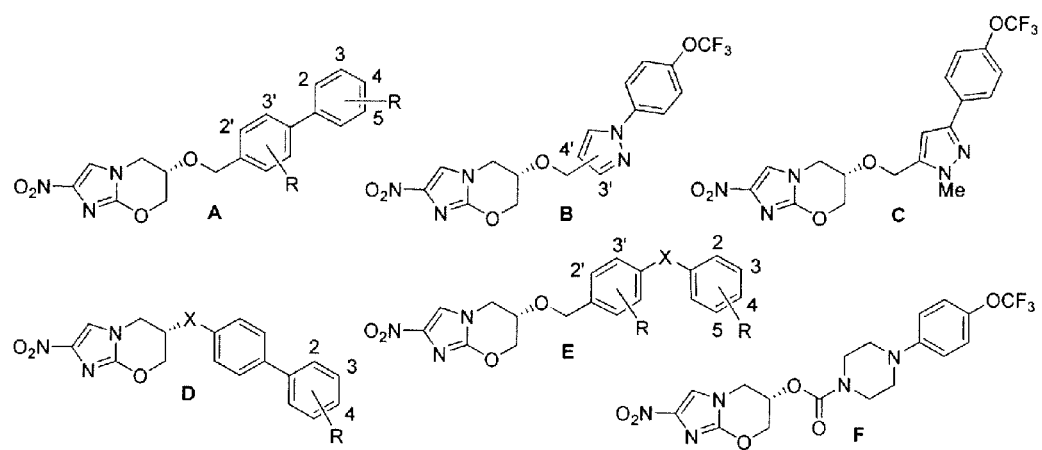
FIG. 2 shows the general structures of representative compounds referred to in Table 1.

| No | FIG. 2 Struct | R | Formula | Mp (° C.) | Analysis |
|---|---|---|---|---|---|
| 1 | A | 2-Cl, 4-OCF$_3$ | C$_{20}$H$_{15}$ClF$_3$N$_3$O$_5$ | 80-82 | C, H, N |
| 2 | A | 3-F, 4-OCF$_3$ | C$_{20}$H$_{15}$F$_4$N$_3$O$_5$ | 169-171 | C, H, N |
| 3 | A | 4-OCF$_3$ | C$_{20}$H$_{16}$F$_3$N$_3$O$_5$ | 199-201 | C, H, N |
| 4 | A | 2',5'-diaza, 4-OCF$_3$ | C$_{18}$H$_{14}$F$_3$N$_5$O$_5$ | 182-184 | C, H, N |
| 5 | A | 3'-aza, 4-F | C$_{18}$H$_{15}$FN$_4$O$_4$·1.5H$_2$O | 194-196 | C, N, F |
| 6 | A | 3'-aza, 4-OCF$_3$ | C$_{19}$H$_{15}$F$_3$N$_4$O$_5$ | 217-219 | C, H, N |
| 7 | A | 2'-aza, 4-OCF$_3$ | C$_{19}$H$_{15}$F$_3$N$_4$O$_5$ | 157-159 | C, H, N, F |
| 8 | A | 2-aza, 4-CF$_3$ | C$_{19}$H$_{15}$F$_3$N$_4$O$_4$ | 252-254 | C, H, N |
| 9 | A | 3-aza, 4-CF$_3$ | C$_{19}$H$_{15}$F$_3$N$_4$O$_4$ | 221-222 | C, H, N |
| 10 | B | 3'-attachment | C$_{17}$H$_{14}$F$_3$N$_5$O$_5$ | 103-105 | C, H, N |
| 11 | C | | C$_{18}$H$_{16}$F$_3$N$_5$O$_5$ | 178-179 | C, H, N |
| 12 | A | 2'-F, 4-OCF$_3$ | C$_{20}$H$_{15}$F$_4$N$_3$O$_5$ | 160-162 | C, H, N |
| 13 | D | 4-OCF$_3$: X = O | C$_{19}$H$_{14}$F$_3$N$_3$O$_5$ | 210 | C, H, N |
| 14 | A | 2'-F, 2-aza, 4-CF$_3$ | C$_{19}$H$_{14}$F$_4$N$_4$O$_4$ | 233-235 | C, H, N |
| 15 | A | 3'-F, 4-OCF$_3$ | C$_{20}$H$_{15}$F$_4$N$_3$O$_5$ | 181-183 | C, H, N |
| 16 | A | 3',5'-diaza, 4-OCF$_3$ | C$_{18}$H$_{14}$F$_3$N$_5$O$_5$ | 227-230 | C, H, N |
| 17 | E | 4-OCF$_3$: X = CH$_2$ | C$_{21}$H$_{18}$F$_3$N$_3$O$_5$ | 132-133 | C, H, N |
| 18 | E | 2'-aza, 4-OCF$_3$: X = C≡C | C$_{21}$H$_{15}$F$_3$N$_4$O$_5$ | 207-208 | C, H, N |
| 19 | D | 4-OCF$_3$: X = OCH$_2$CH=CH | C$_{22}$H$_{18}$F$_3$N$_3$O$_5$ | 220-221 | C, H, N |
| 20 | F | | C$_{18}$H$_{18}$F$_3$N$_5$O$_6$ | 166-168 | C, H, N |
| 21 | A | 3'-aza, 3-F, 4-OCF$_3$ | C$_{19}$H$_{14}$F$_4$N$_4$O$_5$ | 187-189 | C, H, N |
| 22 | A | 2'-aza, 3-F, 4-OCF$_3$ | C$_{19}$H$_{14}$F$_4$N$_4$O$_5$ | 182-184 | C, H, N |
| 23 | A | 2'-F, 3-aza, 4-CF$_3$ | C$_{19}$H$_{14}$F$_4$N$_4$O$_4$ | 195-198 | C, H, N |
| 24 | A | 2',3'-diaza, 4-OCF$_3$ | C$_{18}$H$_{14}$F$_3$N$_5$O$_5$ | 194 (dec) | C, H, N |
| 25 | E | 2',3-diaza, 4-CF$_3$: X = C≡C | C$_{20}$H$_{14}$F$_3$N$_5$O$_4$ | 226-227 | C, H, N |
| 26 | A | 2-aza, 4-F | C$_{18}$H$_{15}$FN$_4$O$_4$ | 180-181 | C, H, N |
| 27 | B | 4'-attachment | C$_{17}$H$_{14}$F$_3$N$_5$O$_5$ | 150-151 | C, H, N |
| 28 | A | 3'-aza, 3-Cl, 4-OCF$_3$ | C$_{19}$H$_{14}$ClF$_3$N$_4$O$_5$ | 169-171 | C, H, N |
| 29 | A | 2',6'-diaza, 4-OCF$_3$ | C$_{18}$H$_{14}$F$_3$N$_5$O$_5$ | 223-226 | C, H, N |
| 30 | D | 4-OCF$_3$: X = OCH$_2$C≡C | C$_{22}$H$_{16}$F$_3$N$_3$O$_5$ | 192-194 | C, H, N |
| 31 | E | 4-OCF$_3$: X = C≡C | C$_{22}$H$_{18}$F$_3$N$_3$O$_5$ | 228-230 | C, H, N |
| 32 | E | 4-OCF$_3$: X = C≡C | C$_{22}$H$_{16}$F$_3$N$_3$O$_5$ | 233-236 | C, H, N |
| 33 | E | 3'-aza, 4-OCF$_3$: X = C≡C | C$_{21}$H$_{15}$F$_3$N$_4$O$_5$ | 235-238 | C, H, N |

Figure 3:
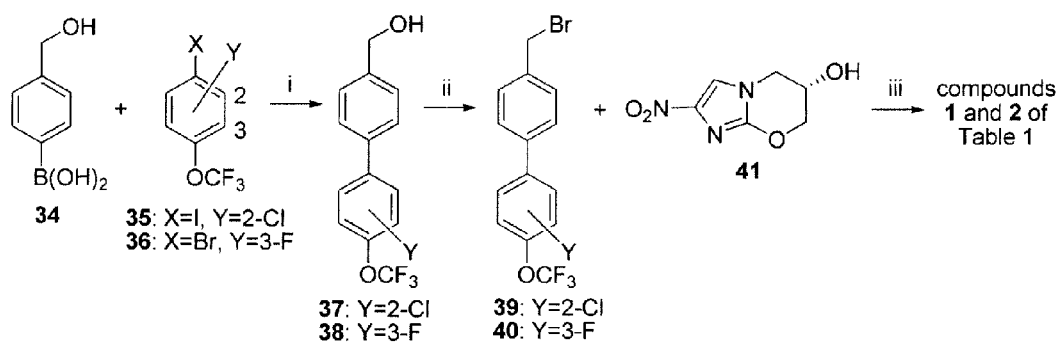
FIG. 3 shows a general synthetic scheme for preparing representative compounds.

In Scheme 1, shown in FIG. 3, reagents and conditions were (i) 2M Na$_2$CO$_3$, toluene, EtOH, Pd(dppf)Cl$_2$ under N$_2$, 88° C., 1-2.5 h; (ii) 30% HBr/AcOH, 20° C., 6-11 h; (iii) DMF, 0-20° C., 3 h. Suzuki couplings of 4-(hydroxymethyl) phenylboronic acid (34) with halides 35 and 36 in the presence of Pd(dppf)Cl$_2$ gave the biphenyl alcohols 37 and 38, which were converted to the corresponding bromomethyl compounds 39 and 40. Coupling of these with the known alcohol 41 (reported in U.S. Pat. No. 5,668,127 via 4 steps, starting from 2,4-dinitroimidazole and tert-butyldimethylsilyl (S)-glycidyl ether) gave the desired compounds 1 and 2 of Table 1.

Figure 4:
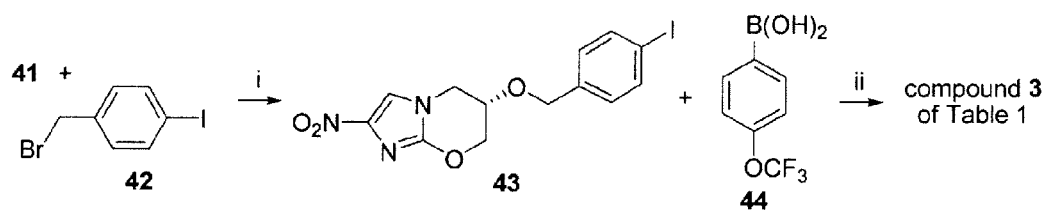
FIG. 4 shows a general synthetic scheme for preparing representative compounds.

In Scheme 2, shown in FIG. 4, reagents and conditions were (i) NaH, DMF, 5-20° C., 2 h; (ii) 2M K$_2$CO$_3$, toluene, EtOH, Pd(dppf)Cl$_2$ under N$_2$, reflux, 30 min. Similar NaH-assisted coupling of alcohol 41 with 4-iodobenzyl bromide (42) gave the known 4-iodobenzyl ether 43 (reported in U.S. Pat. No. 6,087,358 via the same procedure), which underwent Suzuki coupling as in Scheme 1 with 4-(trifluoromethoxy) phenylboronic acid (44) to give compound 3 of Table 1.

Figure 5:
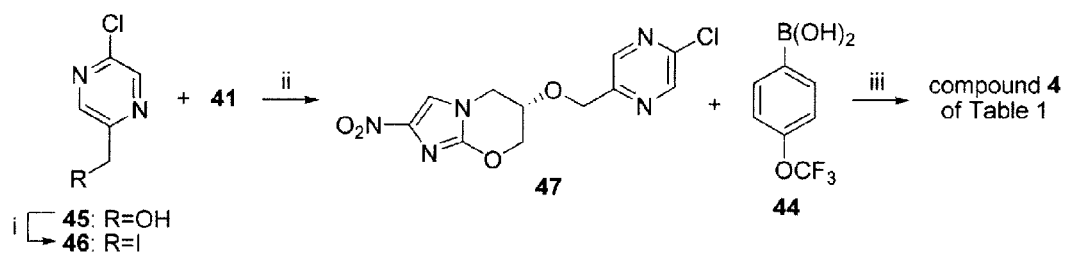
FIG. 5 shows a general synthetic scheme for preparing representative compounds.

In Scheme 3, shown in FIG. 5, reagents and conditions were (i) MsCl, Et$_3$N, THF, 0° C., 30 min, then NaI, acetone, reflux, 1 h; (ii) NaH, DMF, −78 to 0° C., 1 h; (iii) 2M K$_2$CO$_3$, toluene, EtOH, Pd(dppf)Cl$_2$ under N$_2$, reflux, 30 min. NaH-assisted coupling of alcohol 41 with 2-chloro-5-(iodomethyl) pyrazine (46) (prepared from the known (5-chloro-2-pyrazinyl)methanol (45) (obtained by chlorination and reduction of 5-hydroxypyrazine-2-carboxylic acid, as reported by Kiener et al., 1994) by reaction with MsCl followed by NaI) gave chloride 47. This underwent Suzuki coupling with 4-(trifluoromethoxy)phenylboronic acid (44) to give compound 4 of Table 1.

Figure 6:
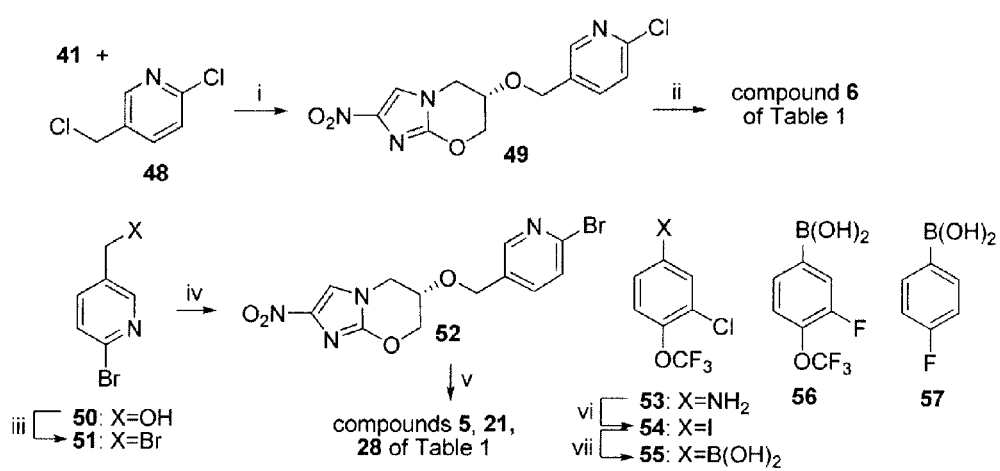
FIG. 6 shows a general synthetic scheme for preparing representative compounds.

In Scheme 4, shown in FIG. 6, reagents and conditions were: (i) NaH, DMF, 5-20° C., 16 h; (ii) 44, 2M K$_2$CO$_3$, DME, Pd(dppf)Cl$_2$ under N$_2$, 90° C., 2 days; (iii) NBS, PPh$_3$, CH$_2$Cl$_2$, 20° C., 3.5 h; (iv) 41, NaH, DMF, 0-20° C., 2.5 h; (v) 55-57, 2M Na$_2$CO$_3$, toluene, EtOH, Pd(dppf)Cl$_2$ under N$_2$, 90° C., 20-120 min; (vi) aq NaNO$_2$, 25% H$_2$SO$_4$, 0° C., 12 min, then aq KI, 20° C., 10 min, then 52° C., 2 h; (vii) n-BuLi, B(OiPr)$_3$, toluene, THF, −78 to −20° C., 5 h, then 2N HCl. NaH-assisted coupling of 2-chloro-5-(chloromethyl)pyridine 48 with alcohol 41 gave the chloride 49, which was Suzuki coupled with 4-(trifluoromethoxy)phenylboronic acid (44) to give compound 6 of Table 1. Bromination of commercial (6-bromo-3-pyridinyl)methanol (50) with NBS/PPh$_3$ gave the bromomethylpyridine 51, which was similarly NaH-coupled with alcohol 41 to give bromide 52. This was Suzuki coupled with boronic acids 55 (obtained from aniline 53 via the novel iodide 54), 56 or 57 to give respectively compounds 28, 21 and 5 of Table 1.

Figure 7:
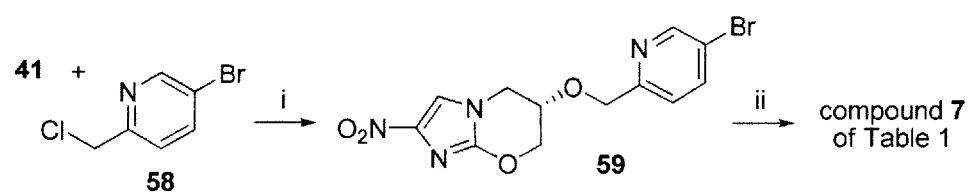
FIG. 7 shows a general synthetic scheme for preparing representative compounds.

In Scheme 5, shown in FIG. 7, reagents and conditions were: (i) NaH, DMF, 5-20° C., 2 h; (ii) 44, 2M K$_2$CO$_3$, toluene, EtOH, Pd(dppf)Cl$_2$ under N$_2$, 90° C., 30 min. NaH-assisted coupling of 5-bromo-2-(chloromethyl)pyridine (58) (prepared by chlorination of (5-bromo-2-pyridinyl)methanol, as reported by van den Heuvel et al., 2004) with alcohol 41 gave the bromide 59, which was Suzuki coupled with 4-(trifluoromethoxy)phenylboronic acid (44) to give compound 7 of Table 1.

Figure 8:
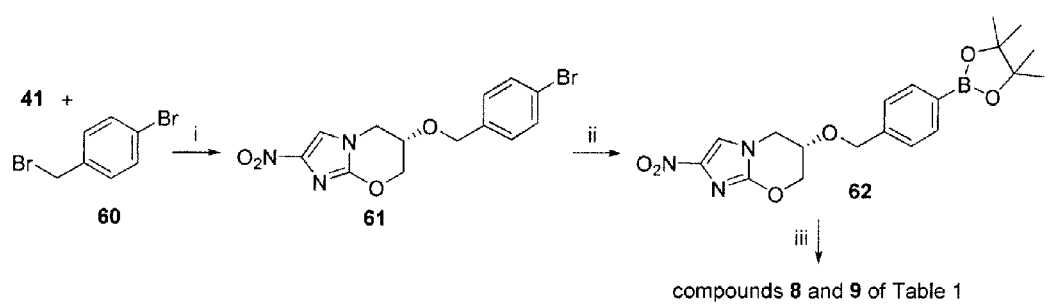
FIG. 8 shows a general synthetic scheme for preparing representative compounds.

In Scheme 6, shown in FIG. 8, reagents and conditions were: (i) NaH, DMF, 20° C., 1 h; (ii) bis(pinacolato)diboron, Pd(dppf)Cl$_2$ under N$_2$, KOAc, DMSO, 90° C., 1 h; (iii) 2-chloro-5-(trifluoromethyl)pyridine or 5-bromo-2-(trifluoromethyl)pyridine, 2M K$_2$CO$_3$, toluene, EtOH, Pd(dppf)Cl$_2$ under N$_2$, reflux, 30 min. The bromide 61 was prepared by NaH-assisted coupling of alcohol 41 with 4-bromobenzyl bromide (60). Reaction of 61 with bis(pinacolato)diboron gave the 4-boronate ester 62, which underwent Suzuki coupling with 2-chloro-5-(trifluoromethyl)pyridine or 5-bromo-2-(trifluoromethyl)pyridine to give respectively compounds 8 and 9 of Table 1.

Figure 9:
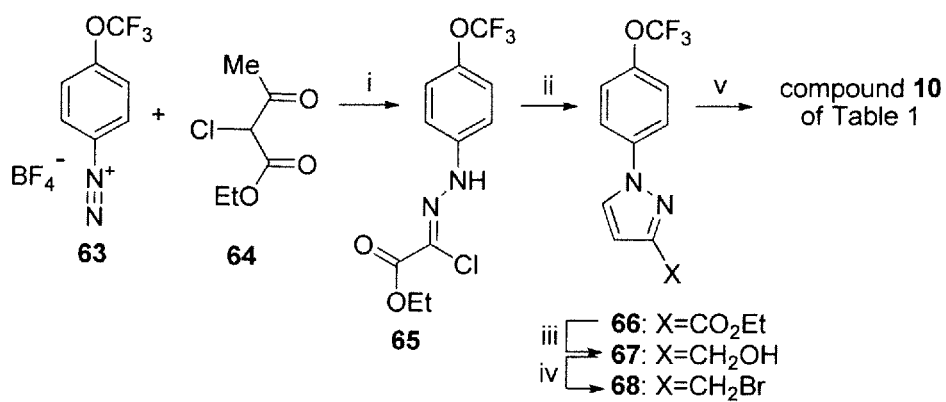
FIG. 9 shows a general synthetic scheme for preparing representative compounds.

In Scheme 7, shown in FIG. 9, reagents and conditions were: (i) Aqueous pyridine, −5° C., 30 min; (ii) bicyclo[2.2.1]hepta-2,5-diene, Et$_3$N, toluene, 70° C., 1 h, then xylene, reflux, 2 h; (iii) LiAlH$_4$, Et$_2$O, 0-20° C., 1 h; (iv) PBr$_3$, Et$_2$O, 20° C., 17 h; (v) 41, NaH, DMF, 0° C., 2 h. Ethyl (2Z)-chloro{[4-(trifluoromethoxy)phenyl]hydrazono}ethanoate (65) [from 4-(trifluoromethoxy)benzenediazonium tetrafluoroborate (63) and ethyl 2-chloroacetoacetate (64)] was reacted with bicyclo[2.2.1]hepta-2,5-diene to give the carboxylate 66. This was reduced (LiAlH$_4$) to alcohol 67, which was then brominated with PBr$_3$ to give bromide 68. NaH-assisted coupling with alcohol 41 then gave compound 10 of Table 1.

Figure 10:
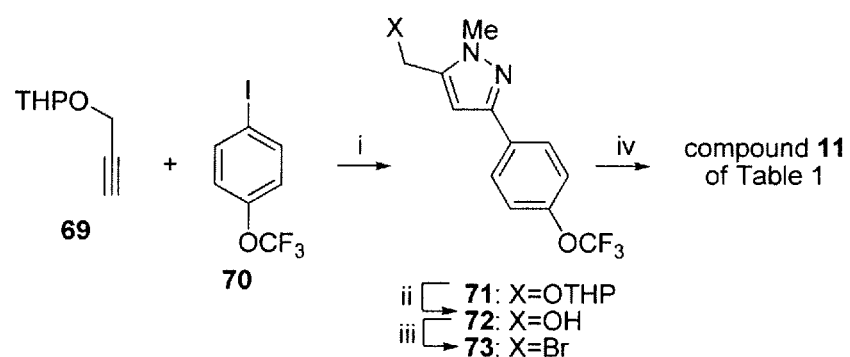
FIG. 10 shows a general synthetic scheme for preparing representative compounds.

In Scheme 8, shown in FIG. 10, reagents and conditions were: (i) CuI, PdCl$_2$(PPh$_3$)$_2$, methylhydrazine sulfate, aqueous NaHCO$_3$, THF, 20° C., 2 days in CO atmosphere; (ii) 4N HCl, THF, 80° C., 16 h; (iii) PBr$_3$, Et$_2$O, 0-20° C., 16 h; (iv) 41, NaH, DMF, 0° C., 2 h. Pyrazole 71 was prepared by the reaction of 2-(2-propynyloxy)tetrahydro-2H-pyran (69), 1-iodo-4-(trifluoromethoxy)benzene (70) and methylhydrazine in the presence of CuI and PdCl$_2$(PPh$_3$)$_2$ and an atmosphere of CO. Hydrolysis of THP ether 71 to alcohol 72, followed by bromination with PBr$_3$, gave bromide 73, which underwent NaH-assisted coupling with alcohol 41 to give compound 11 of Table 1.

Figure 11:
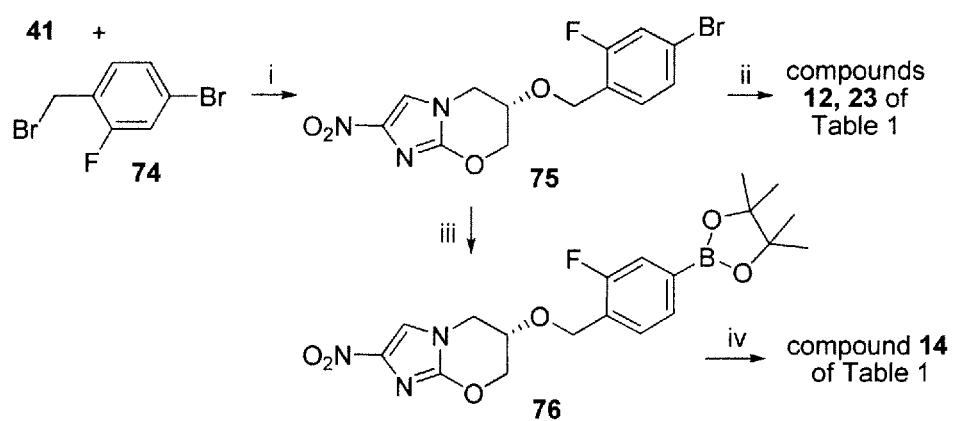
FIG. 11 shows a general synthetic scheme for preparing representative compounds.

In Scheme 9, shown in FIG. 11, reagents and conditions were: (i) NaH, DMF, 0-20° C., 3 h; (ii) ArB(OH)$_2$, 2M Na$_2$CO$_3$, toluene, EtOH, Pd(dppt)Cl$_2$ under N$_2$, 85-90° C., 1-3 h; (iii) bis(pinacolato)diboron, Pd(dppf)Cl$_2$ under N$_2$, KOAc, DMSO, 89° C., 5 h; (iv) 2-chloro-5-(trifluoromethyl)pyridine, 2M Na$_2$CO$_3$, toluene, EtOH, Pd(dppf)Cl$_2$ under N$_2$, 90° C., 120 min. NaH-assisted coupling of 4-bromo-2-fluorobenzyl bromide (74) with alcohol 41 gave the bromide 75, which was Suzuki coupled with the appropriate arylboronic acids to give compounds 12 and 23 of Table 1. Reaction of bromide 75 with bis(pinacolato)diboron gave the boronate ester 76, which underwent Suzuki coupling with 2-chloro-5-(trifluoromethyl)pyridine to give compound 14 of Table 1.

Figure 12:
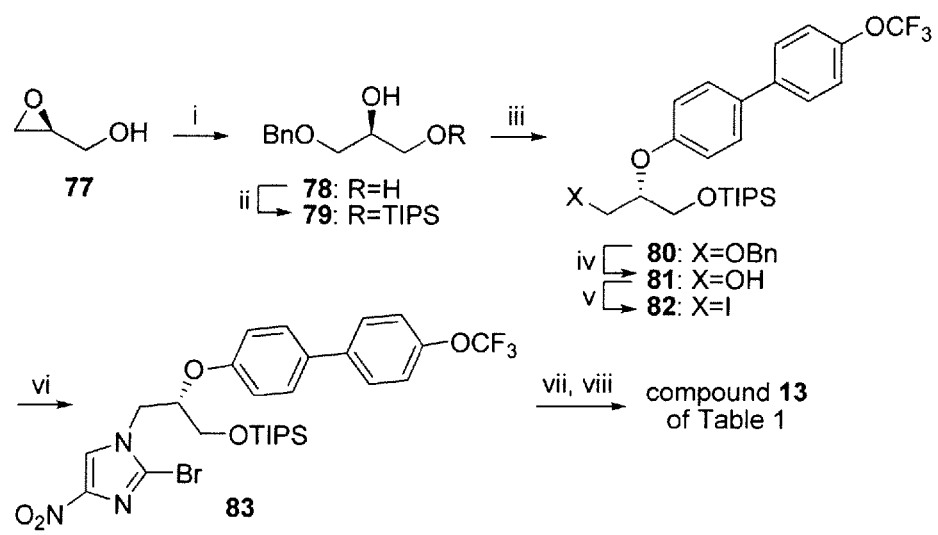
FIG. 12 shows a general synthetic scheme for preparing representative compounds.

In Scheme 10, shown in FIG. 12, reagents and conditions were: (i) cat. CsF, PhCH$_2$OH, 120° C., 16 h; (ii) TIPSCl, imidazole, DMF, 20° C., 16 h; (iii) 4'-(trifluoromethoxy)[1,1'-biphenyl]-4-ol, DIAD, PPh$_3$, benzene, 5-20° C., 18 h; (iv) H$_2$, 5% Pd—C, EtOAc, EtOH, 60 psi, 4 h; (v) I$_2$, PPh$_3$, imidazole, benzene, 20° C., 1 h; (vi) 2-bromo-4(5)-nitroimidazole, K$_2$CO$_3$, DMF, 87° C., 20 h; (vii) TBAF, THF, 20° C., 1 h; (viii) NaH, DMF, 5-20° C., 30 min. Reaction of (S)-glycidol (77) and benzyl alcohol in the presence of CsF gave diol 78, which was mono-protected with TIPS chloride and the resulting alcohol 79 was Mitsunobu coupled with 4'-(trifluoromethoxy)[1,1'-biphenyl]-4-ol (reported by Edsall et al., 2003, via Suzuki coupling of 4-bromophenol and boronic acid 44) to give ether 80. This was debenzylated by hydrogenolysis, and the resulting alcohol 81 was iodinated with I$_2$/PPh$_3$ to give 82. This was coupled with 2-bromo-4(5)-nitroimidazole, and the resulting compound 83 was desilylated with TBAF and ring closed with NaH to give compound 13 of Table 1.

Figure 13:
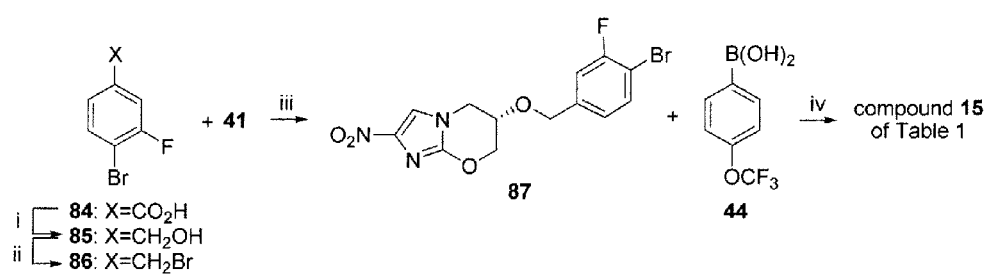
FIG. 13 shows a general synthetic scheme for preparing representative compounds.

In Scheme 11, shown in FIG. 13, reagents and conditions were: (i) NaBH$_4$, I$_2$, THF, 0-20° C., 14 h; (ii) 30% HBr/AcOH, 20° C., 20 h; (iii) NaH, DMF, 0-20° C., 3.5 h; (iv) 2M Na$_2$CO$_3$, toluene, EtOH, Pd(dppf)Cl$_2$ under N$_2$, 90° C., 6 h. NaH-assisted coupling of 4-bromo-3-fluorobenzyl bromide (86) (prepared from the acid 84 via the known alcohol 85 (reported by deSolms et al., 2003, via borane reduction of 84) with oxazine alcohol 41 gave the bromide 87, which underwent Suzuki coupling with 4-(trifluoromethoxy)phenylboronic acid (44) to give compound 15 of Table 1.

Figure 14:
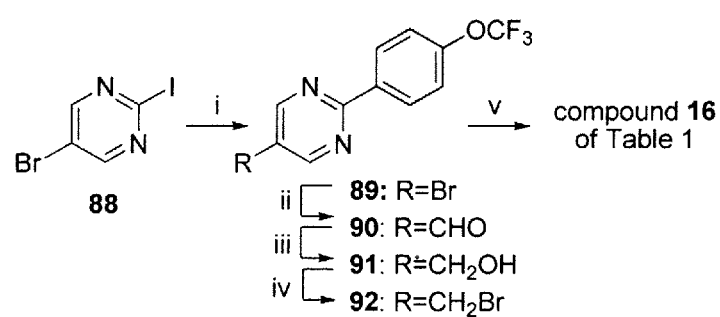
FIG. 14 shows a general synthetic scheme for preparing representative compounds.

In Scheme 12, shown in FIG. 14, reagents and conditions were: (i) 44, aqueous Na$_2$CO$_3$, toluene, EtOH, Pd(PPh$_3$)$_4$ under N$_2$, reflux, 18 h; (ii) n-BuLi, THF, −95° C., 0.5 min, then DMF, −90° C., 20 min; (iii) NaBH$_4$, MeOH, 0° C., 1 h; (iv) MsCl, Et$_3$N, THF, 0° C., 1 h, then LiBr, Me$_2$CO, reflux, 1 h; (v) 41, NaH, DMF, −78 to 0° C., 1 h. Suzuki coupling of boronic acid 44 and 2-iodo-5-bromopyrimidine (88) gave the bromide 89, which was treated with n-BuLi and DMF to give the aldehyde 90. This was reduced with NaBH$_4$ to the alcohol 91, which was reacted with MSCl followed by LiBr to give the bromide 92. Coupling of 92 with alcohol 41 gave compound 16 of Table 1.

Figure 15:
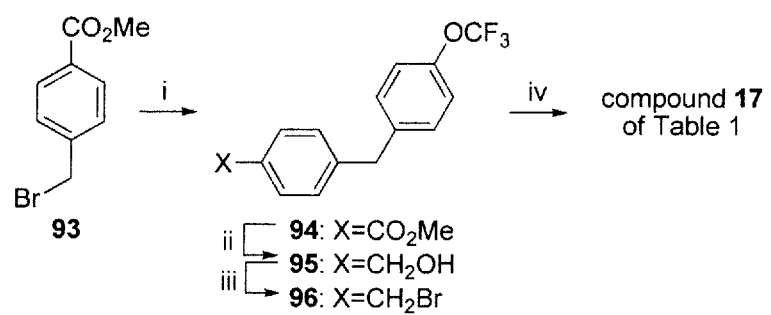
FIG. 15 shows a general synthetic scheme for preparing representative compounds.

In Scheme 13, shown in FIG. 15, reagents and conditions were: (i) 44, 2M K$_2$CO$_3$, DME, Pd(PPh$_3$)$_4$ under N$_2$, 105° C., 24 h; (ii) LiAlH$_4$, Et$_2$O, 20° C., 3 h; (iii) PBr$_3$, CH$_2$Cl$_2$, 20° C., 2 h; (iv) 41, NaH, DMF, 20° C., 3 h. Suzuki coupling of methyl 4-(bromomethyl)benzoate (93) and 4-(trifluoromethoxy)phenylboronic acid (44) gave the methyl benzoate 94. This was reduced with LiAlH$_4$ to the alcohol 95, which gave the bromide 96 on treatment with PBr$_3$. Coupling of this bromide with alcohol 41 then gave compound 17 of Table 1.

Figure 16:
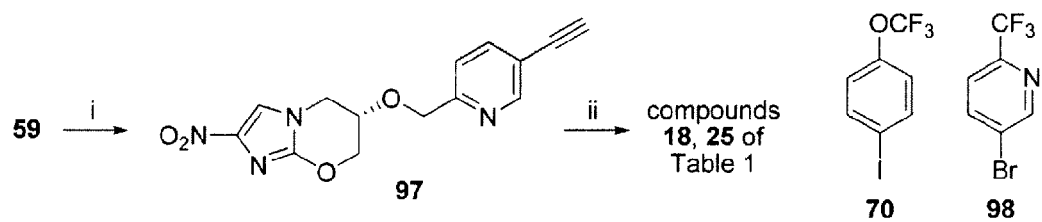
FIG. 16 shows a general synthetic scheme for preparing representative compounds.

In Scheme 14, shown in FIG. 16, reagents and conditions were: (i) HC≡CTMS, Et$_3$N, DMF, CuI, PdCl$_2$(PPh$_3$)$_2$ under N$_2$, 50° C., 18 h, then TBAF, THF, 0-20° C., 2 h; (ii) 70 or 98, Et$_3$N, DMF, CuI, PdCl$_2$(PPh$_3$)$_2$ under N$_2$, 20 or 50° C., 0.5 h. Sonogashira coupling of bromide 59 (see Scheme 5) with ethynylTMS in the presence of Et$_3$N, CuI and PdCl$_2$(PPh$_3$)$_2$, followed by desilylation with TBAF gave the acetylene 97, which was similarly coupled with 1-iodo-4-(trifluoromethoxy)benzene (70) or 5-bromo-2-(trifluoromethyl)pyridine (98) to give respectively compounds 18 and 25 of Table 1.

Figure 17:
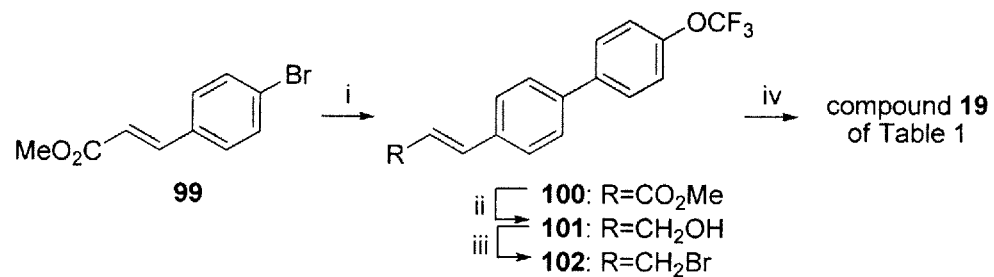
FIG. 17 shows a general synthetic scheme for preparing representative compounds.

In Scheme 15, shown in FIG. 17, reagents and conditions were: (i) 44, dioxane, 2M K$_2$CO$_3$, Pd(dppf)Cl$_2$ under N$_2$, reflux, 1 h; (ii) DIBAL-H, toluene, −78 to 20° C., 1 h; (iii) PBr$_3$, Et$_2$O, 0-20° C., 1 h; (iv) 41, NaH, DMF, −78 to 0° C., 1 h. Bromide 99 was Suzuki coupled to boronic acid 44 (see Scheme 3) to give ester 100, which was reduced with DIBAL-H in toluene to give alcohol 101. Bromination of 101 with PBr$_3$ gave 102, which underwent NaH-assisted coupling with alcohol 41 to give compound 19 of Table 1.

Figure 18:
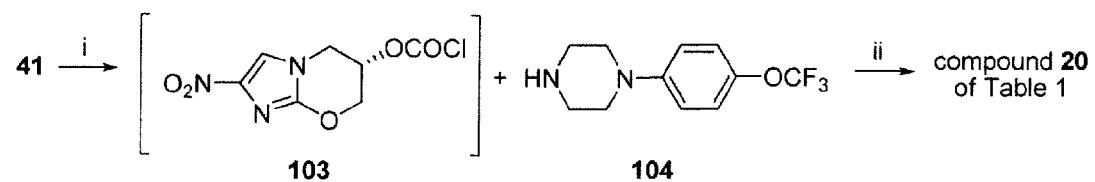
FIG. 18 shows a general synthetic scheme for preparing representative compounds.

In Scheme 16, shown in FIG. 18, reagents and conditions were: (i) Triphosgene, Et$_3$N, 0-20° C., 105 min; (ii) THF, 20° C., 2 h. Alcohol 41 was treated with triphosgene, and the crude carbonyl chloride 103 was reacted directly with 1-[4-(trifluoromethoxy)phenyl]piperazine (104) to give compound 20 of Table 1.

Figure 19:
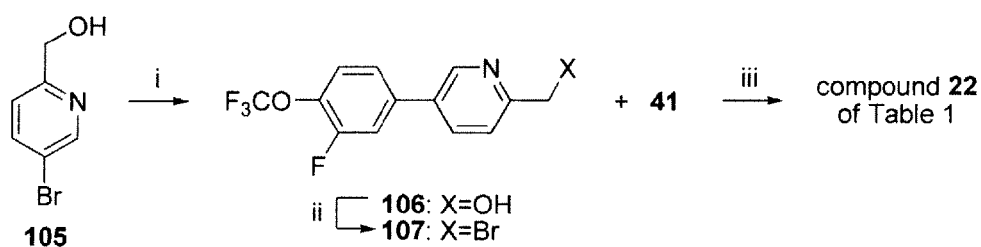
FIG. 19 shows a general synthetic scheme for preparing representative compounds.

In Scheme 17, shown in FIG. 19, reagents and conditions were: (i) 56, 2M Na$_2$CO$_3$, toluene, EtOH, Pd(dppf)Cl$_2$ under N$_2$, 89° C., 2 h; (ii) NBS, PPh$_3$, CH$_2$Cl$_2$, 20° C., 3 h; (iii) NaH, DMF, 0-20° C., 2.5 h. Suzuki coupling of bromide 105 with boronic acid 56 (see Scheme 4) gave alcohol 106, which was brominated with NBS/PPh₃ to give 107. This underwent NaH-assisted coupling with alcohol 41 to give compound 22 of Table 1.

Figure 20:
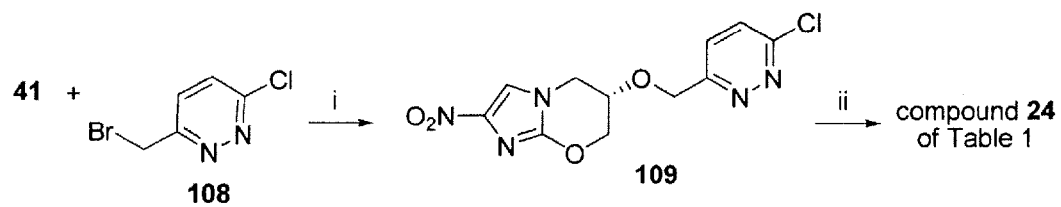
FIG. 20 shows a general synthetic scheme for preparing representative compounds.

In Scheme 18, shown in FIG. 20, reagents and conditions were: (i) NaH, DMF, −42° C., 1 h; (ii) 44, 2M K₂CO₃, toluene, EtOH, Pd(dppf)Cl₂ under N₂, reflux, 0.5 h. Low-temperature reaction of oxazine alcohol 41 and 3-(bromomethyl)-6-chloropyridazine (108) (obtained via free radical bromination of 3-chloro-6-methylpyridazine, as reported by Ohshita J., EP 1555259, 2005) gave the chloride 109, which was Suzuki coupled with boronic acid 44 (see Scheme 3) to give compound 24 of Table 1.

Figure 21:
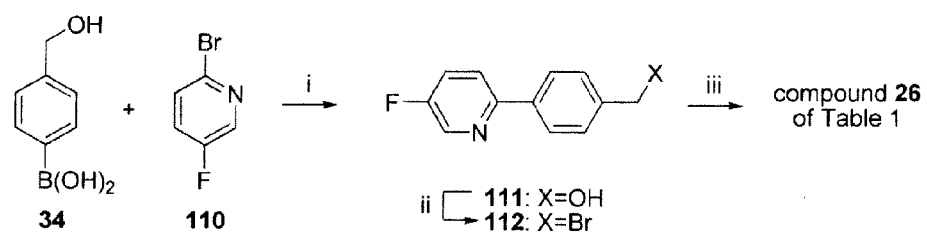
FIG. 21 shows a general synthetic scheme for preparing representative compounds.

In Scheme 19, shown in FIG. 21, reagents and conditions were: (i) 2M Na₂CO₃, toluene, EtOH, Pd(dppf)Cl₂ under N₂, 89° C., 200 min; (ii) NBS, PPh₃, CH₂Cl₂, 20° C., 3 h; (iii) 41, NaH, DMF, 0-20° C., 135 min. Suzuki coupling of bromide 110 with boronic acid 34 gave alcohol 111, which was brominated to 112 and this was then coupled to alcohol 41 to give compound 26 of Table 1.

Figure 22:
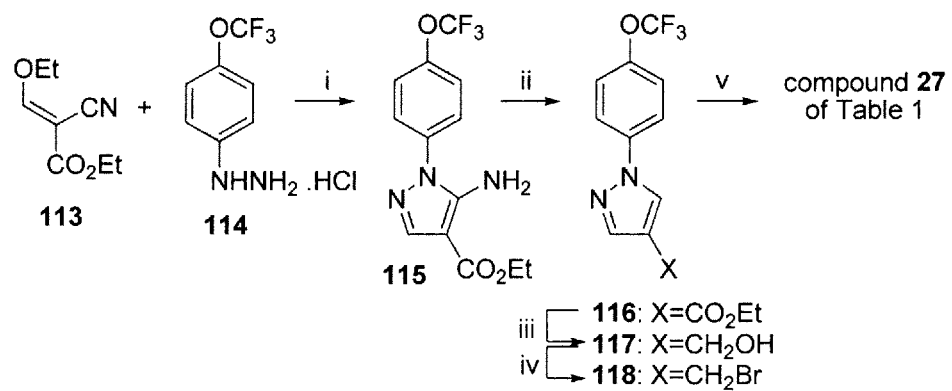
FIG. 22 shows a general synthetic scheme for preparing representative compounds.

In Scheme 20, shown in FIG. 22, reagents and conditions were: (i) aqueous NaOAc, AcOH, 100° C., 15 h; (ii) (CH₃)₂CH(CH₂)₂ONO, THF, reflux, 20 h; (iii) LiAlH₄, Et₂O, reflux, 2 h; (iv) PBr₃, Et₂O, 0° C., 2 h; (v) 41, NaH, DMF, 0° C., 2 h. Reaction of ethyl (2E)-2-cyano-3-ethoxy-2-propenoate 113 and hydrazine 114 gave the pyrazolecarboxylate 115, which was deaminated with isoamyl nitrite. The resulting carboxylate 116 was reduced to the alcohol 117, which was then brominated with PBr₃ to give 118. This underwent NaH-assisted coupling with alcohol 41 to give compound 27 of Table 1.

Figure 23:
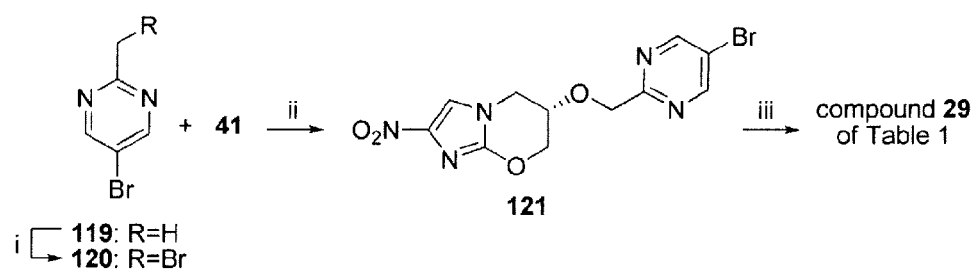
FIG. 23 shows a general synthetic scheme for preparing representative compounds.

In Scheme 21, shown in FIG. 23, reagents and conditions were: (i) NBS, AIBN, CCl₄, 60° C., 3 h; (ii) NaH, DMF, −78 to 0° C., 0.5 h; (iii) 44, 2M K₂CO₃, toluene, EtOH, Pd(dppf)Cl₂ under N₂, reflux, 0.5 h. Bromination of 5-bromo-2-methylpyrimidine (119) gave 120 which underwent NaH-assisted coupling with alcohol 41 to give the bromide 121. Suzuki coupling of 121 with boronic acid 44 (see Scheme 3) gave compound 29 of Table 1.

Figure 24:
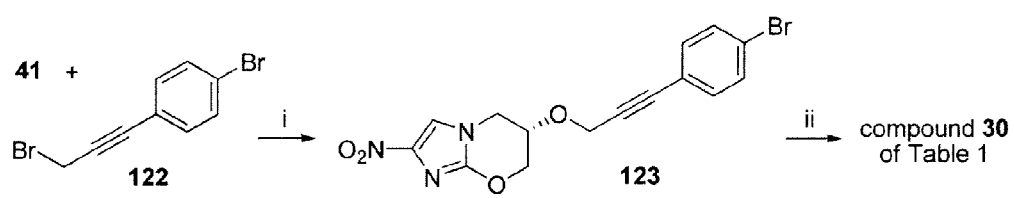
FIG. 24 shows a general synthetic scheme for preparing representative compounds.

In Scheme 22, shown in FIG. 24, reagents and conditions were: (i) NaH, DMF, 0° C., 1 h; (ii) 44, 2M K₂CO₃, toluene, EtOH, Pd(dppf)Cl₂ under N₂, reflux, 0.5 h. NaH-assisted coupling of alcohol 41 and 1-bromo-4-(3-bromo-1-propynyl)benzene (122) (prepared in two steps from 1-bromo-4-iodobenzene and propargyl alcohol, as described in WO 9524400) gave the bromide 123, which was Suzuki coupled with boronic acid 44 to give compound 30 of Table 1.

Figure 25:
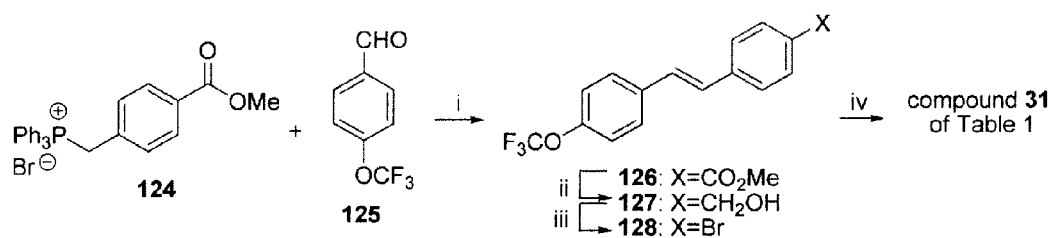
FIG. 25 shows a general synthetic scheme for preparing representative compounds.

In Scheme 23, shown in FIG. 25, reagents and conditions were: (i) K₂CO₃, 18-crown-6, THF, CH₂Cl₂, reflux, 18 h; (ii) LiAlH₄, Et₂O, 0-20° C., 0.5 h; (iii) PBr₃, CH₂Cl₂, 0-20° C., 1 h; (iv) 41, NaH, DMF, −78 to 0° C., 1 h. Wittig reaction of aldehyde 125 and phosphonium salt 124 gave ester 126, which was reduced with reduced with LiAlH₄ to give alcohol 127. Bromination of 127 with PBr₃ gave 128, which underwent NaH-assisted coupling with alcohol 41 to give compound 31 of Table 1.

Figure 26:
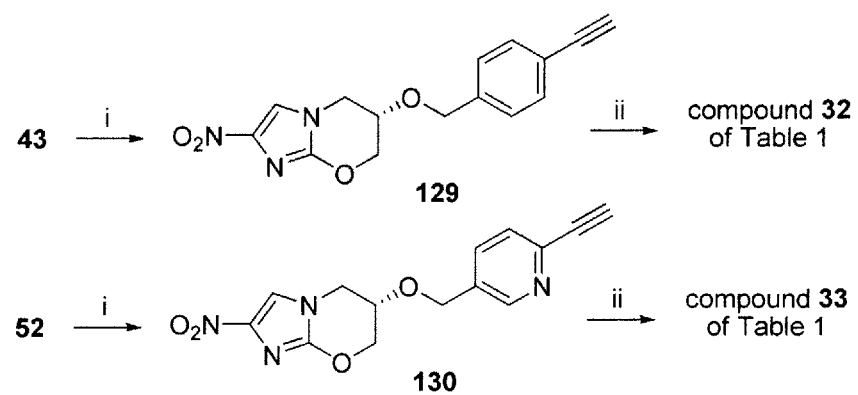
FIG. 26 shows a general synthetic scheme for preparing representative compounds.

In Scheme 24, shown in FIG. 26, reagents and conditions were: (i) HC≡CTMS, Et₃N, DMF, CuI, PdCl₂(PPh₃)₂ under N₂, 20° C., 0.5-18 h, then TBAF, THF, 0-20° C., 2 h; (ii) 70, Et₃N, DMF, CuI, PdCl₂(PPh₃)₂ under N₂, 20° C., 0.5 h. Sonogashira couplings of iodide 43 (see Scheme 2) or bromide 52 (see Scheme 4) with ethynylTMS in the presence of Et₃N, CuI and PdCl₂(PPh₃)₂, followed by desilylation with TBAF, gave the acetylenes 129 or 130, respectively, which were similarly coupled with 1-iodo-4-(trifluoromethoxy)benzene (70) to give compounds 32 and 33 of Table 1.

EXAMPLE 2

Methods of Preparation

A. Synthesis of (6S)-6-[{2'-chloro-4'-(trifluoromethoxy)[1,1'-biphenyl]-4-yl]methoxy}-2-nitro-6,7-dihydro-5H-imidazo[2,1-b][1,3]oxazine (1) by the method of Scheme 1

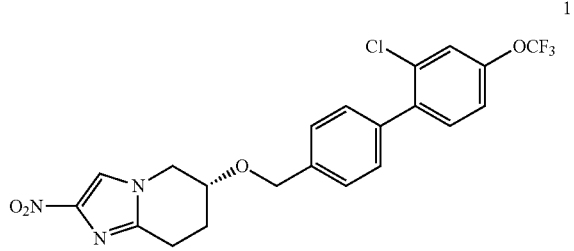 [SMILES: O=[N+]([O-])c1cn2c(n1)CC[C@@H](OCc1ccc(-c3ccc(OC(F)(F)F)cc3Cl)cc1)C2]

A stirred mixture of 4-(hydroxymethyl)phenylboronic acid (34) (308 mg, 2.03 mmol) and Pd(dppf)Cl₂ (191 mg, 0.261 mmol) in toluene (22 mL) and EtOH (11 mL) was degassed for 8 min (vacuum pump) and then N₂ was added. An aqueous solution of 2M Na₂CO₃ (4.4 mL, 8.8 mmol) was added by syringe and the stirred mixture was again degassed for 8 min, and then N₂ was added. 2-Chloro-1-iodo-4-(trifluoromethoxy)benzene (35) (585 mg, 1.81 mmol) was added by syringe and the resulting mixture was stirred at 88° C. for 60 min. The cooled mixture was then diluted with aqueous NaHCO₃ (100 mL) and extracted with CH₂Cl₂ (5×100 mL). The extracts were evaporated to dryness and the residue was chromatographed on silica gel. Elution with 0-50% CH₂Cl₂/petroleum ether firstly gave foreruns, and then further elution with 50% CH₂Cl₂/petroleum ether gave 2'-chloro-4'-(trifluoromethoxy)[1,1'-biphenyl]-4-yl]methanol (37) (537 mg, 98%) as a white solid: mp (pentane) 38-39° C.; ¹H NMR (CDCl₃) δ 7.46 (br d, J=8.2 Hz, 2H), 7.42 (dt, J=8.3, 2.0 Hz, 2H), 7.37 (br s, 1H), 7.36 (d, J=8.5 Hz, 1H), 7.19 (m, 1H), 4.77 (d, J=5.9 Hz, 2H), 1.70 (t, J=5.9 Hz, 1H); HREIMS calcd for C₁₄H₁₀ClF₃O₂ m/z (M⁺) 304.0292, 302.0321, found 304.0294, 302.0317.

HBr in AcOH (5 mL of 33% w/w) was added to a solution of alcohol 37 (618 mg, 2.04 mmol) in glacial AcOH (2.5 mL), and the mixture was stirred at room temperature for 11 h. The resulting orange solution was added slowly to ice-water (50 mL) with stirring, and then the mixture was extracted with pentane (6×50 mL). The extracts were washed with ice-water (50 mL) and then evaporated to give 4-(bromomethyl)-2'-chloro-4'-(trifluoromethoxy)-1,1'-biphenyl (39) (743 mg, 100%) as an oil; ¹H NMR (CDCl₃) δ 7.47 (dt, J=8.3, 1.9 Hz, 2H), 7.39 (dt, J=8.3, 1.9 Hz, 2H), 7.37 (m, 1H), 7.35 (d, J=8.5 Hz, 1H), 7.19 (m, 1H), 4.55 (s, 2H); HREIMS calcd for C₁₄H₉BrClF₃O m/z (M⁺) 367.9427, 365.9457, 363.9477, found 367.9428, 365.9453, 363.9485.

A stirred solution of (6S)-2-nitro-6,7-dihydro-5H-imidazo[2,1-b][1,3]oxazin-6-ol (41) (reported in U.S. Pat. No. 5,668,127 via 4 steps, starting from 2,4-dinitroimidazole and tert-butyldimethylsilyl (S)-glycidyl ether) (342 mg, 1.85 mmol) and bromide 39 (741 mg, 2.03 mmol) in anhydrous DMF (7 mL) under N₂ at 0° C. was treated with 60% NaH (111 mg, 2.78 mmol), then quickly degassed and resealed under N₂.

After stirring at room temperature for 3 h, the reaction was cooled (CO$_2$/acetone), quenched with ice/aqueous NaHCO$_3$ (20 mL), added to brine (80 mL) and extracted with CH$_2$Cl$_2$ (6×80 mL). The combined extracts were evaporated to dryness and the residue was chromatographed on silica gel, eluting with CH$_2$Cl$_2$, to give 1 (694 mg, 80%) as a light yellow solid: mp (CH$_2$Cl$_2$/pentane) 80-82° C.; $^1$H NMR (CDCl$_3$) δ 7.45-7.35 (m, 6H), 7.34 (d, J=8.5 Hz, 1H), 7.20 (m, 1H), 4.79 (d, J=12.0 Hz, 1H), 4.68 (d, J=12.1 Hz, 1H), 4.65 (ddd, J=12.1, 2.9, 2.5 Hz, 1H), 4.37 (br d, J=11.8 Hz, 1H), 4.24-4.12 (m, 3H). Anal. (C$_{20}$H$_{15}$ClF$_3$N$_3$O$_5$) C, H, N.

B. Synthesis of 6S)-6-{[3'-fluoro-4'-(trifluoromethoxy)[1,1'-biphenyl]-4-yl]methoxy}-2-nitro-6,7-dihydro-5H-imidazo[2,1-b][1,3]oxazine (2) by the method of Scheme 1

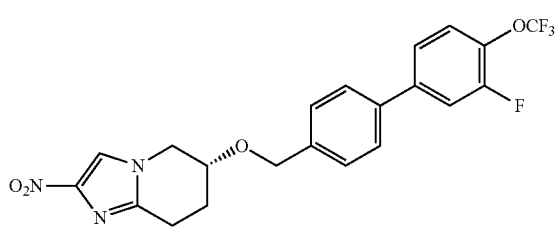

2

Suzuki coupling of 4-(hydroxymethyl)phenylboronic acid (34) and 4-bromo-2-fluoro-1-(trifluoromethoxy)benzene (36) as in Example 2A for 2.5 h, followed by chromatography of the product on silica gel, eluting with 0-40% CH$_2$Cl$_2$/petroleum ether (foreruns) and then 40% CH$_2$Cl$_2$/petroleum ether, gave 3'-fluoro-4'-(trifluoromethoxy)[1,1'-biphenyl]-4-yl]methanol (38) (73%) as a cream solid: mp (CH$_2$Cl$_2$/pentane) 70-71° C.; $^1$H NMR (CDCl$_3$) δ 7.54 (dt, J=8.3, 1.8 Hz, 2H), 7.46 (br d, J=8.2 Hz, 2H), 7.41 (br d, J=11.2 Hz, 1H), 7.40-7.32 (m, 2H), 4.76 (d, J=5.9 Hz, 2H), 1.69 (t, J=5.9 Hz, 1H); HREIMS calcd for C$_{14}$H$_{10}$F$_4$O$_2$ m/z (M$^+$) 286.0617, found 286.0616.

Bromination of alcohol 38 as in Example 2A for 6 h gave 4-(bromomethyl)-3'-fluoro-4'-(trifluoromethoxy)-1,1'-biphenyl (40) (100%) as a cream solid that was used directly in the next step; $^1$H NMR (CDCl$_3$) δ 7.52 (dt, J=8.5, 2.2 Hz, 2H), 7.48 (dt, J=8.5, 2.2 Hz, 2H), 7.43-7.32 (m, 3H), 4.54 (s, 2H); HRAPCIMS calcd for C$_{14}$H$_9$F$_4$O m/z [M−Br]$^+$ 269.0584, found 269.0572.

Reaction of bromide 40 (0.99 equiv.) with alcohol 41 as in Example 2A, followed by chromatography of the product on silica gel, eluting with 0-2% EtOAc/CH$_2$Cl$_2$ (foreruns) and then 2% EtOAc/CH$_2$Cl$_2$, gave 2 (76%) as a cream solid: mp (CH$_2$Cl$_2$/pentane) 169-171° C.; $^1$H NMR (CDCl$_3$) δ 7.54 (dt, J=8.3, 1.8 Hz, 2H), 7.43-7.32 (m, 6H), 4.78 (d, J=12.0 Hz, 1H), 4.67 (d, J=11.9 Hz, 1H), 4.64 (ddd, J=12.1, 3.7, 2.1 Hz, 1H), 4.37 (dd, J=12.1, 1.3 Hz, 1H), 4.23-4.12 (m, 3H). Anal. (C$_{20}$H$_{15}$F$_4$N$_3$O$_5$) C, H, N.

C. Synthesis of (6S)-2-nitro-6-{[4'-(trifluoromethoxy)[1,1'-biphenyl]-4-yl]methoxy}-6,7-dihydro-5H-imidazo[2,1-b][1,3]oxazine (3) by the method of Scheme 2

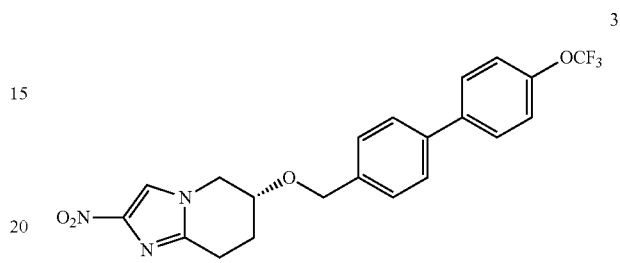

3

Reaction of alcohol 41 with 4-iodobenzyl bromide (42) and NaH in DMF at room temperature for 2 h gave (6S)-6-[(4-iodobenzyl)oxy]-2-nitro-6,7-dihydro-5H-imidazo[2,1-b][1,3]oxazine (43) (reported in U.S. Pat. No. 6,087,358 via the same procedure) (97%) as a pale yellow solid: mp (EtOAc/petroleum ether) 210-212° C.; $^1$H NMR [(CD$_3$)$_2$SO] δ 8.01 (s, 1 H), 7.71 (dt, J=8.3, 2.0 Hz, 2H), 7.13 (br d, J=8.3 Hz, 2H), 4.67-4.60 (m, 2H), 4.59 (d, J=12.2 Hz, 1H), 4.46 (d, J=12.0 Hz, 1H), 4.27-4.19 (m, 3H). Anal. (C$_{13}$H$_{12}$IN$_3$O$_4$) C, H, N.

Suzuki coupling of iodide 43 and 4-(trifluoromethoxy)phenylboronic acid (44) as in Example 2D below gave 3 (86%) as a cream solid: mp (CH$_2$/Cl$_2$/hexane) 199-201° C.; $^1$H NMR [(CD$_3$)$_2$SO] δ 8.03 (s, 1H), 7.78 (dt, J=8.8, 2.6 Hz, 2H), 7.66 (br d, J=8.3 Hz, 2H), 7.43 (br t, J=8.5 Hz, 4H), 4.72 (d, J=12.2 Hz, 1H), 4.70-4.66 (m, 2H), 4.49 (d, J=11.9 Hz, 1H), 4.31-4.21 (m, 3H). Anal. (C$_{20}$H$_{16}$F$_3$N$_3$O$_5$) C, H, N.

D. Synthesis of (6S)-2-nitro-6-({5-[4-(trifluoromethoxy)phenyl]-2-pyrazinyl}methoxy)-6,7-dihydro-5H-imidazo[2,1-b][1,3]oxazine (4) by the method of Scheme 3

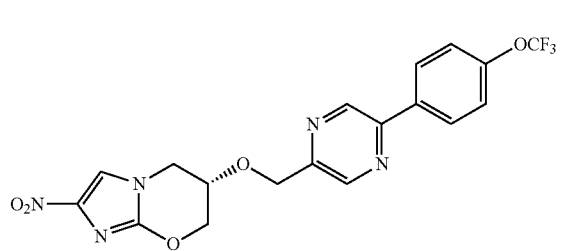

4

Et$_3$N (4.17 mL, 29.9 mmol) and mesyl chloride (1.57 mL, 20.3 mmol) were added to a solution of (5-chloro-2-pyrazinyl)methanol (45) (obtained by chlorination and reduction of 5-hydroxypyrazine-2-carboxylic acid, as reported by Kiener et al., 1994) (1.443 g, 9.98 mmol) in anhydrous THF (20 mL) at 0° C. The mixture was stirred at 0° C. for 0.5 h, then partitioned between EtOAc and water. The organic fraction was dried (MgSO$_4$) and the solvent was removed under reduced pressure to give the crude mesylate. The mesylate was dissolved in acetone (40 mL), sodium iodide (7.5 g, 50 mmol) was added, and the mixture was refluxed for 1 h. The solvent was removed under reduced pressure and the residue was partitioned between EtOAc and water. The organic fraction was concentrated under reduced pressure and the residue was chromatographed on silica gel (eluting with $CH_2Cl_2$) to give 2-chloro-5-(iodomethyl)pyrazine (46) (1.54 g, 61%), which was used immediately due to its instability.

NaH (60% w/w, 0.36 g, 9.0 mmol) was added to a solution of oxazine alcohol 41 (0.93 g, 5.02 mmol) and iodide 46 (1.54 g, 6.05 mmol) in DMF (10 mL) at −78° C. The mixture was stirred at 0° C. for 1 h and then quenched with ice. EtOAc (200 mL) was added, the organic layer was dried ($MgSO_4$) and concentrated under reduced pressure. The residue was chromatographed on silica gel, eluting with a gradient of 0-5% MeOH/EtOAc, to give (6S)-6-[(5-chloro-2-pyrazinyl)methoxy]-2-nitro-6,7-dihydro-5H-imidazo[2,1-b][1,3]oxazine (47) (1.015 g, 65%) as a white solid: mp 181-183° C.; $^1$H NMR [$(CD_3)_2$SO] δ 8.76 (d, 1-1.4 Hz, 1H), 8.50 (d, J=1.4 Hz, 1H), 8.02 (s, 1H), 4.85 (d, J=13.7 Hz, 1H), 4.81 (d, 13.7 Hz, 1H), 4.70 (dt, J=12.1, 2.6 Hz, 1H), 4.49 (br d, J=12.0 Hz, 1H), 4.29-4.38 (m, 2H), 4.25 (dd, J=13.5, 3.3 Hz, 1H). Anal. ($C_{11}H_{10}ClN_5O_4$) C, H, N.

A stirred mixture of chloride 47 (0.100 g, 0.32 mmol) and 4-(trifluoromethoxy)phenylboronic acid (44) (0.080 g, 0.39 mmol) in aqueous $K_2CO_3$ (1 mL, 2M), EtOH (3 mL) and toluene (5 mL) was purged with $N_2$ for 5 min. Pd(dppf)$Cl_2$ (5 mg, 6.25 μmol) was added and the mixture was refluxed under $N_2$ for 0.5 h. The solution was partitioned between EtOAc and water, and the organic layer was dried ($MgSO_4$) and concentrated under reduced pressure. The residue was chromatographed on silica gel, initially eluting with EtOAc to remove foreruns, and then elution with EtOAc:MeOH (95:5) gave 4 (0.115 g, 82%) as a white solid: mp 182-184° C.; $^1$H NMR [$(CD_3)_2$SO] δ 9.23 (d, J=1.4 Hz, 1H), 8.72 (d, J=1.4 Hz, 1H), 8.25 (d, J=8.9 Hz, 2H), 8.03 (s, 1H), 7.53 (d, 8.9 Hz, 2H), 4.89 (d, J=13.3 Hz, 1H), 4.85 (d, J=13.3 Hz, 1H), 4.74 (dt, J=12.0, 2.6 Hz, 1H), 4.52 (br d, J=11.9 Hz, 1H), 4.33-4.43 (m, 2H), 4.27 (dd, J=13.5, 3.2 Hz, 1H). Anal. ($C_{18}H_{14}F_3N_5O_5$) C, H, N.

E. Synthesis of (6S)-2-nitro-6-({6-[4-(trifluoromethoxy)phenyl]-3-pyridinyl}methoxy)-6,7-dihydro-5H-imidazo[2,1-b][1,3]oxazine (6) by the method of Scheme 4

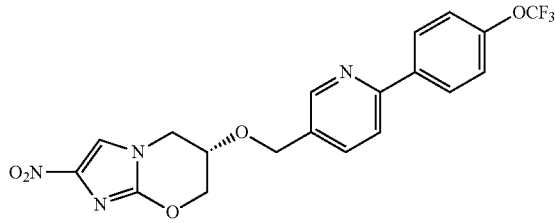

6

NaH (60% w/w, 0.584 g, 14.6 mmol) was added to a solution of oxazine alcohol 41 (2.073 g, 11.2 mmol) and 2-chloro-5-(chloromethyl)pyridine (48) (2.0 g, 12.3 mmol) in anhydrous DMF (40 mL) at 5° C. The resulting mixture was stirred at room temperature for 16 h and then quenched with water (150 mL). The precipitate was filtered off, washed with water and dried to give (6S)-6-[(6-chloro-3-pyridinyl)methoxy]-2-nitro-6,7-dihydro-5H-imidazo[2,1-b][1,3]oxazine (49) (3.39 g, 97%) as a light yellow solid: mp 191-193° C.; $^1$H NMR [$(CD_3)_2$SO] δ 8.37 (d, 1-2.3 Hz, 1H), 8.02 (s, 1H), 7.79 (dd, J=8.3, 2.4 Hz, 1H), 7.51 (br d, J=8.2 Hz, 1H), 4.74 (d, J=12.4 Hz, 1H), 4.69-4.64 (m, 2H), 4.47 (d, J=11.8 Hz, 1H), 4.29-4.21 (m, 3H). HRESIMS calcd for $C_{12}H_{12}ClN_4O_4$ m/z [M+H]$^+$ 313.0513, 311.0542, found 313.0518, 311.0545.

Chloride 49 (1.0 g, 3.22 mmol) and 4-(trifluoromethoxy)phenylboronic acid (44) (0.788 g, 3.82 mmol) were suspended in DME (50 mL) and an aqueous solution of $K_2CO_3$ (2M, 10 mL) was added. The mixture was purged with $N_2$ and then treated with Pd(dppf)$Cl_2$ (50 mg, 0.068 mmol) and stirred at 85° C. in an $N_2$ atmosphere for 1 day, monitoring by MS. Further 44 (0.150 g, 0.728 mmol) was added and the mixture was stirred at 85° C. in an $N_2$ atmosphere for 1 day. The resulting mixture was diluted with water (50 mL), and extracted with EtOAc (3×100 mL). The dried ($MgSO_4$) organic layers were adsorbed onto silica gel and chromatographed on silica gel, eluting with EtOAc. Trituration of the product in $Et_2O$ gave 6 (0.942 g, 67%) as a white powder: mp 217-219° C.; $^1$H NMR [$(CD_3)_2$SO] δ 8.63 (d, J=1.7 Hz, 1H), 8.20 (dt, J=8.9, 2.1 Hz, 2H), 8.03 (s, 1H), 7.99 (dd, J=8.2, 0.5 Hz, 1H), 7.84 (dd, J=8.2, 2.2 Hz, 1H), 7.47 (dd, J=8.8, 0.8 Hz, 2H), 4.77 (d, J=12.3 Hz, 1H), 4.71-4.68 (m, 2H), 4.49 (d, J=11.7 Hz, 1H), 4.31-4.26 (m, 3H). Anal. ($C_{19}H_{15}F_3N_4O_5$) C, H, N. HPLC purity: 98.9%.

F. Synthesis of (6S)-6-{[6-(4-fluorophenyl)-3-pyridinyl]methoxy}-2-nitro-6,7-dihydro-5H-imidazo[2,1-b][1,3]oxazine (5) by the method of Scheme 4

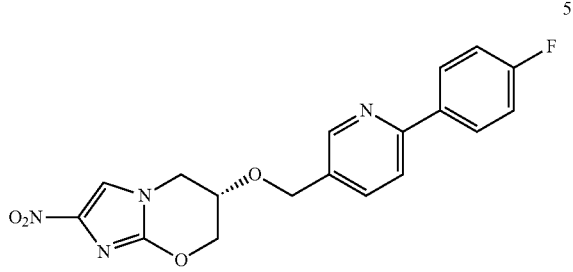 [SMILES: O=[N+]([O-])c1cn2c(n1)OC[C@@H](OCc1ccc(-c3ccc(F)cc3)nc1)C2]

5

A solution of (6-bromo-3-pyridinyl)methanol (50) (2.503 g, 13.3 mmol) and triphenylphosphine (4.026 g, 15.4 mmol) in anhydrous $CH_2Cl_2$ (100 mL) was carefully treated with recrystallized N-bromosuccinimide (2.732 g, 15.4 mmol) (water bath cooling), and the mixture was stirred at room temperature for 3.5 h. The resulting solution was concentrated, and then added to excess petroleum ether at the top of a silica gel column (100 g in petroleum ether), rinsing on with minimal extra $CH_2Cl_2$. Elution with petroleum ether firstly gave foreruns, and then further elution with 15-25% $Et_2O$/pentane gave pure 2-bromo-5-(bromomethyl)pyridine (51) (Schubert et al., 1999) (3.045 g, 91%) as a lachrymatory white solid that was used directly in the next step; $^1$H NMR (CDCl$_3$) δ 8.38 (d, J=2.5 Hz, 1H), 7.59 (dd, J=8.2, 2.6 Hz, 1H), 7.48 (d, J=8.2 Hz, 1H), 4.42 (s, 2H).

A solution of oxazine alcohol 41 (2.224 g, 12.0 mmol) and bromide 51 (3.045 g, 12.1 mmol) in anhydrous DMF (46 mL) under $N_2$ at 0° C. was treated with 60% NaH (639 mg, 16.0 mmol) then quickly degassed and resealed under $N_2$. After stirring at room temperature for 2.5 h, the reaction was cooled ($CO_2$/acetone), quenched with ice/aqueous NaHCO$_3$ (50 mL), added to brine (250 mL) and extracted with CH₂Cl₂ (12×200 mL). The combined extracts were evaporated to dryness and the residue was chromatographed on silica gel. Elution with 0-1% MeOH/CH₂Cl₂ firstly gave foreruns, and then further elution with 1-1.5% MeOH/CH₂Cl₂ gave (6S)-6-[(6-bromo-3-pyridinyl)methoxy]-2-nitro-6,7-dihydro-5H-imidazo[2,1-b][1,3]oxazine (52) (3.739 g, 88%) as a cream solid: mp (MeOH/CH₂Cl₂/hexane) 200-203° C.; ¹H NMR [(CD₃)₂SO] δ 8.35 (dd, J=2.3, 0.4 Hz, 1H), 8.02 (s, 1H), 7.69 (dd, J=8.2, 2.5 Hz, 1H), 7.63 (dd, J=8.1, 0.5 Hz, 1H), 4.72-4.62 (m, 3H), 4.47 (br d, J=11.8 Hz, 1H), 4.31-4.19 (m, 3H). Anal. (C₁₂H₁₁BrN₄O₄) C, H, N. HPLC purity: 100%.

Bromide 52 (0.100 g, 0.28 mmol) and 4-fluorophenylboronic acid (57) (69 mg, 0.49 mmol) were suspended in toluene/EtOH (5 mL/2 mL) and an aqueous solution of K₂CO₃ (2M, 1 mL) was added. The stirred mixture was purged with N₂ and then treated with Pd(dppf)Cl₂ (5 mg, 6.83 μmol) and heated under reflux in an N₂ atmosphere for 20 min. The resulting mixture was diluted with water (10 mL) and extracted with EtOAc (3×15 mL). The dried (MgSO₄) organic layers were adsorbed onto silica gel and chromatographed on silica gel, eluting with EtOAc. Trituration of the product in Et₂O gave 5 (90 mg, 86%): mp 194-196° C.; ¹H NMR [(CD₃)₂SO] δ 8.60 (d, J=1.7 Hz, 1H), 8.14-8.10 (m, 2H), 8.03 (s, 1H), 7.95 (dd, J=8.2, 0.6 Hz, 1H), 7.81 (dd, J=8.2, 2.3 Hz, 1H), 7.31 (br t, J=8.9 Hz, 2H), 4.75 (d, J=12.2 Hz, 1H), 4.71-4.68 (m, 2H), 4.49 (d, J=11.7 Hz, 1H), 4.31-4.26 (m, 3H). Anal. (C₁₈H₁₅FN₄O₄·1.5H₂O) C, N, F. H: calcd, 4.57; found, 3.87. HPLC purity: 99.4%.

G. Synthesis of (6S)-6-({6-[3-fluoro-4-(trifluoromethoxy)phenyl]-3-pyridinyl}methoxy)-2-nitro-6,7-dihydro-5H-imidazo[2,1-b][1,3]oxazine (21) by the method of Scheme 4

21

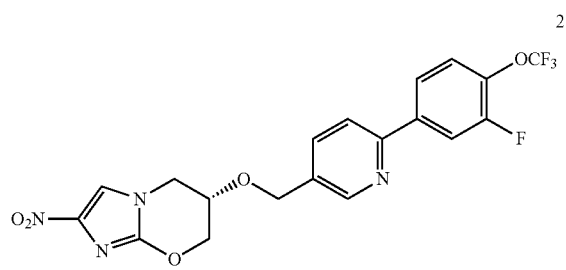

A stirred mixture of bromide 52 (see Example 2F) (502 mg, 1.41 mmol), 3-fluoro-4-(trifluoromethoxy)phenylboronic acid (56) (450 mg, 2.01 mmol) and Pd(dppf)Cl₂ (130 mg, 0.178 mmol) in toluene (20 mL) and EtOH (10 mL) was degassed for 12 min (vacuum pump) and then N₂ was added. An aqueous solution of 2M Na₂CO₃ (3.8 mL, 7.6 mmol) was added by syringe and the stirred mixture was again degassed for 15 min, and then N₂ was added. The resulting mixture was stirred at 90° C. for 2 h, and then cooled, diluted with aqueous NaHCO₃ (100 mL) and extracted with CH₂Cl₂ (6×100 mL). The extracts were evaporated to dryness and the residue was chromatographed on silica gel. Elution with 0-0.5% MeOH/CH₂Cl₂ firstly gave foreruns, and then further elution with 0.5% MeOH/CH₂Cl₂ gave 21 (573 mg, 89%) as a cream solid: mp (CH₂Cl₂/pentane) 187-189° C.; ¹H NMR (CDCl₃) δ 8.62 (d, J=1.5 Hz, 1H), 7.90 (dd, J=11.3, 2.1 Hz, 1H), 7.78 (ddd, J=8.6, 2.0, 1.3 Hz, 1H), 7.75 (dd, J=8.2, 2.2 Hz, 1H), 7.71 (dd, J=8.2, 0.8 Hz, 1H), 7.41 (s, 1H), 7.40 (ddq, J=8.7, 7.6, 1.2 Hz, 1H), 4.80 (d, J=12.0 Hz, 1H), 4.70 (d, J=11.8 Hz, 1H), 4.68 (ddd, J=12.2, 3.5, 2.3 Hz, 1H), 4.40 (dd, J=12.2, 1.1 Hz, 1H), 4.25 (dd, J=13.3, 4.5 Hz, 1 H), 4.22-4.15 (m, 2H). Anal. (C₁₉H₁₄F₄N₄O₅) C, H, N.

H. Synthesis of (6S)-6-({6-[3-chloro-4-(trifluoromethoxy)phenyl]-3-pyridinyl}methoxy)-2-nitro-6,7-dihydro-5H-imidazo[2,1-b][1,3]oxazine (28) by the method of Scheme 4

28

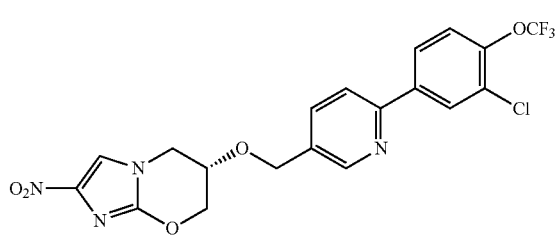

An ice-cold mixture of 98% H₂SO₄ (0.75 mL) and water (2.25 mL) was added to 3-chloro-4-(trifluoromethoxy)aniline (53) (1.00 g, 4.73 mmol) and the resulting salt was crushed (using a glass rod) and cooled in an ice bath. A solution of NaNO₂ (359 mg, 5.20 mmol) in cold water (0.75 mL, then 0.25 mL) was added drop-wise, and the mixture was stirred at 0° C. for 12 min. A solution of urea (42.6 mg, 0.709 mmol) in cold water (0.25 mL) was added, and the mixture was stirred at 0° C. for 3 min. Finally, a solution of KI (1.65 g, 9.94 mmol) in cold water (1.6 mL, then 0.2 mL) was added slowly, and the mixture was stirred at room temperature for 10 min, and then at 52° C. for 2 h. The resulting cooled mixture was diluted with ice-water (45 mL) and extracted with CH₂Cl₂ (4×50 mL). The extracts were sequentially washed with an aqueous solution of Na₂SO₃ (30 mL of 0.5%) and then with water (40 mL) and finally concentrated carefully under reduced pressure at 17° C. The resulting oil was chromatographed on silica gel, eluting with pentane, to give 2-chloro-4-iodo-1-(trifluoromethoxy)benzene (54) (1.24 g, 81%) as a colourless oil (a white solid on freezing); ¹H NMR (CDCl₃) δ 7.82 (d, J=2.1 Hz, 1H), 7.61 (dd, J=8.6, 2.1 Hz, 1H), 7.05 (dq, J=8.6, 2.0 Hz, 1H); HRAPCIMS calcd for C₇H₃ClF₃IO m/z (M⁺) 323.8834, 321.8864, found 323.8834, 321.8861.

Triisopropylborate (0.76 mL, 3.29 mmol) and iodide 54 (815 mg, 2.53 mmol) were successively added via syringe to a mixture of anhydrous toluene (4 mL) and anhydrous distilled THF (1 mL) under N₂ and the mixture was cooled to −78° C. n-Butyllithium (1.08 mL of a 2.5 M solution in hexanes, 2.70 mmol) was added drop-wise over 75 min to the stirred solution (at −78° C.), and the mixture was stirred at −78° C. for an additional 3 h, and then slowly warmed to −20° C. (over 1.5H). 2N HCl (2.6 mL) was added and the mixture was stirred at room temperature for 30 min, and then diluted with water (40 mL) and extracted with EtOAc (5×50 mL). The extracts were washed with brine (50 mL) and then evaporated to dryness. The residue was triturated in pentane (~3-4 mL), cooled to −78° C., and rapidly filtered cold (washing with pentane cooled to −78° C.) to give 3-chloro-4-(trifluoromethoxy)phenylboronic acid (55) (459 mg, 76%) as a white solid (a 1:1 mixture of the trimeric boroxine and the boronic acid by NMR): mp 202-204° C.; ¹H NMR (CDCl₃) δ 8.26 (d, J=1.5 Hz, 3H, boroxine), 8.12 (dd, J=8.2, 1.5 Hz, 3H, boroxine), 7.85 (d, J=1.5 Hz, 1H, boronic acid), 7.65 (dd, J=8.2, 1.6

Hz, 1H, boronic acid), 7.48 (dq, J=8.2, 1.5 Hz, 3H, boroxine), 7.35 (dq, J=8.2, 1.5 Hz, 1H, boronic acid), 4.57 (s, 2H, boronic acid).

Suzuki coupling of bromide 52 and boronic acid 55 as in Example 2G, followed by chromatography of the product on silica gel, eluting with 0-0.5% MeOH/CH$_2$Cl$_2$ (foreruns) and then 0.5% MeOH/CH$_2$Cl$_2$ gave 28 (90%) as a cream solid: mp (CH$_2$Cl$_2$/pentane) 169-171° C.; $^1$H NMR (CDCl$_3$) δ 8.63 (br d, J=1.3 Hz, 1H), 8.15 (d, J=2.2 Hz, 1H), 7.91 (dd, J=8.6, 2.2 Hz, 1H), 7.75 (dd, J=8.2, 2.1 Hz, 1H), 7.71 (dd, J=8.2, 0.8 Hz, 1H), 7.44-7.39 (m, 2H), 4.80 (d, J=12.0 Hz, 1H), 4.70 (d, J=11.8 Hz, 1H), 4.68 (ddd, J=12.3, 3.5, 2.2 Hz, 1H), 4.39 (dd, J=12.2, 1.2 Hz, 1H), 4.25 (dd, J=13.3, 4.5 Hz, 1H), 4.22-4.15 (m, 2H). Anal. (C$_{19}$H$_{14}$ClF$_3$N$_4$O$_5$) C, H, N.

I. Synthesis of (6S)-2-nitro-6-({5-[4-(trifluoromethoxy)phenyl]-2-pyridinyl}methoxy)-6,7-dihydro-5H-imidazo[2,1-b][1,3]oxazine (7) by the method of Scheme 5

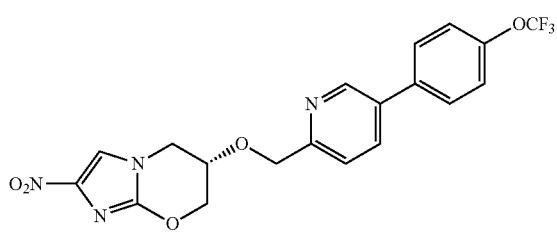

NaH (0.525 g, 13.1 mmol, 60% in mineral oil) was added to a solution of alcohol 41 (1.872, 10.1 mmol) and 5-bromo-2-(chloromethyl)pyridine (58) (prepared by chlorination of (5-bromo-2-pyridinyl)methanol, as reported by van den Fleuvel et al., 2004) (2.5 g, 12.1 mmol) in anhydrous DMF (40 mL) at 5° C. The resulting mixture was stirred at room temperature for 2 h and then quenched with water (300 mL). The precipitate was filtered off, washed with water and dried to give (6S)-6-[(5-bromo-2-pyridinyl)methoxy]-2-nitro-6,7-dihydro-5H-imidazo[2,1-b][1,3]oxazine (59) (3.087 g, 86%) as a light brown solid: mp 171-173° C.; $^1$H NMR [(CD$_3$)$_2$SO] δ 8.65 (dd, J=2.3, 0.4 Hz, 1H), 8.04 (dd, J=8.4, 2.4 Hz, 1H), 8.02 (s, 1H), 7.35 (dd, J=8.4, 0.4 Hz, 1H), 4.72-4.66 (m, 3H), 4.49 (br d, J=12.0 Hz, 1H), 4.35-4.21 (m, 3H). Anal. (C$_{12}$H$_{11}$BrN$_4$O$_4$) C, H, N. HPLC purity: 99.4%.

Bromide 59 (0.100 g, 0.28 mmol) and 4-(trifluoromethoxy)phenylboronic acid (44) (0.075 g, 0.366 mmol) were suspended in toluene/EtOH (5 mL/2 mL) and an aqueous solution of K$_2$CO$_3$ (1 mL; 2M) was added. The stirred mixture was purged with N$_2$ and then treated with Pd(dppf)Cl$_2$ (5 mg, 6.83 μmol) and heated under reflux in an N$_2$ atmosphere for 30 min. The resulting mixture was diluted with water (10 mL) and extracted with EtOAc (3×15 mL). The dried (MgSO$_4$) organic layers were adsorbed onto silica gel and chromatographed on silica gel, eluting with 5% MeOH/EtOAc. Trituration of the product in Et$_2$O gave 7 (97 mg, 79%): mp 157-159° C.; $^1$H NMR [(CD$_3$)$_2$SO] δ 8.85 (d, J=2.0 Hz, 1H), 8.11 (dd, J=8.1, 2.4 Hz, 1H), 8.03 (s, 1H), 7.85 (dt, J=8.8, 2.0 Hz, 2H), 7.48 (t, J=7.7 Hz, 3H), 4.82 (d, J=13.2 Hz, 1H), 4.78 (d, J=13.2 Hz, 1H), 4.72 (dt, J=12.0, 2.6 Hz, 1H), 4.51 (d, J=12.0 Hz, 1H), 4.37-4.24 (m, 3H). Anal. (C$_{19}$H$_{15}$F$_3$N$_4$O$_5$) C, H, N, F. HPLC purity: 100%.

J. Synthesis of (6S)-2-nitro-6-({4-[5-(trifluoromethyl)-2-pyridinyl]benzyl}oxy)-6,7-dihydro-5H-imidazo[2,1-b][1,3]oxazine (8) by the method of Scheme 6

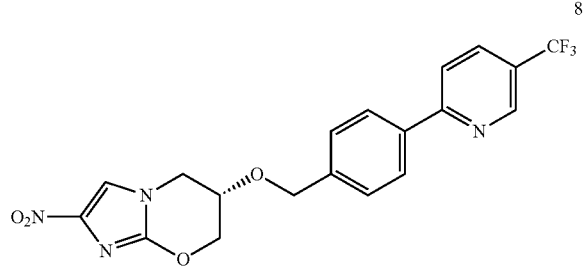

Reaction of oxazine alcohol 41 (5.00 g, 27.0 mmol) with 4-bromobenzyl bromide (60) (7.62 g, 30.5 mmol) and NaH (60% w/w, 1.40 g, 35.0 mmol) in DMF (100 mL) for 2 h at room temperature gave (6S)-6-[(4-bromobenzyl)oxy]-2-nitro-6,7-dihydro-5H-imidazo[2,1-b][1,3]oxazine (61) (8.368 g, 88%) as a light yellow solid: mp (Et$_2$O) 188-190° C.; $^1$H NMR [(CD$_3$)$_2$SO] δ 8.01 (s, 1H), 7.54 (dt, J=8.4, 2.2 Hz, 2H), 7.13 (dt, J=8.5, 2.2 Hz, 2H), 4.67-4.62 (m, 2H), 4.61 (d, J=12.2 Hz, 1H), 4.46 (d, J=12.0 Hz, 1H), 4.28-4.19 (m, 3H). Anal. (C$_{13}$H$_{12}$BrN$_3$O$_4$) C, H, N.

A mixture of bromide 61 (2.00 g, 5.65 mmol), bis(pinacolato)diboron (1.59 g, 6.29 mmol) and KOAc (3.40 g, 34.7 mmol) in DMSO (40 mL) was purged with N$_2$. Pd(dppf)Cl$_2$ (0.14 g, 0.17 mmol) was added and the mixture was purged with N$_2$ through the solution while heating to 90° C. After 1 h the reaction was partitioned between EtOAc and water, and the organic extract was purified by chromatography on silica gel, eluting with EtOAc. The product was triturated in Et$_2$O to give (6S)-2-nitro-6-{[4-(4,4,5,5-tetramethyl-1,3,2-dioxaborolan-2-yl)benzyl]oxy}-6,7-dihydro-5H-imidazo[2,1-b][1,3]oxazine (62) (1.158 g, 51%): mp 150-153° C.; $^1$H NMR [(CD$_3$)$_2$SO] δ 8.01 (s, 1H), 7.65 (d, J=8.0 Hz, 2H), 7.32 (d, J=8.0 Hz, 2H), 4.70 (d, J=12.5 Hz, 1H), 4.67-4.63 (m, 2H), 4.46 (d, J=11.9 Hz, 1H), 4.29-4.20 (m, 3H), 1.29 (s, 12H). Anal. (C$_{19}$H$_{24}$BN$_3$O$_6$) C, H, N.

A mixture of boronate ester 62 (0.094 g, 0.23 mmol) and 2-chloro-5-(trifluoromethyl)pyridine (53 mg, 0.29 mmol) in toluene (5 mL), EtOH (3 mL) and aqueous K$_2$CO$_3$ (2M, 1 mL, 2 mmol) was purged with N$_2$. Pd(dppf)Cl$_2$ (8 mg, 0.01 mmol) was added and the mixture was refluxed under N$_2$ for 0.5 h, then partitioned between EtOAc and water. The organic layer was dried and evaporated, and then column chromatography on silica gel using gradient elution (1:1 hexanes:EtOAc then EtOAc) gave 8 (60 mg, 62%) as a white solid: mp (Et$_2$O triturate) 252-254° C.; $^1$H NMR [(CD$_3$)$_2$SO] δ 9.03 (br s, 1H), 8.27 (dd, J=8.5, 2.1 Hz, 1H), 8.18 (d, J=8.4 Hz, 1H), 8.15 (d, J=8.3 Hz, 2H), 8.03 (s, 1H), 7.48 (d, J=8.3 Hz, 2H), 4.66-4.78 (m, 3H), 4.49 (d, J=11.8 Hz, 1H), 4.23-4.33 (m, 3H). Anal. (C$_{19}$H$_{15}$F$_3$N$_4$O$_4$) C, H, N.

K. Synthesis of (6S)-2-nitro-6-({4-[6-(trifluoromethyl)-3-pyridinyl]benzyl}oxy)-6,7-dihydro-5H-imidazo[2,1-b][1,3]oxazine (9) by the method of Scheme 6

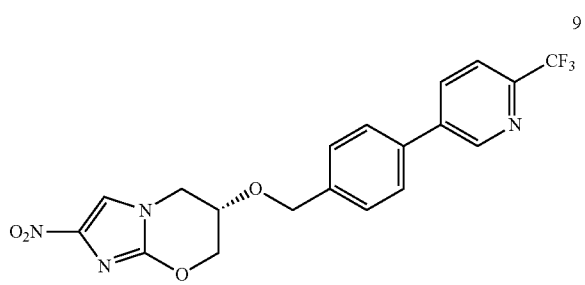 [SMILES: O=[N+]([O-])c1cn2c(n1)OC[C@@H](OCc1ccc(-c3ccc(C(F)(F)F)nc3)cc1)C2]

9

Reaction of boronate ester 62 (see Example 2J) (0.157 g, 0.391 mmol) and 5-bromo-2-(trifluoromethyl)pyridine (0.110 g, 0.487 mmol) as in Example 2J gave 9 (0.105 g, 64%) as a white solid: mp (Et$_2$O triturate) 221-222° C.; $^1$H NMR [(CD$_3$)$_2$SO] δ 9.08 (d, J=2.1 Hz, 1H), 8.35 (dd, J=8.1, 1.9 Hz, 1H), 8.03 (s, 1H), 7.97 (d, J=8.1 Hz, 1H), 7.81 (d, J=8.3 Hz, 2H), 7.48 (d, J=8.3 Hz, 2H), 4.67-4.77 (m, 3H), 4.49 (d, J=11.8 Hz, 1H), 4.22-4.33 (m, 3H). Anal. (C$_{19}$H$_{15}$F$_3$N$_4$O$_4$) C, H, N.

L. Synthesis of (6S)-2-nitro-6-({1-[4-(trifluoromethoxy)phenyl]-1H-pyrazol-3-yl}methoxy)-6,7-dihydro-5H-imidazo[2,1-b][1,3]oxazine (10) by the method of Scheme 7

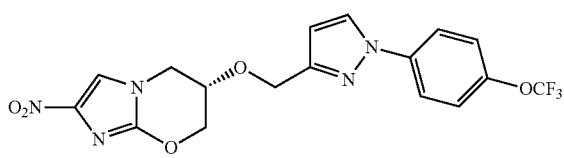

10

4-Trifluoromethoxybenzenediazonium tetrafluoroborate (63) (4.33 g, 15.7 mmol) was added to a solution of ethyl 2-chloroacetoacetate (64) (2.35 g, 14.3 mmol) in pyridine (6 mL) and water (6 mL) at −5° C. The mixture was stirred at −5° C. for 0.5 h and the precipitate was filtered and washed with ice cold water. Recrystallisation from EtOH/water gave ethyl 2-chloro{[4-(trifluoromethoxy)phenyl]hydrazono}ethanoate (65) (3.977 g, 82%) as pale orange needles: mp 128-130° C.; $^1$H NMR [(CD$_3$)$_2$SO] δ 10.68 (s, 1H), 7.43 (d, J=9.2 Hz, 2H), 7.34 (d, J=9.2 Hz, 2H), 4.30 (t, J=7.1 Hz, 2H), 1.30 (q, J=7.1 Hz, 3H). APCI MS m/z 309, 311 [M−H]$^−$.

A stirred mixture of hydrazonoyl chloride 65 (1.55 g, 4.99 mmol), bicyclo[2.2.1]hepta-2,5-diene (1.25 mL, 24.6 mmol) and Et$_3$N (2.0 mL, 14.3 mmol) in toluene (10 mL) was heated to 70° C. for 1 h. The mixture was cooled and filtered, the filter cake was washed with toluene (10 mL) and the organic fractions were combined and evaporated. The residue was refluxed in xylenes (30 mL) for 2 h. Column chromatography on silica gel, eluting with hexanes, firstly gave xylenes, and then further elution with CH$_2$Cl$_2$ gave ethyl 1-[4-(trifluoromethoxy)phenyl]-1H-pyrazole-3-carboxylate (66) (1.176 g, 79%) as a white solid: mp 76-78° C.; $^1$H NMR (CDCl$_3$) δ 7.91 (d, J=2.5 Hz, 1H), 7.79 (d, J=8.9 Hz, 2H), 7.33 (d, J=8.9 Hz, 2H), 7.00 (d, J=2.5 Hz, 1H), 4.44 (q, J=7.1 Hz, 2H), 1.43 (t, J=7.1 Hz, 3H). APCI MS m/z 301 [M+H]$^+$.

LiAlH$_4$ (0.137 g, 3.61 mmol) was added to a solution of ester 66 (1.081 g, 3.60 mmol) in Et$_2$O (20 mL) at 0° C. and the stirred mixture was warmed to room temperature for 1 h, then cooled to 0° C. and quenched with ice. The mixture was diluted with Et$_2$O (100 mL) and saturated aqueous sodium potassium tartrate (100 mL) and then filtered through Celite. The organic layer was dried and chromatographed on silica gel, eluting with CH$_2$Cl$_2$:EtOAc (95:5), to give {1-[4-(trifluoromethoxy)phenyl]-1H-pyrazol-3-yl}methanol (67) (0.888 g, 96%) as a white solid: mp 53-54° C.; $^1$H NMR [(CD$_3$)$_2$SO] δ 8.44 (d, J=2.5 Hz, 1H), 7.92 (d, J=8.5 Hz, 2H), 7.48 (d, J=8.5 Hz, 2H), 6.50 (d, J=2.5 Hz, 1H), 5.15 (t, J=5.8 Hz, 1H), 4.51 (d, J=5.8 Hz, 2H). APCI MS m/z 259 [M+H]$^+$.

PBr$_3$ (0.312 mL, 3.32 mmol) was added to a solution of alcohol 67 (0.858 g, 3.32 mmol) in ether (15 mL) at 0° C. The mixture was stirred at room temperature for 17 h, then cooled to 0° C., quenched with ice, and partitioned between CH$_2$Cl$_2$ and water. Column chromatography of the organic portion on silica gel (eluting with CH$_2$Cl$_2$) gave 3-(bromomethyl)-1-[4-(trifluoromethoxy)phenyl]-1H-pyrazole (68) (0.952 g, 89%) as a white solid: mp 71-73° C.; $^1$H NMR (CDCl$_3$) δ 7.84 (d, J=2.5 Hz, 1H), 7.69 (d, J=9.1 Hz, 2H), 7.31 (d, J=9.1 Hz, 2H), 6.54 (d, J=2.5 Hz, 1H), 4.56 (s, 2H). APCI MS m/z 321, 323 [M+H]$^+$.

NaH (60% w/w, 160 mg, 4.00 mmol) was added to a solution of oxazine alcohol 41 (0.473 g, 2.55 mmol) and bromide 68 (0.913 g, 2.84 mmol) in DMF (50 mL) at 0° C. The mixture was stirred at 0° C. for 2 h and then quenched with ice and partitioned between EtOAc and water. The organic fraction was dried and evaporated, and then column chromatography on silica gel, eluting with a gradient of 1:1 hexanes:EtOAc to EtOAc, gave 10 (0.844 g, 78%) as a white solid: mp 103-105° C.; $^1$H NMR [(CD$_3$)$_2$SO] δ 8.50 (d, J=2.5 Hz, 1H), 8.01 (s, 1H), 7.93 (d, J=9.1 Hz, 2H), 7.49 (d, J=9.1 Hz, 2H), 6.54 (d, J=2.5 Hz, 1H), 4.68-4.74 (m, 2H), 4.65 (dt, J=12.3, 2.4 Hz, 1H), 4.47 (d, J=11.8 Hz, 1H), 4.20-4.31 (m, 3H). Anal. ($C_{17}H_{14}F_3N_5O_5$) C, H, N.

M. Synthesis of (6S)-6-({1-methyl-3-[4-(trifluoromethoxy)phenyl]-1H-pyrazol-5-yl}methoxy)-2-nitro-6,7-dihydro-5H-imidazo[2,1-b][1,3]oxazine (11) by the method of Scheme 8

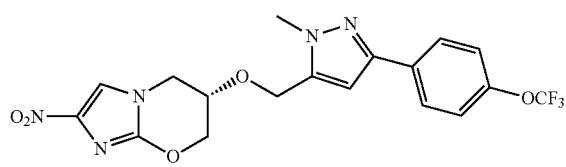

11

A solution of 2-(2-propynyloxy)tetrahydro-2H-pyran (69) (0.758 g, 5.41 mmol), CuI (17 mg, 0.09 mmol) and $PdCl_2(PPh_3)_2$ (0.158 g, 0.023 mmol) in THF (15 mL) was purged with $N_2$. 1-Iodo-4-(trifluoromethoxy)benzene (70) (1.30 g, 4.51 mmol) in THF (10 mL) was added, followed by a solution of methylhydrazine sulfate (1.95 g, 13.5 mmol) and $NaHCO_3$ (2.27 g, 27 mmol) in water (25 mL). The mixture was flushed with carbon monoxide and then stirred at room temperature for 2 days under one atmosphere of carbon monoxide. The resulting mixture was partitioned between $CH_2Cl_2$ and water, the $CH_2Cl_2$ fraction was dried, and the solvent was evaporated. Column chromatography of the residue on silica gel (eluting with $CH_2Cl_2$) gave 1-methyl-5-[tetrahydro-2H-pyran-2-yloxy)methyl]-3-[4-(trifluoromethoxy)phenyl]-1H-pyrazole (71) (1.034 g, 64%) as a brown solid: mp 40-42° C.; $^1$H NMR ($CDCl_3$) δ 7.78 (d, J=8.8 Hz, 2H), 7.21 (d, J=8.0 Hz, 2H), 6.51 (s, 1H), 4.75 (d, J=12.8 Hz, 1H), 4.69 (t, J=3.3 Hz, 1H), 4.57 (d, J=12.8 Hz, 1H), 3.94 (s, 3H), 3.84-3.91 (m, 1H), 3.53-3.60 (m, 1H), 1.68-1.88 (m, 2H), 1.50-1.66 (m, 4H). APCI MS m/z 357 [M+H]$^+$.

A stirred solution of THP ether 71 (0.968 g, 2.72 mmol) in HCl (4M, 10 mL) and THF (10 mL) was heated to 80° C. for 16 h. The THF was evaporated and the residue was partitioned between EtOAc and aqueous $NaHCO_3$. The organic layer was dried and evaporated, and the residue was recrystallised ($^iPr_2O$) to give {1-methyl-3-[4-(trifluoromethoxy)phenyl]-1H-pyrazol-5-yl}methanol (72) (0.278 g, 38%) as a white solid: mp 91-93° C.; $^1$H NMR [($CD_3)_2SO$] δ 7.86 (d, J=8.9 Hz, 2H), 7.36 (d, J=8.9 Hz, 2H), 6.64 (s, 1H), 5.30 (t, J=5.2 Hz, 1H), 4.52 (d, J=5.2 Hz, 2H), 3.84 (s, 3H). APCI MS m/z 273 [M+H]$^+$.

$PBr_3$ (0.15 mL, 1.60 mmol) was added to a solution of alcohol 72 (0.205 g, 0.75 mmol) in $Et_2O$ (10 mL) at 0° C. The mixture was stirred at room temperature for 16 h, cooled to 0° C., quenched with ice and diluted with $Et_2O$ (100 mL). Chromatography of the organic portion on silica gel (eluting with $CH_2Cl_2$) gave 5-(bromomethyl)-1-methyl-3-[4-(trifluoromethoxy)phenyl]-1H-pyrazole (73) (0.212 g, 85%) as a white solid: mp 70-71° C.; $^1$H NMR ($CDCl_3$) δ 7.76 (d, J=8.9 Hz, 2H), 7.22 (d, J=8.9 Hz, 2H), 6.55 (s, 1H), 4.50 (s, 2H), 3.94 (s, 3H). APCI MS m/z 335, 337 [M+H]$^+$.

NaH (95% w/w, 25 mg, 0.99 mmol) was added to a solution of alcohol 41 (0.113 g, 0.61 mmol) and bromide 73 (0.207 g, 0.62 mmol) in DMF (6 mL) at 0° C. The mixture was stirred at 0° C. for 2 h, then quenched with ice and partitioned between EtOAc and water. The organic layer was dried and the solvent was evaporated. Column chromatography of the residue on silica gel, eluting with a gradient of 1:1 hexanes:EtOAc to EtOAc, gave 11 (0.130 g, 48%) as a white solid: mp 178-179° C.; $^1$H NMR [($CD_3)_2SO$] δ 8.02 (s, 1H), 7.85 (d, J=8.9 Hz, 2H), 7.36 (d, J=8.9 Hz, 2H), 6.76 (s, 1H), 4.77 (d, J=12.6 Hz, 1H), 4.72 (d, J=12.6 Hz, 1H), 4.69 (dt, J=12.1, 2.3 Hz, 1H), 4.48 (d, J=11.8 Hz, 1H), 4.21-4.32 (m, 3H), 3.79 (s, 3H). Anal. ($C_{18}H_{16}F_3N_5O_5$) C, H, N.

N. Synthesis of (6S)-6-{[3-fluoro-4'-(trifluoromethoxy)[1,1'-biphenyl]-4-yl]methoxy}-2-nitro-6,7-dihydro-5H-imidazo[2,1-b][1,3]oxazine (12) by the method of Scheme 9

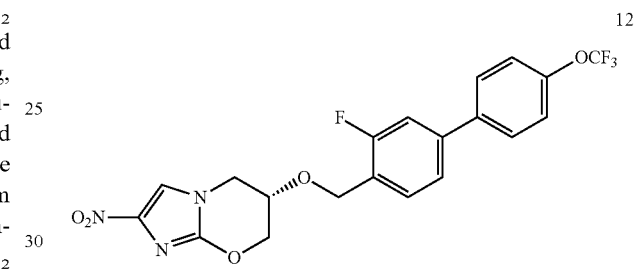

A solution of alcohol 41 (1.403 g, 7.58 mmol) and 4-bromo-1-(bromomethyl)-2-fluorobenzene (74) (2.66 g, 9.93 mmol) in anhydrous DMF (30 mL) under $N_2$ at 0° C. was treated with 60% NaH (427 mg, 10.7 mmol), then quickly degassed and resealed under $N_2$. After stirring at room temperature for 3 h, the reaction was cooled ($CO_2$/acetone), quenched with ice/aqueous $NaHCO_3$ (20 mL), added to brine (150 mL) and extracted with $CH_2Cl_2$ (4×80 mL). The combined extracts were evaporated to dryness and the residue was chromatographed on silica gel. Elution with 0-2% EtOAc/$CH_2Cl_2$ firstly gave foreruns, and then elution with 3-5% EtOAc/$CH_2Cl_2$ gave (6S)-6-[(4-bromo-2-fluorobenzyl)oxy]-2-nitro-6,7-dihydro-5H-imidazo[2,1-b][1,3]oxazine (75) (2.633 g, 93%) as a pale yellow solid: mp (MeOH/$CH_2Cl_2$/hexane) 171-173° C.; $^1$H NMR [($CD_3)_2SO$] δ 8.01 (s, 1H), 7.54 (dd, J=9.7, 1.8 Hz, 1H), 7.42 (dd, J=8.2, 1.8 Hz, 1H), 7.37 (dd, J=8.1, 7.7 Hz, 1H), 4.72-4.62 (m, 3H), 4.47 (br d, J=11.9 Hz, 1H), 4.30-4.19 (m, 3H). Anal. ($C_{13}H_{11}BrFN_3O_4$) C, H, N.

A stirred mixture of bromide 75 (475 mg, 1.28 mmol), 4-(trifluoromethoxy)phenylboronic acid (44) (395 mg, 1.92 mmol) and Pd(dppf)$Cl_2$ (143 mg, 0.195 mmol) in toluene (18 mL) and EtOH (7 mL) was degassed for 8 min (vacuum pump) and then $N_2$ was added. An aqueous solution of 2M $Na_2CO_3$ (3.5 mL, 7.0 mmol) was added by syringe and the stirred mixture was again degassed for 8 min, and then $N_2$ was added. The resulting mixture was stirred at 85° C. for 70 min, and then cooled, diluted with aqueous $NaHCO_3$ (50 mL) and extracted with $CH_2Cl_2$ (6x 50 mL). The extracts were evaporated to dryness and the residue was chromatographed on silica gel. Elution with 0-1% EtOAc/$CH_2Cl_2$ firstly gave foreruns, and then further elution with 1-2% EtOAc/$CH_2Cl_2$ gave 12 (539 mg, 93%) as a pale yellow solid: mp ($CH_2Cl_2$/pentane) 160-162° C.; $^1$H NMR ($CDCl_3$) δ 7.57 (dt, J=8.8, 2.5 Hz, 2H), 7.42 (t, J=7.7 Hz, 1H), 7.39 (s, 1H), 7.35 (dd, J=7.9, 1.7 Hz, 1H), 7.33-7.23 (m, 3H), 4.81-4.73 (m, 2H), 4.65 (ddd, J=12.2, 3.6, 2.0 Hz, 1H), 4.38 (br d, J=12.1 Hz, 1H), 4.25-4.13 (m, 3H). Anal. ($C_{20}H_{15}F_4N_3O_5$) C, H, N.

O. Synthesis of (6S)-6-({2-fluoro-4-[6-(trifluoromethyl)-3-pyridinyl]benzyl}oxy)-2-nitro-6,7-dihydro-5H-imidazo[2,1-b][1,3]oxazine (23) by the method of Scheme 9

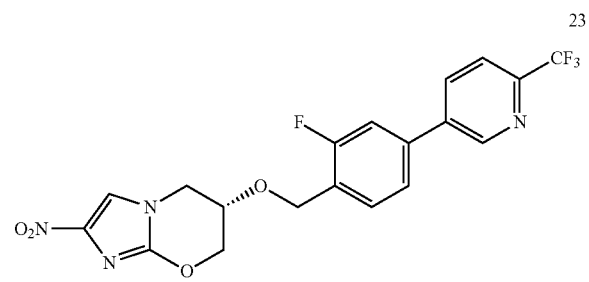 [SMILES: O=[N+]([O-])c1cn2c(n1)OC[C@@H](OCc1ccc(-c3ccc(C(F)(F)F)nc3)cc1F)C2]

23

A stirred mixture of bromide 75 (see Example 2N) (503 mg, 1.35 mmol), 6-(trifluoromethyl)-3-pyridinylboronic acid (386 mg, 2.02 mmol) and Pd(dppf)Cl$_2$ (148 mg, 0.202 mmol) in toluene (20 mL) and EtOH (10 mL) was degassed for 12 min (vacuum pump) and then N$_2$ was added. An aqueous solution of 2M Na$_2$CO$_3$ (3.5 mL, 7.0 mmol) was added by syringe and the stirred mixture was again degassed for 12 min, and then N$_2$ was added. The resulting mixture was stirred at 90° C. for 3 h, and then cooled, diluted with aqueous NaHCO$_3$ (100 mL) and extracted with CH$_2$Cl$_2$ (6×100 mL). The extracts were evaporated to dryness and the residue was chromatographed on silica gel. Elution with 0-3% EtOAc/ CH$_2$Cl$_2$ firstly gave foreruns, and then further elution with 3-4% EtOAc/CH$_2$Cl$_2$ gave 23 (530 mg, 90%) as a cream solid: mp (MeOH/CH$_2$Cl$_2$/pentane) 195-198° C.; $^1$H NMR [(CD$_3$)$_2$SO] δ 9.12 (d, J=2.1 Hz, 1H), 8.40 (dd, J=8.1, 1.9 Hz, 1H), 8.03 (s, 1H), 7.99 (d, J=8.1 Hz, 1H), 7.75 (dd, J=11.3, 1.7 Hz, 1H), 7.68 (dd, J=7.9, 1.8 Hz, 1H), 7.57 (t, J=7.8 Hz, 1H), 4.80 (br d, J=13.0 Hz, 1H), 4.76 (br d, J=13.3 Hz, 1H), 4.69 (dt, J=12.0, 2.5 Hz, 1H), 4.50 (br d, J=11.7 Hz, 1H), 4.35-4.22 (m, 3H). Anal. ($C_{19}H_{14}F_4N_4O_4$) C, H, N.

P. Synthesis of (6S)-6-({2-fluoro-4-[5-(trifluoromethyl)-2-pyridinyl]benzyl}oxy)-2-nitro-6,7-dihydro-5H-imidazo[2,1-b][1,3]oxazine (14) by the method of Scheme 9

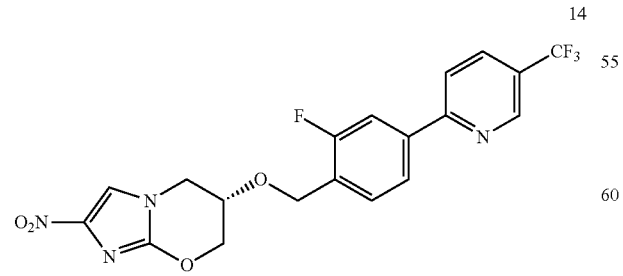

14

A stirred mixture of bromide 75 (see Example 2N) (1.601 g, 4.30 mmol), bis(pinacolato)diboron (1.179 g, 4.64 mmol), Pd(dppf)Cl$_2$ (0.473 g, 0.646 mmol) and KOAc (1.497 g, 15.3 mmol) in anhydrous DMSO (24 mL) was degassed for 35 min (vacuum pump) and then N$_2$ was added. The mixture was stirred at 89° C. for 5 h, and then cooled, added to ice-water (150 mL) and extracted with EtOAc (5×100 mL). The extracts were washed with water (2×100 mL), evaporated to dryness and the residue was chromatographed on silica gel. Elution with 50% EtOAc/petroleum ether firstly gave foreruns, and then further elution with 50-67% EtOAc/petroleum ether gave (6S)-6-{[2-fluoro-4-(4,4,5,5-tetramethyl-1,3,2-dioxaborolan-2-yl)benzyl]oxy}-2-nitro-6,7-dihydro-5H-imidazo [2,1-b][1,3]oxazine (76) (1.186 g, 66%) as a cream solid: mp (CH$_2$Cl$_2$/Et$_2$O/pentane) 147-149° C.; $^1$H NMR (CDCl$_3$) δ 7.58 (dd, J=7.5, 0.9 Hz, 1H), 7.49 (br d, J=10.3 Hz, 1H), 7.38 (s, 1H), 7.35 (t, J=7.3 Hz, 1H), 4.76 (d, J=12.9 Hz, 1H), 4.73 (d, J=12.7 Hz, 1H), 4.59 (ddd, J=12.1, 3.8, 2.0 Hz, 1H), 4.34 (dd, J=12.0, 1.5 Hz, 1H), 4.20-4.07 (m, 3H), 1.34 (s, 12H); HRFABMS calcd for $C_{19}H_{23}BFN_3O_6$ m/z [M+H]$^+$ 420.1742, 419.1779, found 420.1733, 419.1763.

A stirred mixture of boronate ester 76 (602 mg, 1.43 mmol), 2-chloro-5-trifluoromethylpyridine (1.08 g, 5.96 mmol) and Pd(dppf)Cl$_2$ (0.232 g, 0.317 mmol) in toluene (18 mL) and EtOH (9 mL) was degassed for 12 min (vacuum pump) and then N$_2$ was added. An aqueous solution of 2M Na$_2$CO$_3$ (3.8 mL, 7.6 mmol) was added by syringe and the stirred mixture was again degassed for 12 min, and then N$_2$ was added. The resulting mixture was stirred at 90° C. for 120 min, and then cooled, diluted with aqueous NaHCO$_3$ (100 mL) and extracted with CH$_2$Cl$_2$ (6×100 mL). The extracts were evaporated to dryness and the residue was chromatographed on silica gel. Elution with 0-2% EtOAc/CH$_2$Cl$_2$ firstly gave foreruns, and then further elution with 2-6% EtOAc/CH$_2$Cl$_2$ gave 14 (523 mg, 83%) as a pale yellow solid: mp (CH$_2$Cl$_2$/hexane) 233-235° C.; $^1$H NMR (CDCl$_3$) δ 8.95 (m, 1H), 8.01 (dd, J=8.3, 2.3 Hz, 1H), 7.86-7.79 (m, 3H), 7.49 (t, J=7.8 Hz, 1H), 7.40 (s, 1H), 4.82 (br d, J=13.1 Hz, 1H), 4.78 (br d, J=13.3 Hz, 1H), 4.66 (ddd, J=12.2, 3.5, 2.0 Hz, 1H), 4.39 (dd, J=12.1, 1.4 Hz, 1H), 4.26-4.14 (m, 3H). Anal. ($C_{19}H_{14}F_4N_4O_4$) C, H, N.

Q. Synthesis of (6S)-2-nitro-6-{[4'-(trifluoromethoxy)[1,1'-biphenyl]-4-yl]oxy}-6,7-dihydro-5H-imidazo[2,1-b][1,3]oxazine (13) by the method of Scheme 10

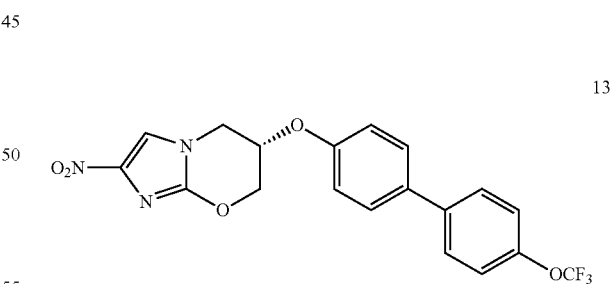

13

A mixture of (S)-glycidol (77) (20 g, 0.27 mol), benzyl alcohol (27.9 mL, 0.27 mol) and CsF (0.82 g, 5.40 mmol) was heated with stirring at 120° C. for 16 h. Unreacted benzyl alcohol was removed using a rotary evaporator attached to a high vacuum line. The product was partitioned between EtOAc and water, and the organic extract was evaporated and chromatographed on silica. Elution with petroleum ether gave fore fractions, and then further elution with EtOAc/ petroleum ether (3:7) gave (2S)-3-(benzyloxy)-1,2-propanediol (78) (9.52 g, 19%) as a viscous oil: [α]$^{19}$ −3.64° (c, 6.59, CHCl$_3$); $^1$H NMR (CDCl$_3$) δ 7.38-7.28 (m, 5H), 4.56 (s, 2H), 3.92-3.87 (m, 1H), 3.71 (dd, J=11.4, 3.9 Hz, 1H), 3.64 (dd, J=11.4, 5.4 Hz, 1H), 3.61-3.57 (m, 2H), 2.60 (br, 1H), 2.22 (br, 1H). APCI MS m/z 183 [M+H]⁺.

Chloro(triisopropyl)silane (12.2 mL, 0.057 mol) was added dropwise at 20° C. to a stirred solution of diol 78 (9.52 g, 0.052 mol) and imidazole (5.33 g, 0.078 mol) in DMF (150 mL) and stirring was continued for 16 h. Most of the DMF was removed under reduced pressure and the residue was partitioned between EtOAc and water. The organic extract was washed well with water, then brine, and was evaporated to give an oil, which was chromatographed on silica. Elution with petroleum ether gave fore fractions, and then further elution with EtOAc/petroleum ether (1:19) gave (2R)-1-(benzyloxy)-3-[(triisopropylsilyl)oxy]-2-propanol (79) (13.80 g, 78%) as a colourless oil: [α]¹⁹ −0.78° (c, 8.93, CHCl₃); ¹H NMR (CDCl₃) δ 7.41-7.27 (m, 5H), 4.55 (s, 2H), 3.90-3.84 (m, 1H), 3.79-3.72 (m, 2H), 3.59-3.51 (m, 2H), 2.52 (d, J=5.1 Hz, 1H), 1.13-1.03 (m, 21H). APCI MS m/z 339 [M+H]⁺.

1,1'-Diisopropyl azodicarboxylate (7.70 mL, 0.039 mol) was added dropwise at 5° C. to a solution of the alcohol 79 (12.40 g, 0.037 mol), 4'-(trifluoromethoxy)[1,1'-biphenyl]-4-ol (reported by Edsall et al., 2003, via Suzuki coupling of 4-bromophenol and boronic acid 44) (8.29 g, 0.033 mol) and triphenylphosphine (10.26 g, 0.039 mol) in anhydrous benzene (25 mL) and the solution was stirred at 20° C. for 18 h. The product was adsorbed directly onto silica by concentration under reduced pressure, and chromatography on silica gel, eluting with EtOAc/petroleum ether (1:19), gave 4-[((1S)-2-(benzyloxy)-1-{[(triisopropylsilyl)oxy]methyl}ethyl)oxy]-4'-(trifluoromethoxy)-1,1'-biphenyl (80) (14.30 g, 69%) as a colourless oil: [α]¹⁹ +5.9° (c, 6.95, CHCl₃); ¹H NMR (CDCl₃) δ 7.72 (d, J=8.8 Hz, 2H), 7.58 (d, J=8.8 Hz, 2H), 7.40 (d, J=8.8 Hz, 2H), 7.35-7.24 (m, 5H), 7.06 (d, J=8.8 Hz, 2H), 4.64-4.57 (m, 1H), 4.52 (s, 2H), 3.98-3.87 (m, 2H), 3.76-3.65 (m, 2H), 1.08-0.98 (m, 21H). APCI MS m/z 576 [M+H]⁺.

A mixture of the benzyl ether 80 (10.79 g, 0.019 mol) and 5% Pd—C (500 mg) in 1:1 EtOAc/EtOH (250 mL) was hydrogenated at 60 psi for 4 h. The catalyst was removed by filtration through Celite and the filtrate was concentrated under reduced pressure to give (2S)-2-{[4'-(trifluoromethoxy)[1,1'-biphenyl]-4-yl]oxy}-3-[(triisopropylsilyl)oxy]-1-propanol (81) as a viscous oil, sufficiently pure for use in the next step. Iodine (6.03 g, 0.024 mol) was added in portions at 20° C. to a vigorously stirred solution of the crude alcohol 81, triphenylphosphine (6.23 g, 0.024 mol) and imidazole (2.49 g, 0.036 mol) in benzene (100 mL) and stirring was continued for 1 h. After dilution with EtOAc the mixture was washed with water, 2N Na₂SO₃ and water again. The extract was evaporated and chromatographed on silica gel, eluting with EtOAc/petroleum ether (1:19), to give 4-[((1R)-2-iodo-1-{[(triisopropylsilyl)oxy]methyl}ethyl)oxy]-4'-(trifluoromethoxy)-1,1'-biphenyl (82) (9.08 g, 81% overall) as a colourless oil; ¹H NMR (CDCl₃) δ 7.54 (d, J=8.8 Hz, 2H), 7.48 (d, J=8.8 Hz, 2H), 7.26 (br d, J=8.8 Hz, 2H), 7.02 (d, J=8.8 Hz, 2H), 4.31-4.25 (m, 1H), 4.03 (dd, J=10.4, 4.8 Hz, 1H), 3.93 (dd, J=10.4, 5.6 Hz, 1H), 3.55 (dd, J=10.5, 5.6 Hz, 1H), 3.45 (dd, J=10.5, 4.8 Hz, 1H), 1.15-1.06 (m, 21H). APCI MS m/z 595 [M+H]⁺.

A mixture of 2-bromo-4(5)-nitroimidazole (0.73 g, 3.82 mmol), the iodide 82 (2.50 g, 4.20 mmol) and K₂CO₃ (0.63 g, 4.58 mmol) in DMF (30 mL) was stirred at 87° C. for 20 h. The resulting mixture was partitioned between EtOAc and brine, and the extract was washed well with brine. Evaporation gave an oil, which was chromatographed on silica gel, eluting with EtOAc/petroleum ether (1:9), to give 2-bromo-4-nitro-1-{(2S)-2-{[4'-(trifluoromethoxy)[1,1'-biphenyl]-4-yl]oxy}-3-[(triisopropylsilyl)oxy]propyl}-1H-imidazole (83) (1.05 g, 42%) as an oil; ¹H NMR (CDCl₃) δ 7.95 (s, 1H), 7.51 (d, J=8.8 Hz, 2H), 7.45 (d, J=8.8 Hz, 2H), 7.25 (br d, J=8.8 Hz, 2H), 6.89 (d, J=8.8 Hz, 2H), 4.63-4.56 (m, 2H), 4.37-4.29 (m, 1H), 4.02 (dd, J=10.7, 3.4 Hz, 1H), 3.84 (dd, J=10.7, 6.8 Hz, 1H), 1.17-1.07 (m, 21H). APCI MS m/z 660, 658 [M+H]⁺.

Tetra-n-butylammonium fluoride (3.18 mL of a 1M solution in THF, 3.18 mmol) was added at 20° C. to a solution of silyl ether 83 (1.05 g, 1.59 mmol) in THF (40 mL) and the solution was stirred at room temperature for 1 h. After dilution with EtOAc, the solution was washed with saturated aqueous NaHCO₃ solution, then water, and then evaporated to give an oil, which was chromatographed on silica. Elution with EtOAc/petroleum ether (1:1) gave fore fractions, and then further elution with EtOAc gave the deprotected alcohol. This material was immediately dissolved in DMF (20 mL) and the solution was cooled to 5° C. and treated with NaH (0.19 g of a 60% dispersion in mineral oil, 4.77 mmol). The cooling bath was removed and the mixture was stirred at 20° C. for 30 min. Water was added, the mixture was extracted with EtOAc and the extract was evaporated to give an oil, which was chromatographed on silica. Elution with EtOAc/petroleum ether (1:1) gave fore fractions, and then further elution with EtOAc/petroleum ether (2:1) gave 13 (175 mg, 26%) as a white solid: mp 210° C.; [α]¹⁹ −9.5° (c, 0.84, acetone); ¹H NMR [(CD₃)₂SO] δ 8.07 (s, 1H), 7.75 (d, J=8.8 Hz, 2H), 7.66 (d, J=8.8 Hz, 2H), 7.41 (br d, J=8.8 Hz, 2H), 7.15 (d, J=8.8 Hz, 2H), 5.31-5.27 (m, 1H), 4.71-4.63 (m, 2H), 4.42 (dd, J=13.8, 3.2 Hz, 1H), 4.34 (br d, J=13.8 Hz, 1H). Anal. (C₁₉H₁₄F₃N₃O₅) C, H, N. Chiral HPLC analysis revealed this product to have an ee of 70%.

R. Synthesis of (6S)-6-{[2-fluoro-4'-(trifluoromethoxy)[1,1'-biphenyl]-4-yl]methoxy}-2-nitro-6,7-dihydro-5H-imidazo[2,1-b][1,3]oxazine (15) by the method of Scheme 11

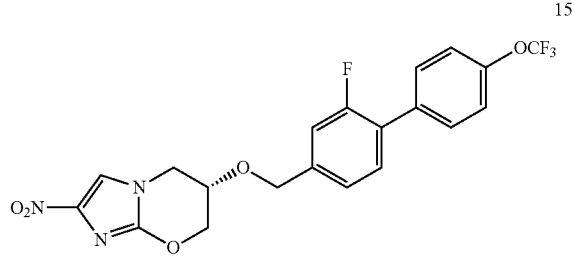 [SMILES: O=[N+]([O-])c1cn2c(n1)OC[C@@H](OCc1ccc(-c3ccc(OC(F)(F)F)cc3)c(F)c1)C2]

A suspension of 4-bromo-3-fluorobenzoic acid (84) (1.61 g, 7.35 mmol) in anhydrous THF (10 mL, then 4×3 mL to rinse) under N₂ was added drop-wise (over 40 min) to a suspension of sodium borohydride (400 mg, 10.6 mmol) in anhydrous THF (15 mL) under N₂, and then the mixture was cooled in an ice bath. A solution of iodine (1.008 g, 3.97 mmol) in anhydrous THF (10 mL, then 2×3 mL) was added drop-wise (over 35 min) to the stirred solution and then the mixture was stirred at room temperature for 14 h. The mixture was concentrated under reduced pressure and then treated successively with water (20 mL), 10% HCl (3.4 mL) and water (20 mL), and extracted with CH₂Cl₂ (4×50 mL). The extracts were evaporated to dryness and the residue was chromatographed on silica gel, eluting with 50% CH₂Cl₂/petroleum ether, to give (4-bromo-3-fluorophenyl)methanol (85) (1.096 g, 73%) as a white solid: mp (CH₂Cl₂/petroleum ether)

39-40° C.; ¹H NMR (CDCl₃) δ 7.52 (dd, J=8.0, 7.2 Hz, 1H), 7.16 (dd, J=9.3, 1.8 Hz, 1H), 7.02 (dd, J=8.2, 1.8 Hz, 1H), 4.67 (d, J=5.9 Hz, 2H), 1.75 (t, J=5.9 Hz, 1H); HREIMS calcd for C₇H₆BrFO m/z (M⁺) 205.9567, 203.9586, found 205.9566, 203.9580.

Bromination of alcohol 85 as in Example 2A for 20 h gave 1-bromo-4-(bromomethyl)-2-fluorobenzene (86) (100%) as a white solid: mp (pentane) 39-41° C.; ¹H NMR (CDCl₃) δ 7.52 (dd, J=8.1, 7.1 Hz, 1H), 7.17 (dd, J=9.0, 2.0 Hz, 1H), 7.06 (dd, J=8.2, 1.8 Hz, 1H), 4.41 (d, 2H); HREIMS calcd for C₇H₅Br₂F m/z (M⁺) 269.8701, 267.8722, 265.8742, found 269.8692, 267.8713, 265.8726.

Reaction of bromide 86 (1.29 equiv.) with oxazine alcohol 41 as in Example 2N, followed by chromatography of the product on silica gel, eluting with 0-2% EtOAc/CH₂Cl₂ (foreruns) and then 2-4% EtOAc/CH₂Cl₂ gave (6S)-6-[(4-bromo-3-fluorobenzyl)oxy]-2-nitro-6,7-dihydro-5H-imidazo[2,1-b][1,3]oxazine (87) (89%) as a pale yellow solid: mp (MeOH/CH₂Cl₂/hexane) 181-183° C.; ¹H NMR [(CD₃)₂SO] δ 8.01 (s, 1H), 7.68 (dd, J=8.0, 7.5 Hz, 1H), 7.30 (dd, J=9.8, 1.9 Hz, 1H), 7.12 (dd, J=8.2, 1.5 Hz, 1H), 4.70-4.60 (m, 3H), 4.47 (br d, J=11.7 Hz, 1H), 4.31-4.18 (m, 3H). Anal. (C₁₃H₁₁BrFN₃O₄) C, H, N.

A stirred mixture of bromide 87 (503 mg, 1.35 mmol), 4-(trifluoromethoxy)phenylboronic acid (44) (500 mg, 2.43 mmol) and Pd(dppf)Cl₂ (304 mg, 0.415 mmol) in toluene (16 mL) and EtOH (8 mL) was degassed for 12 min (vacuum pump) and then N₂ was added. An aqueous solution of 2M Na₂CO₃ (3.6 mL, 7.2 mmol) was added by syringe and the stirred mixture was again degassed for 12 min, and then N₂ was added. The resulting mixture was stirred at 90° C. for 6 h, and then cooled, diluted with aqueous NaHCO₃ (100 mL) and extracted with CH₂Cl₂ (6×100 mL). The extracts were evaporated to dryness and the residue was chromatographed on silica gel. Elution with 0-1% EtOAc/CH₂Cl₂ firstly gave foreruns, and then further elution with 2% EtOAc/CH₂Cl₂ gave 15 (478 mg, 78%) as a pale yellow solid: mp (CH₂Cl₂/pentane) 181-183° C.; ¹H NMR (CDCl₃) δ 7.55 (dtd, J=8.8, 2.4, 1.5 Hz, 2H), 7.42 (t, J=7.9 Hz, 1H), 7.40 (s, 1H), 7.29 (br dd, J=8.8, 0.9 Hz, 2H), 7.17 (dd, J=7.8, 1.6 Hz, 1H), 7.13 (dd, J=11.0, 1.4 Hz, 1H), 4.77 (d, J=12.2 Hz, 1H), 4.68-4.62 (m, 2H), 4.38 (dd, J=12.2, 1.5 Hz, 1H), 4.26-4.14 (m, 3H). Anal. (C₂₀H₁₅F₄N₃O₅) C, H, N.

S. Synthesis of (6S)-2-nitro-6-({2-[4-(trifluoromethoxy)phenyl]-5-pyrimidinyl}methoxy)-6,7-dihydro-5H-imidazo[2,1-b][1,3]oxazine (16) by the method of Scheme 12

16

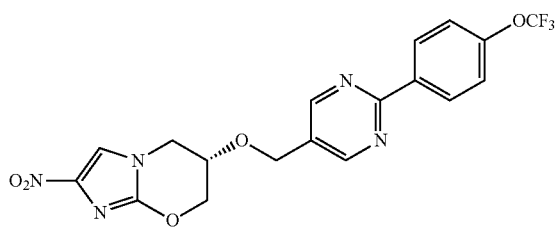

A mixture of 5-bromo-2-iodopyrimidine (88) (1.50 g, 5.27 mmol), 4-(trifluoromethoxy)phenylboronic acid (44) (1.185 g, 5.75 mmol) and Na₂CO₃ (1.11 g, 10.5 mmol) in toluene (120 mL) and water (15 mL) was purged with N₂. Pd(PPh₃)₄ (60 mg, 0.05 mmol) was added and the mixture was refluxed under N₂ for 17.5 h, then partitioned between EtOAc and water. Column chromatography of the organic portion on silica gel (eluting with 4:1 hexanes/CH₂Cl₂) gave 5-bromo-2-[4-(trifluoromethoxy)phenyl]pyrimidine (89) (1.264 g, 75%) as a white solid: mp 107-108° C.; ¹H NMR (CDCl₃) δ 8.83 (s, 2H), 8.46 (d, J=9.0 Hz, 2H), 7.31 (d, J=9.0 Hz, 2H). APCI MS m/z 319, 321 [M+H]⁺.

n-BuLi (2.5 M, 1.88 mL, 4.7 mmol) was added to a solution of bromide 89 (1.252 g, 3.92 mmol) in THF (40 mL) at −95° C. The solution was stirred for 30 s and then DMF (5 mL) was added. The reaction was stirred at −90° C. for 20 min and then quenched with aqueous NH₄Cl. The resulting mixture was partitioned between EtOAc and water, and then column chromatography of the organic portion on silica gel (eluting with 1:7 EtOAc/hexanes) gave 2-[4-(trifluoromethoxy)phenyl]-5-pyrimidinecarbaldehyde (90) (0.778 g, 74%) as a white solid: mp 114-115° C.; ¹H NMR (CDCl₃) δ 10.16 (s, 1H), 9.22 (s, 2H), 8.62 (d, J=9.0 Hz, 2H), 7.36 (d, J=9.0 Hz, 2H). APCI MS m/z 269 [M+H]⁺, 301 [M+H+MeOH]⁺.

NaBH₄ (0.22 g, 5.82 mmol) was added to a solution of aldehyde 90 (0.776 g, 2.89 mmol) in MeOH (100 mL) at 0° C. The solution was stirred at 0° C. for 1 h, then quenched with brine and partitioned between EtOAc and water. Column chromatography of the organic portion on silica gel (eluting with 1:1 EtOAc/hexanes) gave {2-[4-(trifluoromethoxy)phenyl]-5-pyrimidinyl}methanol (91) (0.657 g, 84%) as a white solid: mp 84-85° C.; ¹H NMR [(CD₃)₂SO] δ 8.86 (s, 2H), 8.50 (d, J=8.9 Hz, 2H), 7.51 (d, J=8.9 Hz, 2H), 5.46 (t, J=5.5 Hz, 1H), 4.60 (d, J=5.5 Hz, 2H). APCI MS m/z 271 [M+H]⁺.

Mesyl chloride (0.55 mL, 7.0 mmol) was added to a solution of alcohol 91 (0.951 g, 3.52 mmol) and Et₃N (1.5 mL, 10.8 mmol) in THF (40 mL) at 0° C. and the mixture was stirred at 0° C. for 1 h. The mixture was partitioned between EtOAc and water, and the organic layer was dried and evaporated to give an oil, which was dissolved in acetone (100 mL). LiBr (6.10 g, 70.2 mmol) was added and the mixture was refluxed under N₂ for 1 h, then filtered and evaporated. The residue was partitioned between EtOAc and water, and the organic layer was dried and evaporated. Column chromatography on silica gel (eluting with CH₂Cl₂) gave 5-(bromomethyl)-2-[4-(trifluoromethoxy)phenyl]pyrimidine (92) (1.097 g, 94%) as a white solid: mp 80-81° C.; ¹H NMR (CDCl₃) δ 8.82 (s, 2H), 8.50 (d, J=9.0 Hz, 2H), 7.32 (d, J=9.0 Hz, 2H), 4.48 (s, 2H). APCI MS m/z 333, 335 [M+H]⁺.

NaH (60% w/w, 0.125 g, 3.1 mmol) was added to a solution of oxazine alcohol 41 (0.375 g, 2.03 mmol) and bromide 92 (0.709 g, 2.13 mmol) in DMF (30 mL) at −78° C. The stirred mixture was warmed to 0° C. for 1 h, quenched with water and partitioned between EtOAc and water. Column chromatography of the organic portion on silica gel (eluting with 19:1 EtOAc/MeOH) gave 16 (0.512 g, 58%) as a white solid: mp 227-230° C. (MeOH); ¹H NMR [(CD₃)₂SO] δ 8.88 (s, 2H), 8.49 (d, J=8.9 Hz, 2H), 8.03 (s, 1H), 7.51 (d, J=8.9 Hz, 2H), 4.79 (d, J=12.6 Hz, 1H), 4.76 (d, J=12.6 Hz, 1H), 4.70 (dt, J=12.0, 2.5 Hz, 1H), 4.49 (br d, J=12.0 Hz, 1H), 4.29-4.35 (m, 2H), 4.25 (dd, J=13.3, 3.1 Hz, 1H). Anal. ($C_{18}H_{14}F_3N_5O_5$) C, H, N.

T. Synthesis of (6S)-2-nitro-6-({4-[4-(trifluoromethoxy)benzyl]benzyl}oxy)-6,7-dihydro-5H-imidazo[2,1-b][1,3]oxazine (17) by the method of Scheme 13

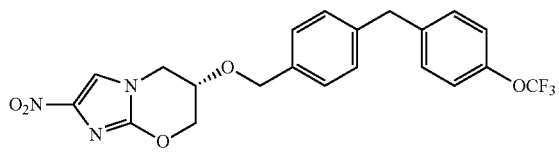

A solution of methyl 4-(bromomethyl)benzoate (93) (0.23 mL, 1.0 mmol) and 4-(trifluoromethoxy)phenylboronic acid (44) (0.24 g, 1.1 mmol) in DME (3 mL) and 2M aqueous $K_2CO_3$ (1 mL) was degassed, then treated with tetrakis(triphenylphosphine) palladium (58 mg, 50 µmol). The reaction mixture was stirred under $N_2$ at 105° C. for 24 h, and then EtOAc (250 mL) was added. The organic layer was washed with water, the aqueous layer was re-extracted with EtOAc (100 mL), and the combined organic layers were washed with brine, dried ($Na_2SO_4$) and concentrated under reduced pressure. The residue was chromatographed on silica gel, eluting with petroleum ether/EtOAc (9:1), to give methyl 4-[4-(trifluoromethoxy)benzyl]benzoate (94) (215 mg, 68%) as a colourless oil; $^1$H NMR (CDCl$_3$) δ 7.98-7.94 (m, 2H), 7.26-7.22 (m, 2H), 7.20-7.12 (m, 4H), 4.03 (s, 2H), 3.90 (s, 3H); HREIMS calcd for $C_{16}H_{13}F_3O_3$ m/z (TO 310.0817, found 310.0815.

LiAlH$_4$ (55 mg, 1.45 mmol) was added to a solution of ester 94 (203 mg, 0.65 mmol) in ether (5 mL) and the mixture was stirred at room temperature for 3 h, then EtOAc (150 mL) was added. The organic layer was washed with water, the aqueous layer was re-extracted with EtOAc (100 mL), and the combined organic layers were washed with brine, dried ($Na_2SO_4$) and concentrated under reduced pressure to give {4-[4-(trifluoromethoxy)benzyl]phenyl}methanol (95) (185 mg, quant.) as a white solid: mp (EtOAc/hexane) 60-61° C.; $^1$H NMR (CDCl$_3$) δ 7.32-7.27 (m, 2H), 7.20-7.14 (m, 4H), 7.13-7.09 (m, 2H), 4.67 (s, 2H), 3.98 (s, 2H); HREIMS calcd for $C_{15}H_{13}F_3O_2$ m/z (M$^+$) 282.0868, found 282.0866.

A solution of alcohol 95 (0.18 g, 0.64 mmol) in CH$_2$Cl$_2$ (4 mL) was treated with PBr$_3$ (115 µL 1.2 mmol). The reaction mixture was stirred at room temperature for 2 h, then EtOAc (150 mL) was added. The organic layer was washed with water (100 mL), the aqueous layer was re-extracted with EtOAc (100 mL), and the combined organic layers were washed with brine (100 mL), dried ($Na_2SO_4$) and concentrated under reduced pressure. The residue was chromatographed on silica gel, eluting with petroleum ether/EtOAc (9:1), to give 1-(bromomethyl)-4-[4-(trifluoromethoxy)benzyl]benzene (96) (0.14 g, 64%) as a white solid: mp (EtOAc/hexane) 33-35° C.; $^1$H NMR (CDCl$_3$) δ 7.34-7.30 (m, 2H), 7.20-7.10 (m, 6H), 4.48 (s, 2H), 3.97 (s, 2H); HREIMS calcd for $C_{15}H_{12}^{79}BrF_3O$ m/z (M$^+$) 344.0024, found 344.0033; calcd for $C_{15}H_{12}^{81}BrF_3O$ m/z (M$^+$) 346.0003, found 346.0011.

A solution of bromide 96 (0.12 g, 0.35 mmol) and alcohol 41 (54 mg, 0.29 mmol) in DMF (2 mL) was treated with NaH (60% in oil, 17 mg, 0.43 mmol) and the mixture was stirred at room temperature for 3 h, then EtOAc (150 mL) was added. The organic layer was washed with water (100 mL), the aqueous layer was re-extracted with EtOAc (100 mL), and the combined organic layers were washed with brine (100 mL), dried ($Na_2SO_4$) and concentrated under reduced pressure. The residue was chromatographed on silica gel, eluting with 0-3% MeOH/CH$_2$Cl$_2$, to give 17 (95 mg, 73%) as a light yellow solid: mp (CH$_2$Cl$_2$/MeOH) 132-133° C.; $^1$H NMR [(CD$_3$)$_2$SO] δ 8.00 (s, 1H), 7.35-7.30 (m, 2H), 7.28-7.19 (m, 6H), 4.63 (dt, J=11.9, 2.3 Hz, 1H), 4.61 (d, J=11.8 Hz, 1H), 4.57 (d, J=11.8 Hz, 1H), 4.45 (d, J=11.9 Hz, 1H), 4.27-4.17 (m, 3H), 3.96 (s, 2H). Anal. ($C_{21}H_{18}F_3N_3O_5$) C, H, N.

U. Synthesis of (6S)-2-nitro-6-[(5-{[4-(trifluoromethoxy)phenyl]ethynyl}-2-pyridinyl)methoxy]-6,7-dihydro-5H-imidazo[2,1-b][1,3]oxazine (18) by the method of Scheme 14

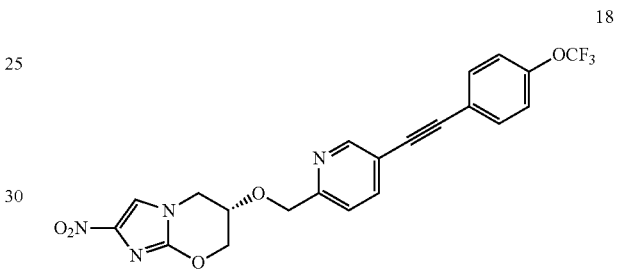

A mixture of bromide 59 (see Example 21) (0.310 g, 0.873 mmol), PdCl$_2$(PPh$_3$)$_2$ (33 mg, 0.047 mmol) and copper iodide (18 mg, 0.095 mmol) in DMF (4 mL) and Et$_3$N (4 mL) was purged with N$_2$. Ethynyltrimethylsilane (0.61 mL, 4.3 mmol) was added and the mixture was stirred in a sealed tube at 50° C. for 18 h, and then partitioned between EtOAc and water. The residue was dissolved in THF (20 mL), cooled to 0° C. and treated with TBAF (1M in THF, 1.8 mL), and then the solution was stirred for 2 h. Removal of the solvent gave a residue which was partitioned between EtOAc and water. Column chromatography of the organic portion on silica gel using gradient elution (0-5% MeOH:EtOAc) gave (6S)-6-[(5-ethynyl-2-pyridinyl)methoxy]-2-nitro-6,7-dihydro-5H-imidazo[2,1-b][1,3]oxazine (97) (0.178 g, 68%) as a tan solid: mp 135-136° C.; $^1$H NMR [(CD$_3$)$_2$SO] δ 8.61 (d, J=1.6 Hz, 1H), 8.02 (s, 1H), 7.90 (dd, J=8.0, 2.2 Hz, 1H), 7.38 (d, J=8.0 Hz, 1H), 4.78 (d, J=13.8 Hz, 1H), 4.74 (d, J=13.8 Hz, 1H), 4.69 (dt, J=12.0, 2.6 Hz, 1H), 4.49 (d, J=12.0 Hz, 1H), 4.40 (s, 1H), 4.30-4.35 (m, 2H), 4.25 (dd, J=13.7, 3.5 Hz, 1H). Anal. ($C_{14}H_{12}N_4O_4$) C, H, N.

A mixture of alkyne 97 (0.075 g, 0.25 mmol), 1-iodo-4-(trifluoromethoxy)benzene (70) (0.088 g, 0.30 mmol) and copper iodide (5 mg, 0.03 mmol) in DMF (2 mL) and Et$_3$N (2 mL) was purged with N$_2$. PdCl$_2$(PPh$_3$)$_2$ (9 mg, 0.01 mmol) was added and the mixture was stirred at room temperature for 0.5 h, and then partitioned between EtOAc and water. Column chromatography of the organic portion on silica gel using gradient elution (0-5% MeOH:EtOAc) gave 18 (0.084 g, 73%) as a white solid: mp 207-208° C.; $^1$H NMR [(CD$_3$)$_2$SO] δ 8.71 (d, J=1.7 Hz, 1H), 8.03 (s, 1H), 7.99 (dd, J=8.1, 2.2 Hz, 1H), 7.73 (d, J=8.9 Hz, 2H), 7.42-7.47 (m, 3H), 4.81 (d, J=13.9 Hz, 1H), 4.77 (d, J=13.9 Hz, 1H), 4.71 (dt, J=12.0, 2.5 Hz, 1H), 4.51 (d, J=11.9 Hz, 1H), 4.31-4.37 (m, 2H), 4.26 (dd, J=13.7, 3.5 Hz, 1H). Anal. (C$_{21}$H$_{15}$F$_3$N$_4$O$_5$) C, H, N.

V. Synthesis of (6S)-2-nitro-6-[(5-{[6-(trifluoromethyl)-3-pyridinyl]ethynyl}-2-pyridinyl)methoxy]-6,7-dihydro-5H-imidazo[2,1-b][1,3]oxazine (25) by the method of Scheme 14

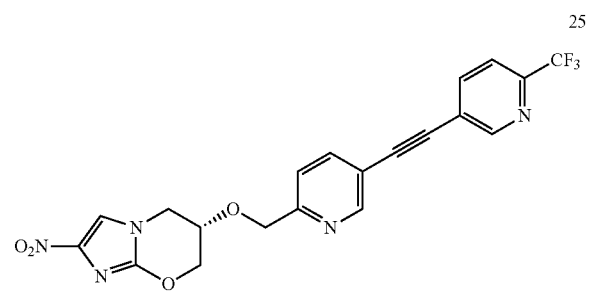 [SMILES: O=[N+]([O-])c1cn2c(n1)OC[C@@H](OCc1ccc(C#Cc3ccc(C(F)(F)F)nc3)cn1)C2]

Sonogashira coupling of alkyne 97 (see Example 2U) (0.075 g, 0.25 mmol) and 5-bromo-2-(trifluoromethyl)pyridine (98) (0.068 g, 0.30 mmol) as in Example 2U, at 50° C. for 0.5 h, gave 25 (0.086 g, 77%) as a white solid: mp 226-227° C.; $^1$H NMR [(CD$_3$)$_2$SO] δ 8.97 (d, J=1.3 Hz, 1H), 8.78 (d, J=1.4 Hz, 1H), 8.30 (dd, J=8.0, 1.4 Hz, 1H), 8.06 (dd, J=8.1, 2.2 Hz, 1H), 8.04 (s, 1H), 8.00 (d, J=8.2 Hz, 1H), 7.43 (d, J=8.2 Hz, 1H), 4.83 (d, J=13.9 Hz, 1H), 4.79 (d, J=13.9 Hz, 1H), 4.72 (dt, J=12.0, 2.5 Hz, 1H), 4.51 (d, J=11.9 Hz, 1H), 4.32-4.38 (m, 2H), 4.26 (dd, J=13.8, 3.5 Hz, 1H). Anal. (C$_{20}$H$_{14}$F$_3$N$_5$O$_4$) C, H, N.

W. Synthesis of (6S)-2-nitro-6-({(2E)-3-[4'-(trifluoromethoxy)[1,1'-biphenyl]-4-yl]-2-propenyl}oxy)-6,7-dihydro-5H-imidazo[2,1-b][1,3]oxazine (19) by the method of Scheme 15

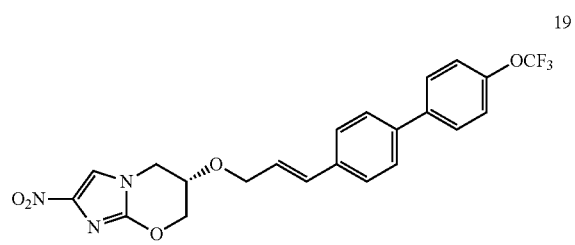 [SMILES: O=[N+]([O-])c1cn2c(n1)OC[C@@H](OC/C=C/c1ccc(-c3ccc(OC(F)(F)F)cc3)cc1)C2]

A solution of methyl (E)-3-(4-bromophenyl)-2-propenoate (99) (0.500 g, 2.07 mmol) and 4-(trifluoromethoxy)phenylboronic acid (44) (0.612 g, 2.97 mmol) in dioxane (40 mL) and aqueous K$_2$CO$_3$ (2M, 10 mL, 20 mmol) was purged with N$_2$. Pd(dppf)Cl$_2$ (0.050 g, 0.06 mmol) was added and the solution was refluxed under N$_2$ for 1 h. The dioxane was removed and the residue was extracted with EtOAc, the organic fraction was dried and the solvent was removed. Column chromatography of the residue on silica gel using gradient elution (hexanes to CH$_2$Cl$_2$) gave methyl (2E)-3-[4'-(trifluoromethoxy)[1,1'-biphenyl]-4-yl]-2-propenoate (100) (0.567 g, 85%) as a white solid: mp 98-100° C.; $^1$H NMR (CDCl$_3$) δ 7.73 (d, J=16.0 Hz, 1H), 7.56-7.63 (m, 6H), 7.30 (dd, J=8.8, 0.9 Hz, 2H), 6.48 (d, J=16.0 Hz, 1H), 3.82 (s, 3H). APCI MS m/z 323 [M+H]$^+$.

DIBAL-H (20% w/w in toluene, 2 mL, 2.39 mmol) was added to a slurry of ester 100 (0.396 g, 1.23 mmol) in toluene (12 mL) at −78° C. The mixture was warmed to room temperature, stirred for 1 h, and then poured onto ice cold NH$_4$Cl solution (50 mL). The mixture was diluted with CH$_2$Cl$_2$ (100 mL), filtered through Celite and the organic layer was dried and evaporated. Column chromatography of the residue on silica gel using gradient elution (CH$_2$Cl$_2$ to 95:5 CH$_2$Cl$_2$: EtOAc) gave (2E)-3-[4'-(trifluoromethoxy)[1,1'-biphenyl]-4-yl]-2-propen-1-ol (101) (0.195 g, 54%) as a white solid: mp 121-123° C.; NMR (CDCl$_3$) δ 7.60 (d, J=8.7 Hz, 2H), 7.53 (d, J=8.4 Hz, 2H), 7.47 (d, J=8.4 Hz, 2H), 7.28 (d, J=8.1 Hz, 2H), 6.66 (d, J=15.9 Hz, 1H), 6.42 (dt, J=15.9, 5.7 Hz, 1H), 4.36 (dd, J=5.9, 5.7 Hz, 2H), 1.44 (t, J=5.9 Hz, 1H). APCI MS m/z 307 [M−H−H$_2$O+MeOH]$^-$.

PBr$_3$ (26 μL, 0.28 mmol) was added to a solution of alcohol 101 (0.159 g, 0.540 mmol) in Et$_2$O (10 mL) at 0° C. The mixture was warmed to room temperature and stirred for 1 h, then quenched with ice and extracted with Et$_2$O. The organic fraction was dried and evaporated, and then column chromatography of the residue on silica gel (eluting with CH$_2$Cl$_2$) gave 4-[(1E)-3-bromo-1-propenyl]-4'-(trifluoromethoxy)-1,1'-biphenyl (102) (0.123 g, 71%) as a white solid: mp 121-123° C.; $^1$H NMR (CDCl$_3$) δ 7.60 (d, J=8.8 Hz, 2H), 7.53 (d, J=8.4 Hz, 2H), 7.46 (d, J=8.4 Hz, 2H), 7.28 (d, J=8.8 Hz, 2H), 6.69 (d, J=15.6 Hz, 1H), 6.45 (dt, J=15.6, 7.8 Hz, 1H), 4.18 (dd, J=7.8, 0.9 Hz, 2H). APCI MS m/z 277 [M+H−HBr]$^+$.

NaH (60% w/w, 0.016 g, 0.40 mmol) was added to a solution of oxazine alcohol 41 (0.050 g, 0.27 mmol) and bromide 102 (0.100 g, 0.28 mmol) in DMF (6 mL) at −78° C. The mixture was stirred at 0° C. for 1 h, then quenched with ice and partitioned between EtOAc and water. The organic fraction was dried and evaporated, and then column chromatography of the residue on silica gel using gradient elution (1:1 hexanes:EtOAc to EtOAc) gave 19 (0.079 g, 63%) as a white solid: mp 220-221° C.; $^1$H NMR [(CD$_3$)$_2$SO] δ 8.04 (s, 1H), 7.80 (d, J=8.8 Hz, 2H), 7.66 (d, J=8.4 Hz, 2H), 7.55 (d, J=8.4 Hz, 2H), 7.44 (d, J=8.8 Hz, 2H), 6.66 (d, J=16.0 Hz, 1H), 6.43 (dt, J=16.0, 5.9 Hz, 1H), 4.65 (d, J=11.9 Hz, 1H), 4.48 (d, J=11.9 Hz, 1H), 4.21-4.35 (m, 5H). Anal. (C$_{22}$H$_{18}$F$_3$N$_3$O$_5$) C, H, N.

X. Synthesis of (6S)-2-nitro-6,7-dihydro-5H-imidazo[2,1-b][1,3]oxazin-6-yl 4-[4-(trifluoromethoxy)phenyl]-1-piperazinecarboxylate (20) by the method of Scheme 16

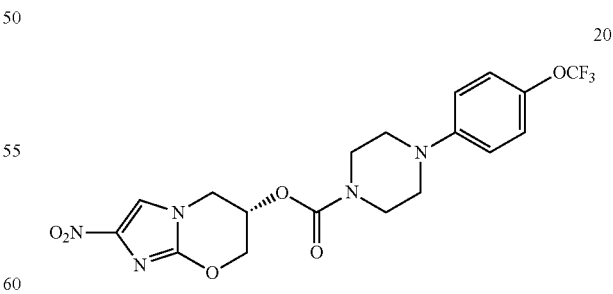

Triphosgene (0.80 g, 2.70 mmol) was added in portions with stirring to an ice bath cooled suspension of the oxazine alcohol 41 (1.00 g, 5.40 mmol) and Et$_3$N (1.12 mL, 8.10 mmol) in anhydrous THF (30 mL). After 15 min the ice bath was removed and the suspension was stirred at room temperature for 90 min to give a solution of the crude carbonyl chloride 103. A solution of 1-[4-(trifluoromethoxy)phenyl]piperazine (104) (1.40 g, 5.67 mmol) in THF (10 mL) was then added and stirring was continued for 2 h. Water was added and the mixture was extracted with EtOAc. Evaporation of this extract gave an oily solid, which was chromatographed on silica. Elution with EtOAc/petroleum ether (1:1) gave fore fractions, and then further elution with EtOAc gave 20 (1.53 g, 62%) as a yellow powder, following trituration with ether: mp 166-168° C.; $^1$H NMR [(CD$_3$)$_2$SO] δ 8.06 (s, 1H), 7.19 (d, J=9.0 Hz, 2H), 6.99 (d, J=9.0 Hz, 2H), 5.32 (br s, 1H), 4.62-4.55 (m, 2H), 4.39 (dd, J=13.9, 3.5 Hz, 1H), 4.27 (br d, J=13.9 Hz, 1H), 3.45 (br m, 4H), 3.13 (br m, 4H). Anal. (C$_{18}$H$_{18}$F$_3$N$_5$O$_6$) C, H, N.

Y. Synthesis of (6S)-6-({5-[3-fluoro-4-(trifluoromethoxy)phenyl]-2-pyridinyl}methoxy)-2-nitro-6,7-dihydro-5H-imidazo[2,1-b][1,3]oxazine (22) by the method of Scheme 17

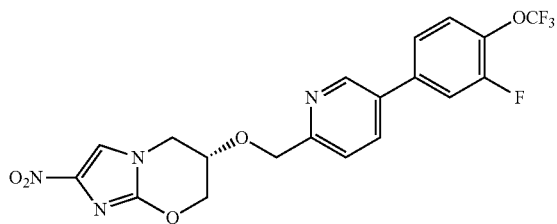

22

A stirred mixture of (5-bromo-2-pyridinyl)methanol (105) (753 mg, 4.00 mmol), 3-fluoro-4-(trifluoromethoxy)phenylboronic acid (56) (see Example 2G) (1.165 g, 5.20 mmol) and Pd(dppf)Cl$_2$ (366 mg, 0.50 mmol) in toluene (40 mL) and EtOH (20 mL) was degassed for 15 min (vacuum pump) and then N$_2$ was added. An aqueous solution of 2M Na$_2$CO$_3$ (10 mL, 20.0 mmol) was added by syringe and the stirred mixture was again degassed for 15 min, and then N$_2$ was added. The resulting mixture was stirred at 89° C. for 2 h, and then cooled, diluted with aqueous NaHCO$_3$ (120 mL) and extracted with CH$_2$Cl$_2$ (6×100 mL). The extracts were evaporated to dryness and the residue was chromatographed on silica gel. Elution with 50-75% CH$_2$Cl$_2$/petroleum ether firstly gave foreruns, and then further elution with 75% CH$_2$Cl$_2$/petroleum ether and 0-0.5% MeOH/CH$_2$Cl$_2$ gave {5-[3-fluoro-4-(trifluoromethoxy)phenyl]-2-pyridinyl}methanol (106) (687 mg, 60%) as a light yellow-brown solid: mp 51-53° C.; $^1$H NMR (CDCl$_3$) δ 8.76 (d, J=1.9 Hz, 1H), 7.84 (dd, J=8.1, 2.3 Hz, 1H), 7.46-7.34 (m, 4H), 4.83 (d, J=5.1 Hz, 2H), 3.47 (t, J=5.2 Hz, 1H); HRESIMS calcd for C$_{13}$H$_{10}$F$_4$NO$_2$ m/z [M+H]$^+$ 288.0642, found 288.0641.

A solution of alcohol 106 (678 mg, 2.36 mmol) and triphenylphosphine (746 mg, 2.84 mmol) in anhydrous CH$_2$Cl$_2$ (30 mL) was carefully treated with recrystallized N-bromosuccinimide (507 mg, 2.85 mmol) (water bath cooling), and the mixture was stirred at room temperature for 3 h. The resulting solution was concentrated, and then added to excess petroleum ether at the top of a silica gel column (25 g in petroleum ether), rinsing on with minimal extra CH$_2$Cl$_2$. Elution with petroleum ether firstly gave foreruns, and then further elution with 10-20% Et$_2$O/pentane gave 2-(bromomethyl)-5-[3-fluoro-4-(trifluoromethoxy)phenyl]pyridine (107) (616 mg, 75%) as a white solid that was used directly in the next step; $^1$H NMR (CDCl$_3$) δ 8.76 (dd, J=2.4, 0.6 Hz, 1H), 7.84 (dd, J=8.1, 2.4 Hz, 1H), 7.54 (dd, J=8.0, 0.6 Hz, 1H), 7.46-7.33 (m, 3H), 4.60 (s, 2H); HRESIMS calcd for C$_{13}$H$_9$BrF$_4$NO m/z [M+H]$^+$ 351.9778, 349.9798, found 351.9778, 349.9798.

A solution of oxazine alcohol 41 (311 mg, 1.68 mmol) and bromide 107 (614 mg, 1.75 mmol) in anhydrous DMF (6.5 mL) under N$_2$ at 0° C. was treated with 60% NaH (88.5 mg, 2.21 mmol), then quickly degassed and resealed under N$_2$. After stirring at room temperature for 2.5 h, the reaction was cooled (CO$_2$/acetone), quenched with ice/aqueous NaHCO$_3$ (20 mL), added to brine (40 mL) and extracted with CH$_2$Cl$_2$ (8×50 mL). The combined extracts were evaporated to dryness and the residue was chromatographed on silica gel. Elution with 0-0.75% MeOH/CH$_2$Cl$_2$ firstly gave foreruns, and then further elution with 0.75-1.5% MeOH/CH$_2$Cl$_2$ gave 22 (676 mg, 89%) as a light yellow solid: mp (CH$_2$Cl$_2$/pentane) 182-184° C.; $^1$H NMR (CDCl$_3$) δ 8.74 (dd, J=2.3, 0.7 Hz, 1H), 7.86 (dd, J=8.1, 2.4 Hz, 1H), 7.48-7.38 (m, 4H), 7.35 (ddd, J=8.4, 2.2, 1.0 Hz, 1H), 4.87 (d, J=13.0 Hz, 1H), 4.81 (d, J=13.0 Hz, 1H), 4.70 (ddd, J=12.2, 3.5, 1.5 Hz, 1H), 4.40 (dd, J=12.2, 1.4 Hz, 1H), 4.33-4.20 (m, 3H). Anal. (C$_{19}$H$_{14}$F$_4$N$_4$O$_5$) C, H, N.

Z. Synthesis of (6S)-2-nitro-6-({6-[4-(trifluoromethoxy)phenyl]-3-pyridazinyl}methoxy)-6,7-dihydro-5H-imidazo[2,1-b][1,3]oxazine (24) by the method of Scheme 18

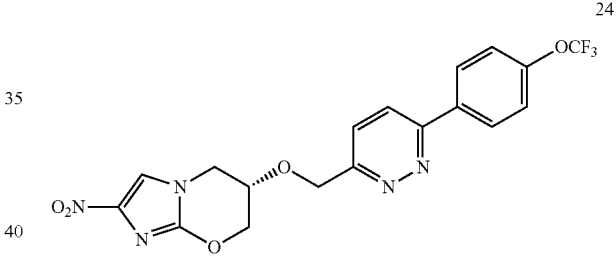

24

NaH (60% w/w, 0.304 g, 7.60 mmol) was added to a solution of oxazine alcohol 41 (0.893 g, 4.82 mmol) in DMF (20 mL) at 0° C. The resulting solution was cooled to −42° C. and a solution of 3-(bromomethyl)-6-chloropyridazine (108) (obtained via free radical bromination of 3-chloro-6-methylpyridazine, as reported in EP 1555259) (1.053 g, 5.08 mmol) in DMF (5 mL) was added. The mixture was stirred at −42° C. for 1 h and then quenched with ice. EtOAc (200 mL) was added and the organic layer was dried (MgSO$_4$) and then concentrated under reduced pressure. The residue was chromatographed on silica gel, initially eluting with hexanes/EtOAc (1:1) to remove unreacted 3-(bromomethyl)-6-chloropyridazine and then with EtOAc to give (6S)-6-[(6-chloro-3-pyridazinyl)methoxy]-2-nitro-6,7-dihydro-5H-imidazo[2,1-b][1,3]oxazine (109) (0.843 g, 56%) as a white solid: mp 180-184° C.; $^1$H NMR [(CD$_3$)$_2$SO] δ 8.02 (s, 1H), 7.93 (d, J=8.8 Hz, 1H), 7.74 (d, J=8.8 Hz, 1H), 4.97 (d, J=13.2 Hz, 1H), 4.94 (d, J=13.2 Hz, 1H), 4.69 (dt, J=12.0, 2.6 Hz, 1H), 4.50 (d, J=12.1 Hz, 1H), 4.30-4.39 (m, 2H), 4.25 (dd, J=13.5, 3.3 Hz, 1H). Anal. (C$_{11}$H$_{10}$ClN$_5$O$_4$) C, H, N.

Suzuki coupling of chloride 109 and 4-(trifluoromethoxy)phenylboronic acid (44) as in Example 2D gave 24 (66%) as a white solid: mp 194° C. (dec.); $^1$H NMR [(CD$_3$)$_2$SO] δ 8.25-8.30 (m, 3H), 8.03 (s, 1H), 7.76 (d, J=8.9 Hz, 1H), 7.55 (d, J=8.9 Hz, 2H), 5.04 (d, J=13.2 Hz, 1H), 5.00 (d, J=13.2

Hz, 1H), 4.74 (dt, J=12.0, 2.6 Hz, 1H), 4.52 (d, J=11.9 Hz, 1H), 4.33-4.43 (m, 2H), 4.28 (dd, J=13.5, 3.3 Hz, 1H). Anal. ($C_{18}H_{14}F_3N_5O_5$) C, H, N.

AA. Synthesis of (6S)-6-{[4-(5-fluoro-2-pyridinyl)benzyl]oxy}-2-nitro-6,7-dihydro-5H-imidazo[2,1-b][1,3]oxazine (26) by the method of Scheme 19

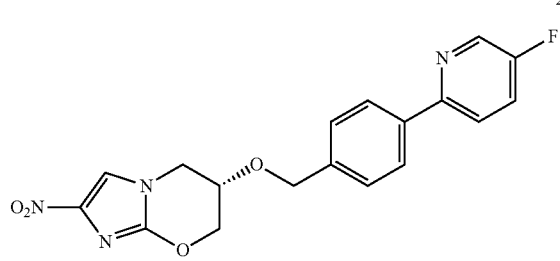

26

A stirred mixture of 4-(hydroxymethyl)phenylboronic acid (34) (501 mg, 3.30 mmol) and Pd(dppf)Cl$_2$ (338 mg, 0.462 mmol) in toluene (36 mL) and EtOH (18 mL) was degassed for 15 min (vacuum pump) and then N$_2$ was added. An aqueous solution of 2M Na$_2$CO$_3$ (9 mL, 18 mmol) was added by syringe and the stirred mixture was again degassed for 15 min, and then N$_2$ was added. 2-Bromo-5-fluoropyridine (110) (1.44 g, 8.18 mmol) was added by syringe and the resulting mixture was stirred at 89° C. for 200 min. The cooled mixture was then diluted with aqueous NaHCO$_3$ (100 mL) and extracted with CH$_2$Cl$_2$ (5×100 mL). The extracts were evaporated to dryness and the residue was chromatographed on silica gel. Elution with CH$_2$Cl$_2$ and 0-25% Et$_2$O/petroleum ether firstly gave foreruns, and then further elution with 33-50% Et$_2$O/petroleum ether gave [4-(5-fluoro-2-pyridinyl)phenyl]methanol (111) (307 mg, 46%) as a cream solid (following pentane trituration): mp 100-101° C.; $^1$H NMR (CDCl$_3$) δ 8.54 (d, J=2.9 Hz, 1H), 7.94 (dt, J=8.4, 1.9 Hz, 2H), 7.72 (ddd, J=8.8, 4.2, 0.5 Hz, 1H), 7.50-7.43 (m, 3H), 4.76 (d, J=6.0 Hz, 2H), 1.69 (t, J=6.0 Hz, 1H); HRESIMS calcd for $C_{12}H_{11}FNO$ m/z [M+H]$^+$ 204.0819, found 204.0824.

A solution of alcohol 111 (305 mg, 1.50 mmol) and triphenylphosphine (474 mg, 1.81 mmol) in anhydrous CH$_2$Cl$_2$ (12 mL) was carefully treated with recrystallized N-bromosuccinimide (322 mg, 1.81 mmol) (water bath cooling), and the mixture was stirred at room temperature for 3 h. The resulting solution was concentrated, and then added to excess pentane at the top of a silica gel column (20 g in pentane), rinsing on with minimal extra CH$_2$Cl$_2$. Elution with pentane firstly gave foreruns, and then further elution with 20-50% Et$_2$O/pentane gave 2-[4-(bromomethyl)phenyl]-5-fluoropyridine (112) (348 mg, 87%) as a white solid that was used directly in the next step; $^1$H NMR (CDCl$_3$) δ 8.54 (d, J=2.9 Hz, 1H), 7.92 (dt, J=8.4, 1.9 Hz, 2H), 7.72 (ddd, J=8.7, 4.3, 0.4 Hz, 1H), 7.52-7.43 (m, 3H), 4.54 (s, 2H); HRESIMS calcd for $C_{12}H_{10}BrFN$ m/z [M+H]$^+$ 267.9955, 265.9975, found 267.9959, 265.9979.

A solution of oxazine alcohol 41 (242 mg, 1.31 mmol) and bromide 112 (346 mg, 1.30 mmol) in anhydrous DMF (5 mL) under N$_2$ at 0° C. was treated with 60% NaH (70 mg, 1.75 mmol), then quickly degassed and resealed under N$_2$. After stirring at room temperature for 135 min, the reaction was cooled (CO$_2$/acetone), quenched with ice/aqueous NaHCO$_3$ (20 mL), added to brine (100 mL) and extracted with CH$_2$Cl$_2$ (9×100 mL). The combined extracts were evaporated to dryness and the residue was chromatographed on silica gel. Elution with 0-6% EtOAc/CH$_2$Cl$_2$ firstly gave foreruns, and then further elution with 7-10% EtOAc/CH$_2$Cl$_2$ gave the crude product, which was further chromatographed on silica gel. Elution with petroleum ether and 50-67% EtOAc/petroleum ether firstly gave foreruns, and then further elution with 30% EtOAc/CH$_2$Cl$_2$ gave 26 (357 mg, 74%) as a cream solid: mp (CH$_2$Cl$_2$/pentane) 180-181° C.; $^1$H NMR (CDCl$_3$) δ 8.54 (d, J=2.9 Hz, 1H), 7.95 (dt, J=8.4, 1.9 Hz, 2H), 7.72 (ddd, J=8.8, 4.2, 0.4 Hz, 1H), 7.48 (ddd, J=8.7, 8.1, 2.9 Hz, 1H), 7.41 (br d, J=8.4 Hz, 2H), 7.37 (s, 1H), 4.79 (d, J=12.2 Hz, 1H), 4.68 (d, J=12.2 Hz, 1H), 4.61 (ddd, J=12.1, 3.7, 1.9 Hz, 1H), 4.35 (dd, J=12.1, 1.5 Hz, 1H), 4.20-4.09 (m, 3H). Anal. ($C_{18}H_{15}FN_4O_4$) C, H, N.

BB. Synthesis of (6S)-2-nitro-6-({1-[4-(trifluoromethoxy)phenyl]-1H-pyrazol-4-yl}methoxy)-6,7-dihydro-5H-imidazo[2,1-b][1,3]oxazine (27) by the method of Scheme 20

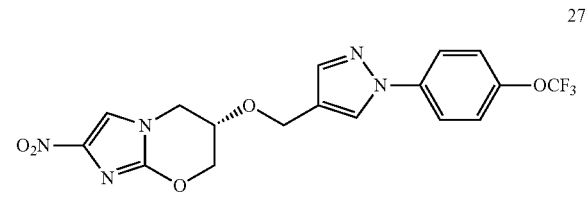 [SMILES: O=[N+]([O-])c1cn2c(n1)OC[C@@H](OCc1cnn(-c3ccc(OC(F)(F)F)cc3)c1)C2]

27

A mixture of ethyl (2E)-2-cyano-3-ethoxy-2-propenoate (113) (1.87 g, 11.1 mmol), 4-(trifluoromethoxy)phenylhydrazine hydrochloride (114) (2.286 g, 10.00 mmol) and NaOAc (0.90 g, 11.0 mmol) in AcOH (7.5 mL) and water (2.5 mL) was heated to 100° C. under N$_2$ for 15 h. The mixture was poured onto ice, and the resulting precipitate was filtered and recrystallised (MeOH/water) to give ethyl 5-amino-1-[4-(trifluoromethoxy)phenyl]-1H-pyrazole-4-carboxylate (115) (2.965 g, 94%) as white flakes: mp 102-103° C.; $^1$H NMR [(CD$_3$)$_2$SO] δ 7.73 (s, 1H), 7.68 (d, J=9.1 Hz, 2H), 7.53 (d, J=9.1 Hz, 2H), 6.41 (br s, 2H), 4.22 (q, J=7.1 Hz, 2H), 1.27 (t, J=7.1 Hz, 3H). APCI MS m/z 316 [M+H]$^+$.

A solution of aminopyrazole 115 (1.850 g, 5.87 mmol) and isoamyl nitrite (0.83 mL, 6.18 mmol) in THF (20 mL) was refluxed for 14 h, then further isoamyl nitrite (0.83 mL, 6.18 mmol) was added and the solution was refluxed for 6 h. The solvent was removed under reduced pressure to give a solid, which was recrystallised (EtOH) to give ethyl 1-[4-(trifluoromethoxy)phenyl]-1H-pyrazole-4-carboxylate (116) (1.527 g, 87%) as white flakes: mp 114-116° C.; $^1$H NMR (CDCl$_3$) δ 8.38 (d, J=0.5 Hz, 1H), 8.10 (s, 1H), 7.74 (d, J=9.1 Hz, 2H), 7.34 (d, J=9.1 Hz, 2H), 4.35 (q, J=7.1 Hz, 2H), 1.38 (t, J=7.1 Hz, 3H). APCI MS m/z 301 [M+H]$^+$.

A mixture of ester 116 (0.730 g, 2.43 mmol) and LiAlH$_4$ (0.200 g, 5.28 mmol) in Et$_2$O (20 mL) was refluxed for 2 h. The mixture was cooled to 0° C., quenched with ice, diluted with Et$_2$O (100 mL) and filtered through Celite. The organic layer was dried (MgSO$_4$), then column chromatography on silica gel (19:1 CH$_2$Cl$_2$:EtOAc) gave {1-[4-(trifluoromethoxy)phenyl]-1H-pyrazol-4-yl}methanol (117) (0.520 g, 83%) as a white solid: mp 73-74° C.; $^1$H NMR (CDCl$_3$) δ 7.91 (s, 1H), 7.67-7.73 (m, 3H), 7.31 (d, J=8.4 Hz, 2H), 4.69 (d, J=5.5 Hz, 2H), 1.57 (t, J=5.5 Hz, 1H). APCI MS m/z 259 [M+H]$^+$.

PBr$_3$ (76 μL, 0.81 mmol) was added to a solution of alcohol 117 (0.210 g, 0.813 mmol) in ether (10 mL) at 0° C. The mixture was stirred at room temperature for 2 h, then cooled to 0° C., quenched with ice, and partitioned between Et₂O and water. Column chromatography of the organic portion on silica gel (eluting with CH₂Cl₂) gave 4-(bromomethyl)-1-[4-(trifluoromethoxy)phenyl]-1H-pyrazole (118) (0.212 g, 81%) as a white solid: mp 50-51° C.; $^1$H NMR (CDCl₃) δ 7.94 (d, J=0.5 Hz, 1H), 7.74 (s, 1H), 7.69 (d, J=9.1 Hz, 2H), 7.31 (d, J=9.1 Hz, 2H), 4.50 (s, 2H). APCI MS m/z 321, 323 [M+H]⁺.

NaH (60% w/w, 30 mg, 0.75 mmol) was added to a solution of oxazine alcohol 41 (0.091 g, 0.49 mmol) and bromide 118 (0.157 g, 0.49 mmol) in DMF (10 mL) at 0° C. The mixture was stirred for 2 h, quenched with ice, and partitioned between EtOAc and water. Column chromatography of the organic portion on silica gel, eluting with a gradient of 1:1 hexanes:EtOAc to EtOAc, gave 27 (0.148 g, 71%) as a white solid: mp 150-151° C.; $^1$H NMR [(CD₃)₂SO] δ 8.53 (s, 1H), 8.02 (s, 1H), 7.93 (d, J=9.1 Hz, 2H), 7.77 (s, 1H), 7.50 (d, J=9.1 Hz, 2H), 4.56-4.66 (m, 3H), 4.46 (d, J=11.8 Hz, 1H), 4.20-4.26 (m, 3H). Anal. (C₁₇H₁₄F₃N₅O₅) C, H, N.

CC. Synthesis of (6S)-2-nitro-6-({5-[4-(trifluoromethoxy)phenyl]-2-pyrimidinyl}methoxy)-6,7-dihydro-5H-imidazo[2,1-b][1,3]oxazine (29) by the method of Scheme 21

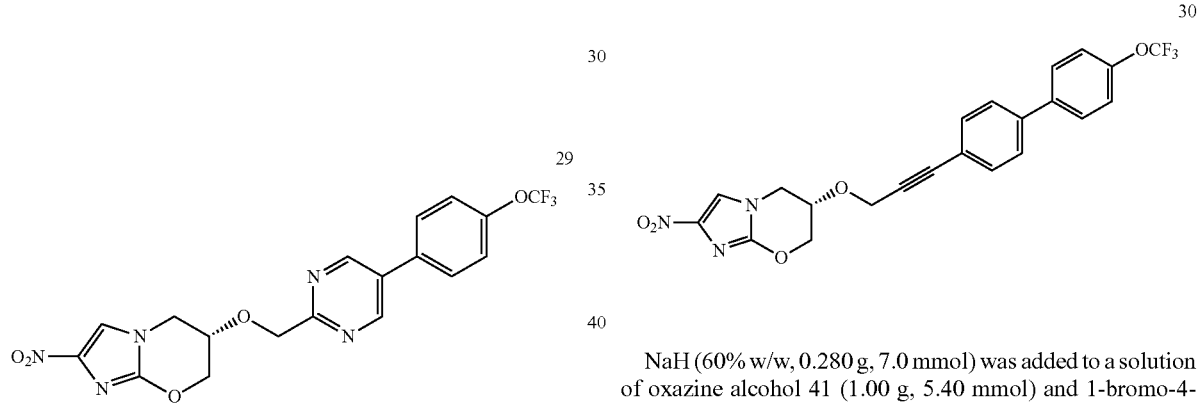

A mixture of 5-bromo-2-methylpyrimidine (119) (1.34 g, 7.75 mmol), N-bromosuccinimide (1.40 g, 7.87 mmol) and AIBN (0.13 g, 0.79 mmol) in CCl₄ (15 mL) was stirred at 60° C. for 3 h. The resulting mixture was filtered, the filter cake was washed with Et₂O (100 mL), and the combined filtrates were concentrated under reduced pressure. Column chromatography of the residue, eluting with 2:1 EtOAc:hexanes, gave 5-bromo-2-(bromomethyl)pyrimidine (120) (0.214 g, 11%) as a white solid: mp 55-57° C.; $^1$H NMR (CDCl₃) δ 8.79 (s, 2H), 4.57 (s, 2H). Anal. (C₅H₄Br₂N₂) C, H, N.

NaH (60% w/w, 0.170 g, 4.25 mmol) was added to a solution of bromide 120 (0.879 g, 3.49 mmol) and alcohol 41 (0.520 g, 2.81 mmol) in anhydrous DMF (10 mL) at −78° C. The mixture was stirred at 0° C. for 0.5 h and then quenched with ice and extracted with EtOAc (200 mL). The organic layer was dried (MgSO₄) and evaporated, and then column chromatography of the residue using gradient elution (0-5% MeOH/EtOAc) gave (6S)-6-[(5-bromo-2-pyrimidinyl)methoxy]-2-nitro-6,7-dihydro-5H-imidazo[2,1-b][1,3]oxazine (121) (0.510 g, 51%) as a light brown solid: mp>290° C.; $^1$H NMR [(CD₃)₂SO] δ 8.98 (s, 2H), 8.03 (s, 1H), 4.83 (d, J=13.2 Hz, 1H), 4.80 (d, J=13.2 Hz, 1H), 4.68 (dt, J=12.0, 2.6 Hz, 1H), 4.48 (br d, J=11.9 Hz, 1H), 4.40-4.36 (m, 1H), 4.31 (dt, J=13.5, 2.1 Hz, 1H), 4.23 (dd, J=13.5, 3.3 Hz, 1H). Anal. (C₁₁H₁₀BrN₅O₄) C, H, N: calcd, 19.67; found, 19.17.

Suzuki coupling of bromide 121 and 4-(trifluoromethoxy)phenylboronic acid (44) as in Example 2D gave 29 (89%) as a white solid: mp 223-226° C.; $^1$H NMR [(CD₃)₂SO] δ 9.14 (s, 2H), 8.05 (s, 1H), 7.93 (d, J=8.8 Hz, 2H), 7.53 (d, J=8.8 Hz, 2H), 4.91 (d, J 14.5 Hz, 1H), 4.87 (d, J=14.5 Hz, 1H), 4.72 (dt, J=11.9, 2.6 Hz, 1H), 4.51 (br d, J=12.0 Hz, 1H), 4.45-4.42 (m, 1H), 4.35 (dt, J=13.5, 2.1 Hz, 1H), 4.27 (dd, J=13.5, 3.3 Hz, 1H). Anal. (C₁₈H₁₄F₃N₅O₅) C, H, N.

DD. Synthesis of (6S)-2-nitro-6-({3-[4'-(trifluoromethoxy)[1,1'-biphenyl]-4-yl]-2-propynyl}oxy)-6,7-dihydro-5H-imidazo[2,1-b][1,3]oxazine (30) by the method of Scheme 22

NaH (60% w/w, 0.280 g, 7.0 mmol) was added to a solution of oxazine alcohol 41 (1.00 g, 5.40 mmol) and 1-bromo-4-(3-bromo-1-propynyl)benzene (122) (prepared in two steps from 1-bromo-4-iodobenzene and propargyl alcohol, as described in WO 9524400) (1.57 g, 5.73 mmol) in DMF (25 mL) at 0° C. The mixture was stirred at 0° C. for 1 h, and then quenched with water and extracted with EtOAc. The organic fraction was dried and the solvent was removed, and then column chromatography of the residue on silica gel using gradient elution (1:1 hexanes:EtOAc to EtOAc) gave (6S)-6-{[3-(4-bromophenyl)-2-propynyl]oxy}-2-nitro-6,7-dihydro-5H-imidazo[2,1-b][1,3]oxazine (123) (1.58 g, 77%) as a white solid: mp 160-162° C.; $^1$H NMR [(CD₃)₂SO] δ 8.03 (s, 1H), 7.60 (d, J=8.6 Hz, 2H), 7.42 (d, J=8.6 Hz, 2H), 4.66 (dt, J=12.1, 2.4 Hz, 1H), 4.57 (s, 2H), 4.49 (d, J=12.1 Hz, 1H), 4.37-4.40 (m, 1H), 4.30 (dt, J=13.7, 2.0 Hz, 1H), 4.25 (dd, J=13.7, 3.2 Hz, 1H). Anal. (C₁₅H₁₂BrN₃O₄) C, H, N.

Suzuki coupling of bromide 123 and 4-(trifluoromethoxy)phenylboronic acid (44) as in Example 2D followed by column chromatography of the product on silica gel using gradient elution (1:1 hexanes: EtOAc to EtOAc) gave 30 (72%) as a white solid: mp 192-194° C.; $^1$H NMR [(CD₃)₂SO] δ 8.04 (s, 1H), 7.83 (d, J=8.8 Hz, 2H), 7.72 (d, J=8.4 Hz, 2H), 7.58 (d, J=8.4 Hz, 2H), 7.46 (d, J=8.8 Hz, 2H), 4.68 (dt, J=12.1, 2.4 Hz, 1H), 4.61 (s, 2H), 4.51 (d, J=12.0 Hz, 1H), 4.39-4.42 (m, 1H), 4.32 (dt, J=13.6, 2.0 Hz, 1H), 4.27 (dd, J=13.6, 3.2 Hz, 1H). Anal. ($C_{22}H_{16}F_3N_3O_5$) C, H, N.

EE. Synthesis of (6S)-2-nitro-6-[(4-{(E)-2-[4-(trifluoromethoxy)phenyl]ethenyl}benzyl)oxy]-6,7-dihydro-5H-imidazo[2,1-b][1,3]oxazine (31) by the method of Scheme 23

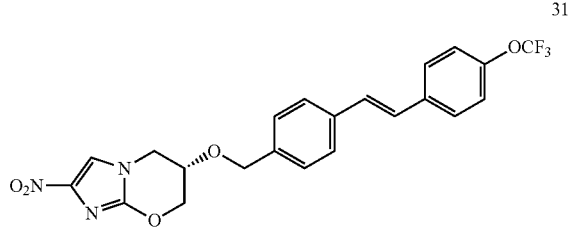 [SMILES: O=[N+]([O-])c1cn2c(n1)OC[C@@H](OCc1ccc(/C=C/c3ccc(OC(F)(F)F)cc3)cc1)C2]

31

4-(Trifluoromethoxy)benzaldehyde (125) (0.928 g, 4.88 mmol), $K_2CO_3$ (2.8 g, 20 mmol) and 18-crown-6 (0.04 g, 0.15 mmol) were added to a solution of [4-(methoxycarbonyl)benzyl]triphenylphosphonium bromide (124) (2.00 g, 4.07 mmol) in THF (60 mL) and $CH_2Cl_2$ (40 mL). The mixture was refluxed under $N_2$ for 18 h, and then partitioned between EtOAc and water. The organic layer was washed with brine and the solvent was removed. Column chromatography of the residue on silica gel, eluting with 19:1 hexanes:EtOAc, gave a crude product which was recrystallised from hexanes to give methyl 4-{(E)-2-[4-(trifluoromethoxy)phenyl]ethenyl}benzoate (126) (0.549 g, 42%) as white flakes: mp (hexanes) 120-122° C.; NMR (CDCl$_3$) δ 8.03 (d, J=8.4 Hz, 2H), 7.51-7.58 (m, 4H), 7.16-7.24 (m, 3H), 7.09 (d, J=16.3 Hz, 1H), 3.93 (s, 3H). APCI MS m/z 323 [M+H]$^+$.

LiAH$_4$ (0.039 g, 1.03 mmol) was added to a solution of ester 126 (0.166 g, 0.515 mmol) in Et$_2$O (10 mL) at 0° C. The mixture was stirred at room temperature for 0.5 h, and then cooled to 0° C., quenched with ice, and filtered through Celite. The organic fraction was dried and evaporated, and then column chromatography of the residue, eluting with 95:5 CH$_2$Cl$_2$:MeOH, gave (4-{(E)-2-[4-(trifluoromethoxy)phenyl]ethenyl}phenyl)methanol (127) (0.182 g, 82%) as a white solid: mp 161-163° C.; $^1$H NMR [(CD$_3$)$_2$SO] δ 7.78 (d, J=8.8 Hz, 2H), 7.57 (d, J=8.2 Hz, 2H), 7.31-7.38 (m, 4H), 7.27 (s, 2H), 5.16 (t, J=5.7 Hz, 1H), 4.51 (d, J=5.7 Hz, 2H). APCI MS m/z 277 [M+H–H$_2$O]$^+$.

PBr$_3$ (56 μL, 0.60 mmol) was added to a solution of alcohol 127 (0.177 g, 0.601 mmol) in anhydrous CH$_2$Cl$_2$ (10 mL) at 0° C. The mixture was stirred at room temperature for 1 h, and then cooled to 0° C., quenched with ice, and extracted with CH$_2$Cl$_2$. The organic fraction was dried, and evaporated, and then column chromatography of the residue, eluting with CH$_2$Cl$_2$, gave 1-{(E)-2-[4-(bromomethyl)phenyl]ethenyl}-4-(trifluoromethoxy)benzene (128) (0.125 g, 58%) as a white solid: mp 100-102° C.; $^1$H NMR (CDCl$_3$) δ 7.52 (d, J=8.6 Hz, 2H), 7.48 (d, J=8.3 Hz, 2H), 7.39 (d, J=8.3 Hz, 2H), 7.20 (br d, J=8.1 Hz, 2H), 7.10 (d, J=16.3 Hz, 1H), 7.05 (d, J=16.3 Hz, 1H), 4.51 (s, 2H). APCI MS m/z 277 [M+H–HBr]$^+$.

NaH (60% w/w, 0.010 g, 0.25 mmol) was added to a solution of alcohol 41 (0.024 g, 0.13 mmol) and bromide 128 (0.056 g, 0.16 mmol) in anhydrous DMF (5 mL) at −78° C. The mixture was then stirred at 0° C. for 1 h, quenched with water, and extracted with EtOAc. The organic fraction was dried and evaporated, and then column chromatography using gradient elution (1:1 hexanes:EtOAc to EtOAc) gave 31 (0.043 g, 72%) as a white solid: mp 228-230° C.; $^1$H NMR [(CD$_3$)$_2$SO] δ 8.02 (s, 1H), 7.72 (d, J=8.8 Hz, 2H), 7.59 (d, J=8.2 Hz, 2H), 7.27-7.38 (m, 6H), 4.61-4.70 (m, 3H), 4.47 (d, J=11.9 Hz, 1H), 4.20-4.31 (m, 3H). Anal. ($C_{22}H_{18}F_3N_3O_5$) C, H, N.

FF. Synthesis of (6S)-2-nitro-6-[(4-{[4-(trifluoromethoxy)phenyl]ethynyl}benzyl)oxy]-6,7-dihydro-5H-imidazo[2,1-b][1,3]oxazine (32) by the method of Scheme 24

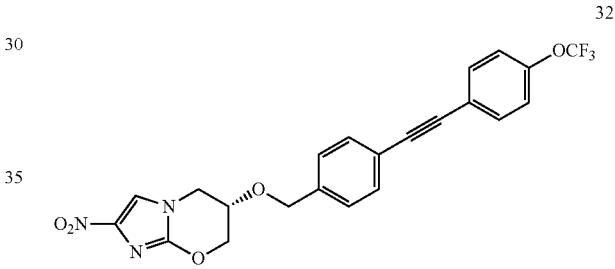

32

A mixture of iodide 43 (see Example 2C) (1.00 g, 2.49 mmol) and copper iodide (51 mg, 0.27 mmol) in DMF (10 mL) and Et$_3$N (10 mL) was purged with N$_2$. Ethynyltrimethylsilane (1.0 mL, 7.1 mmol) and PdCl$_2$(PPh$_3$)$_2$ (93 mg, 0.13 mmol) were added and the mixture was stirred under N$_2$ for 0.5 h. The resulting mixture was partitioned between EtOAc and water, the organic fraction was dried, and the solvent was removed. The residue was dissolved in THF (50 mL) and tetra-n-butylammonium fluoride (5 mL of a 1M solution in THF, 5 mmol) was added. The solution was stirred for 2 h and then concentrated. The residue was partitioned between EtOAc and water, and the organic fraction was dried and concentrated. Column chromatography of the residue on silca gel using gradient elution (1:1 hexanes EtOAc to EtOAc) gave (6S)-6-[(4-ethynylbenzyl)oxy]-2-nitro-6,7-dihydro-5H-imidazo[2,1-b][1,3]oxazine (129) (0.530 g, 71%) as a white solid: mp 162-164° C.; $^1$H NMR [(CD$_3$)$_2$SO] δ 8.01 (s, 1H), 7.45 (d, J=8.3 Hz, 2H), 7.32 (d, J=8.3 Hz, 2H), 4.62-4.71 (m, 3H), 4.47 (d, J=11.9 Hz, 1H), 4.20-4.30 (m, 3H), 4.14 (s, 1H). Anal. ($C_{15}H_{13}N_3O_4$) C, H, N.

Sonogashira coupling of alkyne 129 and 1-iodo-4-(trifluoromethoxy)benzene (70) as in Example 2U, followed by column chromatography of the product on silica gel using gradient elution (1:1 hexanes: EtOAc to EtOAc), gave 32 (72%) as a white solid: mp 233-236° C.; $^1$H NMR [(CD$_3$)$_2$SO] δ 8.03 (s, 1H), 7.69 (d, J=8.9 Hz, 2H), 7.55 (d, J=8.3 Hz, 2H), 7.42

(d, J=8.9 Hz, 2H), 7.37 (d, J=8.3 Hz, 2H), 4.62-4.73 (m, 3H), 4.48 (d, J=11.9 Hz, 1H), 4.22-4.32 (m, 3H). Anal. ($C_{22}H_{16}F_3N_3O_5$) C, H, N.

GG. Synthesis of (6S)-2-nitro-6-[(6-{[4-(trifluoromethoxy)phenyl]ethynyl}-3-pyridinyl)methoxy]-6,7-dihydro-5H-imidazo[2,1-b][1,3]oxazine (33) by the method of Scheme 24

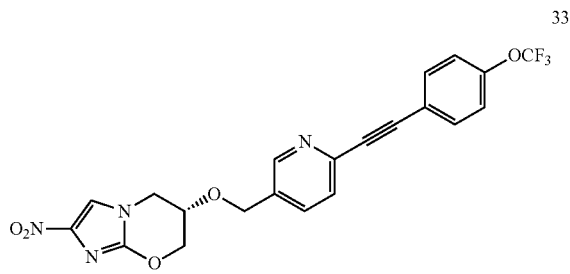 [SMILES: O=[N+]([O-])c1cn2c(n1)OC[C@@H](OCc1ccc(C#Cc3ccc(OC(F)(F)F)cc3)nc1)C2]

Sonogashira coupling of bromide 52 (see Example 2F) (0.310 g, 0.873 mmol) and ethynyltrimethylsilane (0.61 mL, 4.3 mmol) at room temperature for 18 h, followed by desilylation with TBAF, as in Example 2U, gave (6S)-6-[(6-ethynyl-3-pyridinyl)methoxy]-2-nitro-6,7-dihydro-5H-imidazo[2,1-b][1,3]oxazine (130) (0.150 g, 57%) as a white solid: mp 168-170° C.; $^1$H NMR [$(CD_3)_2SO$] δ 8.51 (d, J=1.6 Hz, 1H), 8.02 (s, 1H), 7.74 (dd, J=8.0, 2.2 Hz, 1H), 7.54 (dd, J=8.0, 0.6 Hz, 1H), 4.73 (d, J=12.6 Hz, 1H), 4.70 (d, J=12.6 Hz, 1H), 4.67 (dt, J=12.3, 2.3 Hz, 1H), 4.47 (d, J=11.9 Hz, 1H), 4.29 (s, 1H), 4.20-4.28 (m, 3H). APCI MS m/z 301 [M+H]$^+$.

Sonogashira coupling of alkyne 130 and 1-iodo-4-(trifluoromethoxy)benzene (70) as in Example 2U gave 33 (55%) as a white solid: mp 235-238° C.; $^1$H NMR [$(CD_3)_2SO$] δ 8.56 (d, J=1.7 Hz, 1H), 8.03 (s, 1H), 7.72-7.82 (m, 3H), 7.65 (d, J=7.9 Hz, 1H), 7.45 (d, J=8.0 Hz, 2H), 4.76 (d, J=12.7 Hz, 1H), 4.72 (d, J=12.7 Hz, 1H), 4.69 (dt, J=12.0, 2.3 Hz, 1H), 4.49 (d, J=11.9 Hz, 1H), 4.22-4.32 (m, 3H). Anal. ($C_{21}H_{15}F_3N_4O_5$) C, H, N.

EXAMPLE 3

Physicochemical Properties, Stability, and Biological Activities

The physicochemical properties of the compounds of the invention were evaluated as follows. Results are shown below in Table 2.

(a) Calculated Lipophilicity (CLOGP).

These were calculated using Log P/log D prediction software from ACD/Labs (version 8.0, Advanced Chemistry Development, Inc., Toronto, Ontario, Canada).

(b) Water Solubility.

The solid compound sample was mixed with water (enough to make a 2 mM solution) in an Eppendorf tube and the suspension was sonicated for 15 min, and then centrifuged at 13,000 rpm for 6 min. An aliquot of the clear supernatant was diluted 2-fold with water, and then HPLC was conducted. The solubility was calculated by comparing the peak area obtained with that from a standard solution of the compound in DMSO (after allowing for varying dilution factors and injection volumes).

The microsomal stability and in vitro biological activity of the compounds of the invention was also evaluated, with results shown in Table 2.

(a) Minimum Inhibitory Concentrations (MICs).

Compounds were evaluated for their activity against replicating *Mycobacterium tuberculosis* in an 8 day microplate-based assay using Alamar blue reagent (added on day 7) for determination of growth (MABA) (Collins et al., 1997; Falzari et al., 2005). The lowest compound concentration effecting an inhibition of >90% was considered the MIC. Screening for the activity of the compounds against bacteria in the non-replicating state that models clinical persistence used an 11 day high-throughput, luminescence-based low-oxygen-recovery assay (LORA), where *M. tuberculosis* bacteria containing a plasmid with an acetamidase promoter driving a bacterial luciferase gene were first adapted to low oxygen conditions by extended culture (Cho et al., 2007).

(b) Stability of the Compounds to Human and Mouse Microsomes.

Test compounds (1 μM) were incubated at 37° C. with pooled human or CD-1 mouse liver microsome preparations (0.5 mg/mL final protein concentration) and an NADPH regenerating system ($MgCl_2$, 3.3 mM; G6P, 3.3 mM; G6PD, 0.4 U/mL; NADP+, 1.3 mM) in phosphate buffer (75 mM, pH 7.4), with a final volume of 200 μL. The compounds were dissolved in DMSO such that the final DMSO concentration was 0.5%. Reactions were stopped at 0 and 60 min by the addition of MeCN (100 μL) containing 0.2 μM metoprolol as an internal standard. Samples were diluted 10× and centrifuged prior to analysis by LC-MS/MS using electrospray ionization and SRM monitoring using a gradient LC method. LC peak areas were integrated and expressed as analyte/IS peak area ratios (PAR), and a mean value for each time point was calculated from the duplicates. The percent remaining value was calculated as:

% remaining=100×(Mean $PAR_{T60}$/Mean $PAR_{T0}$).

TABLE 2

Physicochemistry, microsomal stability and in vitro biological activity of the compounds of Table 1

| No | Physicochemistry | | MIC (μM) | | Microsomes (% remaining, 1 h) | |
|---|---|---|---|---|---|---|
| | LOGP (calc) | Solubility (μg/mL) | MABA (aerobic) | LORA (anaerobic) | Human | Mouse |
| PA-824 | 2.70 | 19 | 0.50 | 2.6 | 82 | 94 |
| 1 | 5.07 | 0.66 | 0.04 | 0.78 | 91 | 86 |
| 2 | 4.33 | 0.1 | 0.03 | 0.34 | 93 | 86 |
| 3 | 4.36 | 1.2 | 0.035 | 1.3 | 97 | 96 |
| 4 | 2.19 | 2.6 | 0.023 | 1.0 | 98 | 91 |
| 5 | 2.10 | 3.8 | 0.06 | 2.9 | 88 | 80 |
| 6 | 3.01 | 2.3 | 0.05 | 0.54 | 83 | 87 |
| 7 | 3.04 | 2.5 | 0.065 | 3.7 | 97 | 97 |
| 8 | 3.54 | 0.20 | 0.06 | 1.0 | 93 | 90 |
| 9 | 3.57 | 1.0 | 0.03 | 2.1 | 86 | 91 |
| 10 | 2.60 | 2.7 | 0.05 | 0.61 | 87 | 67 |
| 11 | 2.46 | 5.3 | 0.06 | 0.58 | 86 | 81 |
| 12 | 4.38 | 1.4 | 0.017 | 1.2 | 93 | 85 |
| 13 | 3.98 | 3.0 | 0.05 | 1.3 | 99 | 97 |
| 14 | 3.56 | 1.2 | 0.055 | 2.3 | 90 | 77 |
| 15 | 4.87 | 0.33 | 0.055 | 0.51 | 97 | 91 |
| 16 | 3.05 | 2.1 | 0.027 | 1.8 | 96 | 87 |
| 17 | 4.69 | 0.16 | 0.02 | 1.1 | 85 | 70 |
| 18 | 3.77 | 0.36 | 0.02 | 1.4 | 98 | 97 |
| 19 | 4.83 | 0.50 | 0.063 | >64 | 100 | 95 |
| 20 | 1.56 | 17 | 0.13 | 1.1 | 82 | 85 |
| 21 | 2.99 | 3.0 | 0.025 | 0.93 | 100 | 90 |
| 22 | 3.02 | 30 | 0.05 | 1.3 | 97 | 86 |
| 23 | 3.59 | 5.7 | 0.13 | 0.68 | 96 | 78 |
| 24 | 1.52 | 6.1 | 0.075 | 1.7 | 94 | 92 |

TABLE 2-continued

Physicochemistry, microsomal stability and in vitro
biological activity of the compounds of Table 1

| | Physicochemistry | | MIC (μM) | | Microsomes (% remaining, 1 h) | |
|---|---|---|---|---|---|---|
| | LOGP | Solubility | MABA | LORA | | |
| No | (calc) | (μg/mL) | (aerobic) | (anaerobic) | Human | Mouse |
| 25 | 2.30 | | 0.035 | 0.74 | 88 | 91 |
| 26 | 2.09 | 67 | 0.035 | 1.3 | 83 | 61 |
| 27 | 2.60 | | 0.15 | 1.8 | 87 | 64 |
| 28 | 3.53 | 0.18 | 0.017 | 1.0 | 87 | 77 |
| 29 | 2.63 | 8.1 | 0.11 | 1.9 | 92 | 87 |
| 30 | 5.60 | 0.07 | 0.16 | 0.99 | 93 | 85 |
| 31 | 5.35 | | 0.02 | 27 | 99 | 98 |
| 32 | 5.26 | | 0.017 | >128 | | |
| 33 | 3.77 | | 0.02 | 0.94 | | |

The in vivo biological activity of the compounds of the invention was evaluated in two assays, and pharmacokinetic parameters were also determined, with results shown below in Table 3.

(a) In Vivo Mouse Acute TB Infection Assay.

BALB/c mice were infected via aerosol with a suspension of ~2×10$^6$ colony forming units (CFU) of *M. tuberculosis* Erdman/mL (Falzari et al., 2005). Each compound was given orally to a group of 7 or 8 mice at 100 mg/kg daily for 5 days a week for 3 weeks, beginning on day 11 post-infection. Compounds were administered as a suspension in 0.5% CMC/0.08% Tween 80 in water. Mice were sacrificed on day 31 and the numbers of CFU in the lungs were determined and compared with the CFU for vehicle alone-treated mice at this time. PA-824 was employed as a positive control in each experiment, and the results are recorded as the ratio of the average reduction in CFU in the compound-treated mice/the average CFU reduction in the mice treated with PA-824. In this assay, PA-824 caused up to 2.5-3 log reductions in CFU.

(b) In Vivo Mouse Chronic TB Infection Assay.

Compounds were given orally as in (a) but with treatment beginning ~70 days after infection. In this assay, PA-824 caused a ~2 log reduction in CFU.

(c) In Vivo Pharmacokinetics.

Compounds were administered orally to CD-1 mice at a dose of 40 mg/kg, as a suspension in 0.5% carboxymethylcellulose/0.08% Tween 80 in water. Samples derived from plasma and lungs were analyzed by LC-MS/MS to generate the required pharmacokinetic parameters.

TABLE 3

In vivo pharmacokinetics and biological activity of selected compounds of Table 1

| | In vivo pharmacokinetics | | | | In vivo efficacy vs PA-824 | |
|---|---|---|---|---|---|---|
| | t½ (h) | Cmax plasma | AUC lung (μg · h/ | AUC ratio | | |
| No | plasma | (μg/mL) | mL) | (lung/plasma) | Acute | Chronic |
| PA-824 | 4.2 | 5.5 | 296 | 3.8 | 1.0 | 1.0 |
| 1 | 19.9 | 6.8 | 3363 | 17 | 23 | 2.1 |
| 2 | 20.5 | 17.1 | >513 | >1 | 419 | ND |
| 3 | 14.4 | 7.4 | 218 | 1.1 | >205 | 12 |
| 4 | 7.2 | 9.6 | >324 | >2.1 | 167 | ND |
| 5 | 2.7 | 5.3 | 136 | 2.2 | 7.8 | 20 |
| 6 | 24 | 12.2 | 81 | 0.27 | >89 | 15 |
| 7 | 5.4 | 25.9 | 427 | 1.0 | 27 | 0.9 |

TABLE 3-continued

In vivo pharmacokinetics and biological activity of selected compounds of Table 1

| | In vivo pharmacokinetics | | | | In vivo efficacy vs PA-824 | |
|---|---|---|---|---|---|---|
| | t½ (h) | Cmax plasma | AUC lung (μg · h/ | AUC ratio | | |
| No | plasma | (μg/mL) | mL) | (lung/plasma) | Acute | Chronic |
| 8 | 8.8 | 1.1 | 67.3 | 3.3 | 33 | 1.7 |
| 9 | ND | 13.5 | 414 | 1.9 | 15 | 4.6 |
| 10 | 2.4 | 1.51 | 31.5 | 3.5 | 41 | ND |
| 11 | 6.6 | 1.66 | 92.4 | 4.7 | 12 | 0.9 |
| 12 | 22 | 6.7 | 549 | 2.7 | 33 | 16 |
| 13 | 38 | 1.86 | 347 | 3.4 | 8.1 | ND |
| 14 | 13.9 | 0.44 | 148 | 16 | 52 | ND |
| 15 | ND | ND | ND | ND | >933 | ND |
| 16 | 23.1 | 1.16 | 131 | 3.0 | >1120 | ND |
| 18 | 23.5 | 2.36 | 235 | 2.5 | >933 | ND |
| 20 | 10.5 | 2.5 | 169 | 3.2 | 5.2 | ND |
| 21 | 13.9 | 7.0 | 251 | 1.4 | >840 | ND |
| 22 | 8.4 | 7.6 | 155 | 1.1 | 233 | ND |
| 23 | 4.9 | 1.56 | 55.4 | 2.5 | 8.8 | ND |
| 24 | 2.9 | 3.56 | 93.9 | 1.8 | 11 | ND |
| 28 | 21.7 | 2.89 | 284 | 3.2 | >933 | ND |
| 30 | 7.5 | 0.57 | 13.6 | 1.4 | 89 | 11 |
| 31 | ND | ND | ND | ND | 5.8 | ND |

REFERENCES CITED

The content of each of the documents listed below is hereby incorporated by reference.

U.S. Patent Documents

U.S. Pat. No. 5,668,127
U.S. Pat. No. 6,087,358

International Patent Documents

EP 1555259
WO 95/24400
WO 2007/075872

Non-Patent Publications

Anderson et al., *Org. Biomol. Chem.* 6, 1973-1980 (2008).
Cho et al., *Antimicrob. Agents Chemother.* 51, 1380-1385 (2007).
Collins et al., *Antimicrob. Agents Chemother.* 41, 1004-1009 (1997).
deSolms et al., *J. Med. Chem.* 46, 2973-2984 (2003).
Edsall et al., *Bioorg. Med. Chem.* 11, 3457-3474 (2003).
Falzari et al., *Antimicrob. Agents Chemother.* 49, 1447-1454 (2005).
Ferrara et al., *Lancet* 367, 1328-1334 (2006).
Kiener et al., *Synlett* 10, 814-816 (1994).
Kim et al., *J. Med. Chem.* 52, 1317-1328 and 1329-1344 (2009).
Li et al., *Bioorg. Med. Chem. Lett.* 18, 2256-2262 (2008).
Manjunatha et al., *Proc. Natl. Acad Sci. USA* 103, 431-436 (2006).
Sasaki et al., *J. Med. Chem.* 49, 7854-7860 (2006).
Schubert et al., *Synlett* 3, 342-344 (1999).
Singh et al., *Science* 322, 1392-1395 (2008).
Stover et al., *Nature* 405, 962-966 (2000).
Tyagi et al., *Antimicrob. Agents Chemother.* 49, 2289-2293 (2005).
van den Heuvel et al., *J. Org. Chem.* 69, 250-262 (2004).

What is claimed is:

1. A compound having a general structure of Formula I:

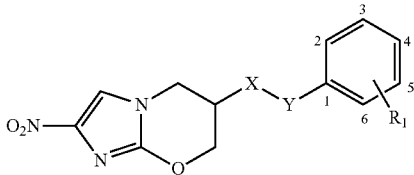

wherein X is O, OCH$_2$, OCH$_2$CH=CH or OCH$_2$C≡C,
numbers 1, 2, 3, 4, 5, and 6 are ring positions on a terminal ring of Formula I,
R$_1$ in Formula I is one or two substituents located at ring positions 2, 3, 4, 5, or 6 on the terminal ring, and is independently selected from the group consisting of F, Cl, CF$_3$, OCF$_2$H, and OCF$_3$,
Y is Formula IIa:

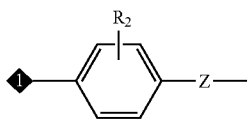

wherein ◆— is a direct single bond attachment to X, and
Z in Formula IIa is CH$_2$, CH=CH, C≡C or is itself a direct single bond through which the ring of Formula IIa is directly bonded to the terminal ring of Formula I, and
R$_2$ in Formula IIa is one or two substituents located at any available ring positions and is independently selected from the group consisting of H, F, and Cl.

2. The compound of claim 1 wherein:
X is O, OCH$_2$, OCH$_2$CH=CH or OCH$_2$C≡C,
numbers 1, 2, 3, 4, 5, and 6 are ring positions on a terminal ring of Formula I,
R$_1$ in Formula I is any one or more of F located at ring position 4, OCF$_3$ located at ring position 4, Cl located at ring position 2, Cl located at ring position 3, F located at ring position 3, or CF$_3$ located at ring position 4,
Y is Formula IIa:

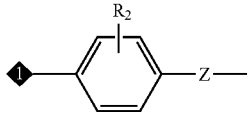

wherein ◆— is a direct single bond attachment to X, and
Z in Formula IIa is CH$_2$, CH=CH, C≡C or is itself a direct single bond through which the ring of Formula IIa is directly bonded to the terminal ring of Formula I, and
R$_2$ in Formula IIa is any one or two of H or F, located at any available ring position.

3. A pharmaceutical composition comprising a therapeutically effective amount of the compound of claim 1.

4. The pharmaceutical composition of claim 3, further comprising a pharmaceutically acceptable excipient, adjuvant, carrier, buffer or stabilizer.

5. The pharmaceutical composition of claim 3, further comprising one or more additional anti-infective treatments.

6. A compound selected from the group consisting of:
A) (6S)-6-{[2'-Chloro-4'-(trifluoromethoxy)[1,1'-biphenyl]-4-yl]methoxy}-2-nitro-6,7-dihydro-5H-imidazo[2,1-b][1,3]oxazine;
B) (6S)-6-{[3'-Fluoro-4'-(trifluoromethoxy)[1,1'-biphenyl]-4-yl]methoxy}-2-nitro-6,7-dihydro-5H-imidazo[2,1-b][1,3]oxazine;
C) (6S)-2-Nitro-6-{[4'-(trifluoromethoxy)[1,1'-biphenyl]-4-yl]methoxy}-6,7-dihydro-5H-imidazo[2,1-b][1,3]oxazine;
D) (6S)-6-{[6-(4-Fluorophenyl)-3-pyridinyl]methoxy}-2-nitro-6,7-dihydro-5H-imidazo[2,1-b][1,3]oxazine;
E) (6S)-2-Nitro-6-({6-[4-(trifluoromethoxy)phenyl]-3-pyridinyl}methoxy)-6,7-dihydro-5H-imidazo[2,1-b][1,3]oxazine;
F) (6S)-2-Nitro-6-({5-[4-(trifluoromethoxy)phenyl]-2-pyridinyl}methoxy)-6,7-dihydro-5H-imidazo[2,1-b][1,3]oxazine;
G) (6S)-2-Nitro-6-({4-[5-(trifluoromethyl)-2-pyridinyl]benzyl}oxy)-6,7-dihydro-5H-imidazo[2,1-b][1,3]oxazine;
H) (6S)-2-Nitro-6-({4-[6-(trifluoromethyl)-3-pyridinyl]benzyl}oxy)-6,7-dihydro-5H-imidazo[2,1-b][1,3]oxazine;
I) (6S)-6-{[3-Fluoro-4'-(trifluoromethoxy)[1,1'-biphenyl]-4-yl]methoxy}-2-nitro-6,7-dihydro-5H-imidazo[2,1-b][1,3]oxazine;
J) (6S)-2-Nitro-6-{[4'-(trifluoromethoxy)[1,1'-biphenyl]-4-yl]oxy}-6,7-dihydro-5H-imidazo[2,1-b][1,3]oxazine;
K) (6S)-6-({2-Fluoro-4-[5-(trifluoromethyl)-2-pyridinyl]benzyl}oxy)-2-nitro-6,7-dihydro-5H-imidazo[2,1-b][1,3]oxazine;
L) (6S)-6-{[2-Fluoro-4'-(trifluoromethoxy)[1,1'-biphenyl]-4-yl]methoxy}-2-nitro-6,7-dihydro-5H-imidazo[2,1-b][1,3]oxazine;
M) (6S)-2-Nitro-6-({4-[4-(trifluoromethoxy)benzyl]benzyl}oxy)-6,7-dihydro-5H-imidazo[2,1-b][1,3]oxazine;
N) (6S)-2-Nitro-6-[(5-{[4-trifluoromethoxy)phenyl]ethynyl}-2-pyridinyl)methoxy]-6,7-dihydro-5H-imidazo[2,1-b][1,3]oxazine;
O) (6S)-2-Nitro-6-({(2E)-3-[4'-(trifluoromethoxy)[1,1'-biphenyl]-4-yl]-2-propenyl}oxy)-6,7-dihydro-5H-imidazo[2,1-b][1,3]oxazine;
P) (6S)-6-({6-[3-Fluoro-4-(trifluoromethoxy)phenyl]-3-pyridinyl}methoxy)-2-nitro-6,7-dihydro-5H-imidazo[2,1-b][1,3]oxazine;
Q) (6S)-6-({5-[3-Fluoro-4-(trifluoromethoxy)phenyl]-2-pyridinyl}methoxy)-2-nitro-6,7-dihydro-5H-imidazo[2,1-b][1,3]oxazine;
R) (6S)-6-({2-Fluoro-4-[6-(trifluoromethyl)-3-pyridinyl]benzyl}oxy)-2-nitro-6,7-dihydro-5H-imidazo[2,1-b][1,3]oxazine;
S) (6S)-2-Nitro-6-[(5-{[6-(trifluoromethyl)-3-pyridinyl]ethynyl}-2-pyridinyl)methoxy]-6,7-dihydro-5H-imidazo[2,1-b][1,3]oxazine;
T) (6S)-6-{[4-(5-Fluoro-2-pyridinyl)benzyl]oxy}-2-nitro-6,7-dihydro-5H-imidazo[2,1-b][1,3]oxazine;
U) (6S)-6-({6-[3-Chloro-4-(trifluoromethoxy)phenyl]-3-pyridinyl}methoxy)-2-nitro-6,7-dihydro-5H-imidazo[2,1-b][1,3]oxazine;

mixtures, optical or geometric isomers, and pharmacologically acceptable salts thereof.

7. A pharmaceutical composition comprising a therapeutically effective amount of the compound of claim 6.

8. The pharmaceutical composition of claim 7, further comprising a pharmaceutically acceptable excipient, adjuvant, carrier, buffer or stabilizer.

9. The pharmaceutical composition of claim 7, further comprising one or more additional anti-infective treatments.

* * * * *